United States Patent
Bansal

(10) Patent No.: US 11,292,847 B2
(45) Date of Patent: Apr. 5, 2022

(54) METHODS FOR TREATING ATOPIC DERMATITIS BY ADMINISTERING AN IL-4R INHIBITOR

(71) Applicant: Regeneron Pharmaceuticals, Inc., Tarrytown, NY (US)

(72) Inventor: Ashish Bansal, White Plains, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 16/409,164

(22) Filed: May 10, 2019

(65) Prior Publication Data

US 2019/0345253 A1 Nov. 14, 2019

Related U.S. Application Data

(60) Provisional application No. 62/670,824, filed on May 13, 2018, provisional application No. 62/840,493, filed on Apr. 30, 2019.

(51) Int. Cl.
*C07K 16/28* (2006.01)
*A61K 39/395* (2006.01)
*A61K 45/06* (2006.01)
*A61P 17/00* (2006.01)
*A61K 39/00* (2006.01)

(52) U.S. Cl.
CPC ...... *C07K 16/2866* (2013.01); *A61K 39/3955* (2013.01); *A61K 45/06* (2013.01); *A61P 17/00* (2018.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,599,905 A | 2/1997 | Mosley | |
| 5,714,146 A | 2/1998 | Lewis | |
| 5,717,072 A | 2/1998 | Mosley | |
| 5,856,296 A | 1/1999 | Mosley | |
| 5,985,280 A | 11/1999 | Ritter | |
| 6,156,877 A | 12/2000 | Ritter | |
| 6,391,581 B1 | 5/2002 | Mosley | |
| 6,548,655 B1 | 4/2003 | Mosley | |
| 6,716,587 B2 | 4/2004 | Mosley | |
| 7,141,653 B2 | 11/2006 | Greenfeder | |
| 7,186,809 B2 | 3/2007 | Pluenneke | |
| 7,317,090 B2 | 1/2008 | Mosley | |
| 7,422,742 B2 | 9/2008 | Greenfeder | |
| 7,531,169 B2 | 5/2009 | Singh | |
| 7,605,237 B2 | 10/2009 | Stevens | |
| 7,608,693 B2 | 10/2009 | Martin | |
| 7,794,717 B2 | 9/2010 | Stevens | |
| 8,030,003 B2 | 10/2011 | Rothenberg | |
| 8,075,887 B2 | 12/2011 | Martin | |
| 8,075,897 B2 | 12/2011 | Spertini | |
| 8,092,802 B2 | 1/2012 | Stevens | |
| 8,092,804 B2 | 1/2012 | Eriksson | |
| 8,252,284 B2 | 8/2012 | Singh | |
| 8,324,192 B2 | 12/2012 | Dohil | |
| 8,337,839 B2 | 12/2012 | Martin | |
| 8,338,135 B2 | 12/2012 | Stevens | |
| 8,497,528 B2 | 7/2013 | Lee | |
| 8,604,171 B2 | 12/2013 | Singh | |
| 8,637,239 B2 | 1/2014 | Furuta | |
| 8,735,095 B2 | 5/2014 | Martin et al. | |
| 8,945,559 B2 | 2/2015 | Dix | |
| 9,238,692 B2 | 1/2016 | Dix | |
| 9,290,574 B2 | 3/2016 | Kostic | |
| 9,574,004 B2 | 2/2017 | Ardeleanu | |
| 10,059,771 B2 | 8/2018 | Mannent | |
| 10,066,017 B2 | 9/2018 | Mannent | |
| 10,137,193 B2 | 11/2018 | Pirozzi | |
| 10,370,449 B2 | 8/2019 | Graham | |
| 10,392,439 B2 | 8/2019 | Stahl | |
| 10,435,473 B2 | 10/2019 | Dix | |
| 10,485,844 B2* | 11/2019 | Radin | A61K 9/0019 |
| 10,669,341 B2 | 6/2020 | Stahl | |
| 10,676,530 B2 | 6/2020 | Stahl | |
| 10,730,948 B2 | 8/2020 | Kostic | |
| 11,034,768 B2 | 6/2021 | Amin | |
| 11,053,309 B2 | 7/2021 | Radin | |
| 2003/0103938 A1 | 6/2003 | Jinquan | |
| 2003/0113387 A1 | 6/2003 | Tsuchida | |

(Continued)

FOREIGN PATENT DOCUMENTS

| | | |
|---|---|---|
| EP | 0604693 | 7/1994 |
| EP | 0367566 | 5/1997 |

(Continued)

OTHER PUBLICATIONS

Cork et al; British Association of Dermatologists Jul. 2017) 177 (Suppl. 1), pp. 25-77.*
ClinicalTrials.gov Identifier: NCT02407756; Aug. 2016.*
Dupixent, (dupilumab) patient information , Mar. 2017.*
W. Carr, Pediatric Drugs; 2013; vol. 15, pp. 303-310.*
Abonia et al. (2013) Journal of Allergy Clin Immunol "High prevalence of eosinophilic esophagitis in patients with inherited connective tissue disorders".
Abstracts, "Human Clinical Research and Therapeutics", Journal of Investigative Dermatology vol. 133, Supplement 1, (2013), pp. S159-S190, Abstracts 1042, and 1048 to 1050, http://apps.webofknowledge.com/full_record.do?product=WOS&search_mode=GeneralSearch&qid=2&SID=E6MDFsiCnXC9MfROx21&page=1&doc=1, 32 pages.

(Continued)

*Primary Examiner* — Joanne Hama
*Assistant Examiner* — Fozia M Hamud
(74) *Attorney, Agent, or Firm* — Merchant & Gould, P.C.

(57) ABSTRACT

The present invention provides methods for treating moderate-to-severe or severe atopic dermatitis (AD). The methods of the present invention comprise administering to a subject in need thereof one or more doses of an interleukin-4 receptor (IL-4R) inhibitor such as an anti-IL-4R antibody.

20 Claims, No Drawings

Specification includes a Sequence Listing.

(56) References Cited

U.S. PATENT DOCUMENTS

| | | |
|---|---|---|
| 2003/0124121 A1 | 7/2003 | Pluenneke |
| 2005/0031609 A1 | 2/2005 | Hultsch |
| 2005/0074462 A1 | 4/2005 | Holmgren |
| 2005/0118176 A1 | 6/2005 | Mosley |
| 2005/0255532 A1 | 11/2005 | Ruben |
| 2005/0282181 A1 | 12/2005 | Yan |
| 2006/0013811 A1 | 1/2006 | Dina |
| 2007/0041976 A1 | 2/2007 | Pluenneke |
| 2007/0274996 A1 | 11/2007 | Carter |
| 2008/0054606 A1 | 5/2008 | Eriksson |
| 2008/0160035 A1 | 7/2008 | Stevens et al. |
| 2009/0074793 A1 | 3/2009 | Martin |
| 2009/0098142 A1 | 4/2009 | Kasaian |
| 2009/0264392 A1 | 10/2009 | Warndahl |
| 2010/0021476 A1 | 1/2010 | Stevens et al. |
| 2010/0047254 A1 | 2/2010 | Martin |
| 2010/0291107 A1 | 11/2010 | Stevens et al. |
| 2011/0195500 A1 | 8/2011 | Rothenberg |
| 2012/0004205 A1 | 1/2012 | Rothenberg |
| 2012/0052072 A1 | 3/2012 | Martin |
| 2012/0097565 A1 | 4/2012 | Dix |
| 2012/0135010 A1 | 5/2012 | Stevens et al. |
| 2012/0164080 A1 | 6/2012 | Hill |
| 2012/0207815 A1 | 8/2012 | Benhamou |
| 2013/0052190 A1 | 2/2013 | Collins |
| 2013/0078675 A1 | 3/2013 | Martin |
| 2013/0324435 A1 | 12/2013 | Rothenberg |
| 2014/0072583 A1 | 3/2014 | Ardeleanu |
| 2014/0187523 A1 | 7/2014 | Dohil |
| 2014/0271681 A1 | 9/2014 | Martin |
| 2014/0356372 A1 | 12/2014 | Stahl |
| 2015/0017176 A1 | 1/2015 | Kostic |
| 2015/0185228 A1 | 7/2015 | Reisacher |
| 2015/0246973 A1 | 9/2015 | Graham |
| 2016/0152718 A1 | 6/2016 | Kostic |
| 2016/0185866 A1* | 6/2016 | Mannent ............... A61K 31/58 424/142.1 |
| 2017/0333557 A1 | 11/2017 | Ardeleanu |
| 2018/0078603 A1* | 3/2018 | Radin .................... A61K 38/02 |
| 2018/0094069 A1 | 4/2018 | Stahl |
| 2018/0094070 A1 | 4/2018 | Stahl |
| 2018/0179288 A1 | 6/2018 | Martin et al. |
| 2019/0040126 A1 | 2/2019 | Radin |
| 2019/0169299 A1 | 6/2019 | Amin |
| 2019/0183973 A1 | 6/2019 | Hamilton |
| 2019/0367622 A1 | 12/2019 | Graham |
| 2020/0246416 A1 | 8/2020 | Radin |
| 2020/0299393 A1 | 9/2020 | Stahl |
| 2020/0332014 A1 | 10/2020 | Kostic |
| 2020/0345843 A1 | 11/2020 | Asrat |
| 2021/0038715 A1 | 2/2021 | Hamilton |
| 2021/0040222 A1 | 2/2021 | Bansal |
| 2021/0163611 A1 | 6/2021 | Martin |
| 2021/0363237 A1 | 11/2021 | Radin |
| 2021/0363264 A1 | 11/2021 | Hamilton |

FOREIGN PATENT DOCUMENTS

| | | |
|---|---|---|
| EP | 1113818 B1 | 5/2006 |
| EP | 2022507 A1 | 2/2009 |
| EP | 1527100 | 7/2009 |
| JP | 05-246874 | 9/1993 |
| JP | 2006-131623 | 5/2006 |
| JP | 2016521713 | 7/2016 |
| RU | 2162711 | 2/2001 |
| RU | 2453303 C1 | 6/2012 |
| WO | WO 1992/19259 | 11/1992 |
| WO | WO 1994/14975 | 7/1994 |
| WO | WO 2001/092340 | 12/2001 |
| WO | WO 2003/048083 | 6/2003 |
| WO | WO 2005/047331 | 5/2005 |
| WO | WO 2005/085284 | 9/2005 |
| WO | WO 2006/003407 | 1/2006 |
| WO | WO 2006/072564 | 7/2006 |
| WO | WO 2006/083390 | 8/2006 |
| WO | WO 2008/054606 | 5/2008 |
| WO | 2008/116149 | 9/2008 |
| WO | WO 2009/124954 | 10/2009 |
| WO | WO 2010/053751 | 5/2010 |
| WO | WO 2010/065557 | 6/2010 |
| WO | WO 2010/120524 | 10/2010 |
| WO | WO 2011/026966 | 3/2011 |
| WO | WO 2012/047954 | 4/2012 |
| WO | WO 2012/094643 | 7/2012 |
| WO | WO 2012/177945 | 12/2012 |
| WO | WO 2013/051928 | 4/2013 |
| WO | WO 2013/088109 | 6/2013 |
| WO | 2013/116287 | 8/2013 |
| WO | WO 2013/155010 | 10/2013 |
| WO | WO 2014/031610 | 2/2014 |
| WO | WO 2014/039461 | 3/2014 |
| WO | WO 2014/059178 | 4/2014 |
| WO | 2014/122144 | 8/2014 |
| WO | WO 2014/197470 | 12/2014 |
| WO | WO 2014/205365 | 12/2014 |
| WO | WO 2015/006571 | 1/2015 |
| WO | 2015/127229 | 8/2015 |
| WO | WO 2016/077675 | 5/2016 |
| WO | WO 2017/143270 | 8/2017 |
| WO | 2018/035393 | 2/2018 |
| WO | 2018/057776 | 3/2018 |
| WO | WO 2018/045130 | 3/2018 |
| WO | 2018/151836 | 8/2018 |
| WO | 2018/201051 | 11/2018 |
| WO | 2019/089473 | 5/2019 |

OTHER PUBLICATIONS

Aceves et al. (2009) Immunol Allergy Clin N Am 29:197-211 "Relationships Between Eosinophilic Inflammation, Tissue Remodeling, and Fibrosis in Eosinophilic Esophagitis".

Akiyama, et al., A Study on Indoor Allergens Measured in Home Environments of Adult-Asthmatic Patients, Housing Research Foundation, Research Annual Report, 1997, No. 24, Study No. 9620, 1-10.

Almagro et al., "Humanization of antibodies", (2008) Frontiers in Bioscience 13:1619-1633.

Antoniu, Sabina, "Pitrakinra, a Dual IL-4R/IL-13 Antagonist for the Potential Treatment of Asthma and Eczema", Current Opinion in Investigational Drugs 2010 11 (11): 1286-1294.

Arron et al. (2009) Am. J. Respir. Crit. Care Med. Online Abstracts Issue. 2009, B21 Airway Inflammation: New Information about Mediators and Biomarkers/Poster Discussion/Monday, May 18, 2009 "Peripheral Biomarkers of an IL-13 Induced Bronchial Epithelial Gene Signature in Asthma".

Assa'ad et al. (2011) Gastroenterology 141:1593-1604 "An Antibody Against IL-5 Reduces Numbers of Esophageal Intraepithelial Eosinophils in Children with Eosinophilic Esophagitis".

Assa'ad, Amal, What is new in the Treatment of Eosinophilic Eosophagitis? Clinical and Translational Allergy 2011 (Suppl 1):569, doi: 10.1186/2045-7022-1-S 1-S69.

Bachert et al. (2005) Drugs 65(11):1537-1552 "Pharmacological management of nasal polyposis".

Bagnasco, Diego et al., "A critical evaluation of Anti-IL-13 and Anti-IL-4 Strategies in Severe Asthma", Int. Arch Allergy Immunol 2016; 170: 122-131.

Balint and Larrick (1993) Gene 137:109-118 "Antibody engineering by parsimonious mutagenesis".

Bankhead, Charles, "IL-4 Antibody Tames Atopic Dermatitis", Medpage Today Article, https://www.medpagetoday.com/meetingcoverage/aad/37636, Mar. 3, 2013, 3 pages.

Barnes (2008) The Journal of Clinical Investigation 118(11):3546-3556 "The cytokine network in asthma and chronic obstructive pulmonary disease".

Bateman et al. (2004) Am. J. Respir. Crit. Care Med. 170:836-844 "Can guideline-defined asthma control be achieved?".

Beck et al. (Jul. 10, 2014) New England Journal of Medicine 371(2): 130-139 "Dupilumab treatment in adults with moderate-to-severe atopic dermatitis".

(56) References Cited

OTHER PUBLICATIONS

Beyer et al. (2002) Journal of Allergy Clin Immunol 109(4):707-713 "Human milk-specific mucosal lymphocytes of the gastrointestinal tract display a $T_H2$ cytokine profile".
Bhardwaj and Ghaffari (2012) Ann Allergy Asthma Immunol 109:155-159 "Biomarkers for eosinophilic esophagitis: a review".
Bieber, T., et al., "Atopic dermatitis: a candidate for disease-modifying strategy," Allergy 67 (2012) 969-975.
Blanchard and Rothenberg (2009) Immunol Allergy Clin N Am 29:141-148 "Chemotactic Factors Associated with Eosinophilic Gastrointestinal Diseases".
Blanchard et al. (2005) Clin Exp Allergy 35:1096-1103 "Inhibition of human interleukin-13-induced respiratory and oesophageal inflammation by anti-human-interleukin-13 antibody (CAT-354)".
Blanchard et al. (2006) The Journal of Clinical Investigation 116(2) "Eotaxin-3 and a uniquely conserved gene-expression profile in eosinophilic esophagitis".
Blanchard et al. (2007) Journal of Allergy Clin Immunol 120(6) "IL-13 involvement in eosinophilic esophagitis: Transcriptome analysis and reversibility with glucocorticoids".
Blanchard et al. (2010) The Journal of Immunology "Coordinate Interaction between IL-13 and Epithelial Differentiation Cluster Genes in Eosinophilic Esophagitis".
Blanchard et al. (2011) J Allergy Clin Immunol 127(1):208-217 "A striking local esophageal cytokine expression profile in eosinophilic esophagitis".
Blauvelt, Andrew, et al., "Long-term management of moderate-to-severe atopic dermatitis with dupilumab and concomitant topical corticosteroids (Liberty Ad Chronos): a 1-year, randomised, double-blinded, placebo-controlled, phase 3 trial," www.thelancet.com, published online May 4, 2016, http://dx.doi.org/10.1016/S0140-6736(17)31191-1.
British Society for Allergy and Clinical Immunology (BSACI) Abstracts of the 2013 Annual Meeting (dated Jul. 8-10, 2013), Clinical & Experimental Allergy, 43, 1428-1472, Nov. 22, 2013, https://onlinelibrary.wiley.com/toc/13652222/2013/43/12, 45 pages.
Brown-Whitehorn and Spergel (2010) Expert Rev Clin Immunol. 6:1:101-115 "The link between allergies and eosinophilic esophagitis: implications for management strategies".
BSACI News Report confirming BSACI conference date of Jul. 8-10, 2013, 2 pages.
Burmeister-Getz et al. (2009) J. Clin. Pharmacol. 49:1025-1036 "Human pharmacokinetics/pharmacodynamics of an interleukin-4 and interleukin-13 dual antagonist in asthma".
Burton, et al., "Direct effects of IL-4 on mast cells drive their intestinal expansion and increase susceptibility to anaphylaxis in a murine model of food allergy," Mucosal Immunology, Nov. 14, 2012, doi:10.1038/mi.2012.112.
Caldas et al. (2003) Molecular Immunology 39:941-952 "Humanization of the anti-CD18 antibody 6.7: an unexpected effect of a framework residue in binding to antigen".
Carter (2006) The Journal of Immunology 6:343-357 "Potent Antibody Therapeutics by Design".
Casset et al. (2003) Biochemical and Biophysical Research Communication 307:198-205 "A peptide mimetic of an anti-CD4 monoclonal antibody by rational design".
Chehade and Sampson (2009) Immunol Allergy Clin N Am 29:149-158 "The Role of Lymphocytes in Eosinophilic Gastrointestinal Disorders".
Cheng et al. (2012) Am J Physiol Gastrointest Liver Physiol 303:G1175-G1187 "Tissue remodeling in eosinophilic esophagitis".
Chien et al. (1989) Proc. Natl. Acad. Sci. 86:5532-5536 "Significant structural and functional change of an antigen-binding site by a distant amino acid substitution: Proposal of a structural mechanism".
Clinical Trials, Study NCT00676884—"A Phase Study to Investigate the Effects of Repeated Administration of AeroDerm in Subjects with Atopic Dermatitis", Aeroderm first publication of clinical study protocol in TCS resistant moderate-to-severe AD, May 13, 2008, 6 pages.
Clinical Trials, Study NCT01548404—"Study of Dupilumab in Adult Patients with Extrinsic Moderate-to-severe Atopic Dermatitis", final publication of clinical study protocol, Aug. 27, 2015, 8 pages.
Clinical Trials, Study NCT01548404—"Study of REGN668 in Adult Patients With Extrinsic Moderate-to-Severe Atopic Dermatitis", first publication of clinical study protocol, Mar. 7, 2012, 7 pages.
Clinical Trials, Study NCT01639040—"Study to Assess the Safety of REGN668 (SAR231893) Administered Concomitantly with Topical Corticosteroids (TCS) in Patients with Moderate-to-severe Atopic Dermatitis (AD)", Concomitant treatment with TCS, Jul. 11, 2012, 6 pages.
Collins, Margaret H. et al., "Sa1151—Baseline Characteristics and Correlation Between Dysphagia and Disease Activity in Patients with Eosinophilic Esophagitis in a Randomized, Placebo-Controlled, Phase 2 Dupilumab Trial", abstract, Gastroenterology, vol. 154, No. 6, May 1, 2016, 1 page.
Corren et al. (2010) American Journal of Respiratory and Critical Care Medicine 181(8):788-796 "A Randomized, Controlled, Phase 2 Study of AMG 317, an IL-4R Antagonist, in Patients with Asthma".
Cortes, J.R., et al., Proton pump inhibitors inhibit IL-4 and IL-13 signaling stat6 activation, European Journal of Immunology, (Sep. 2009) vol. 39, Supp.
Davies et al. (1996) Immunotechnol. 2(3):169-179 "Affinity improvement of single antibody VH domains: residues in all three hypervariable regions affect antigen binding".
Davis (2004) Seminars in Immunology 16:239-243 "The evolutionary and structural 'logic' of antigen receptor diversity".
De Pascalis et al. (2002) Journal of Immunology 169(6):3076-3084 "Grafting of "Abbreviated" Complementarity-Determining Regions Containing Specificity-Determining Residues Essential for Ligand Contact to Engineer a Less Immunogenic Humanized Monoclonal Antibody".
Dellon (2013) Dig Dis Sci "The Pathogenesis of Eosinophilic Esophagitis: Beyond the Eosinophil".
Dellon, Evan S. et al., "A Randomized, Double-Blind, Placebo-Controlled Trial of a Novel Recombinant, Humanized, Anti-Interleukin-13 Monoclonal Antibody (RPC4046) in Patients with Active Eosinophilic Esophagitis: Results of the HEROES Study", Oct. 14, 2016, retrieved from the Internet on Sep. 20, 2018 at: https://www.eventscribe.com/2016/ACG/QRcode.asp?Pres=178380, 3 pages.
Desreumaux et al. (1996) Gastroenterology 110:768-774 "Interleukin 3, Granulocyte-Macrophage Colony-Stimulating Factor, and Interleukin 5 in Eosinophilic Gastroenteritis".
Durham, Andrew L. et al., "Targeted anti-inflammatory therapeutics in asthma and chronic obstructive lung disease", Airway Disease Section, Nat'l. Heart and Lung Institute, Imperial College London, UK, published Aug. 12, 2015, 12 pages.
European Notice of Opposition in Application 13765844.9, dated Feb. 22, 2019, 34 pages.
Fillon et al. (2009) Immunol Allergy Clin N Am 29:171-178 "Epithelial Function in Eosinophilic Gastrointestinal Diseases".
Foote and Winter (1992) J. Mol. Biol. 224:487-499 "Antibody Framework Residues Affecting the Conformation of the Hypervariable Loops".
Foroughi et al. (2007) J Allergy Clin Immunol 120(3):594-601 "Anti-IgE Treatment of Eosinophil Associated Gastrointestinal Disorders".
Franciosi and Liacouras (2009) Immunol Allergy Clin N Am 29:19-27 "Eosinophilic Esophagitis".
Garriga, A., "71st Annual Meeting of the American Academy of Dermatology (AAAD) . . . Miami Beach, FL, Mar. 1-5, 2013", Drugs of the Future 2013, 38(4): 275-279, Apr. 2013, https://journals.prous.com/journals/servlet/xmlxls/pk_journals.xml_toc_pr?p_JournalID=2&p_IssueID=1 186, 5 pages.
Gavett et al. (1997) The American Physiological Society 272(16):L253-L261 "Interleukin-4 receptor blockade prevents airway responses induced by antigen challenge in mice".

(56) References Cited

OTHER PUBLICATIONS

Gevaert et al. (2006) Journal of Allergy and Clinical Immunology 118(5):1133-1141 "Nasal IL-5 levels determine the response to anti—IL-5 treatment in patients with nasal polyps".
Giusti et al. (1987) Proc. Natl. Acad. Sci. 84:2926-2930 "Somatic diversification of S107 from an antiphosphocholine to anti-DNA autoantibody is due to a single base change in its heavy chain variable region".
Groves et al. (2007) Aeroderm in AD Poster at St. John's Institute of Dermatology "Inhibition of IL-4 and IL-13 with an IL-4 mutein (Aeroderm) protects against flares in atopic eczema".
Grunewald et al. (1998) The Journal of Immunology 160(8):4004-4009 "An Antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo".
Gussow and Seemann (1991) Methods in Enzymology 203:99-121 "Humanization of Monoclonal Antibodies".
Hamilton, Jennifer D., et al., "Drug evaluation review: Dupilumab in atopic dermatitis," Immunotherapy (Oct. 1, 2015) 7(10), 1043-1058.
Highlights of Prescribing Information, Dupixent {dupilumab) injection, for subcutaneous use Initial U.S. Approval: 2017, U.S. Food and Drug Administration (FDA), Revised Mar. 2017.
Hijnen et al. (2004) J. Allergy Clin. Immunology 113(2): 334-340 "Serum thymus and activation-regulated chemokine (TARC) and cutaneous T Cell-attracting chemokine (CTACK) levels in allergic diseases: TARC and CTACK are disease-specific markers for atopic dermatitis".
Hirano, Ikuo et al., "Dupilumab Efficacy and Safety in Adult Patients With Active Eosinophilic Esophagitis: a Randomized Double-Blind Placebo-Controlled Phase 2 Trial", Oct. 13, 2017, retrieved from the internet on Sep. 20, 2018 at: http://files.shareholder.com/downloads/REGN/6138593856x0x959724/16AF93AE-DAF8-480A-8301-311C91E8FA41/Presentation.pdf, 20 pages.
Hirano, Ikuo et al., "Sa1113—Correlation Between Esophageal Distensibility and Objective Measures of Disease in Patients with Active Eosinophilic Esophagitis: A Post HOC Analysis of a Randomized, Placebo-Controlled, Phase 2 Dupilumab Trial", abstract, Gastroenterology, vol. 154, No. 6, May 1, 2018, 1 page.
Holm et al. (2007) Molecular Immunology 44:1075-1084 "Functional mapping and single chain construction of the anti-cytokeratin 8 monoclonal antibody TS1".
Holt et al. (2003) Trends in Biotechnology 21(11):484-490 "Domain antibodies: proteins for therapy".
Hong, Judith, et al., "Management of Itch in Atopic Dermatitis," Seminars in cutaneous Medicine and Surgery, vol. 30, No. 2, May 14, 2011, pp. 71-86, XP028240445.
Hopkins (2009) Clinical Otolaryngology 34(5):447-454 "Psychometric validity of the 22-item Sinonasal Outcome Test".
Hopkins et al. (2007) Otolaryngology—Head and Neck Surgery 137(4):555-561 "The Lund-Mackay staging system for chronic rhinosinusitis: How is it used and what does it predict?".
International Investigative Dermatology, Edinburgh, Conference Posters, May 8-11, 2013, 4 pages.
Ivashkiin, V. T., et al., "Eosinophilic esophagitis," a textbook for physicians, Moscow, "AISPI RAS" JSC, Feb. 14, 2013, pp. 13-21, 57-62 No English translation. (Cited in Russian Office Action for RU Appl. No. 2016104400).
Ivashkin, V. T., et al., "Eosinophilic esophagitis: literature review and description of own survey," RJGHC, 2012, vol. 22, 1, pp. 71-81.
Jahnz-Rozyk et al. (2005) Allergy 60:685-688 "Serum thymus and activation-regulated chemokine, macrophage-derived chemokine and eotaxin as marker of severity of atopic dermatitis".
Joost, T.H. Van, "Cyclosporin in atopical dermatitis: a multicentre placebo-controlled study", Journal of the American Academy of Dermatology, (1992), vol. 27, Issue 6, Part 1, pp. 922-928.
Journal of Allergy & Clinical Immunology: Abstracts at conference; https://www.jacionline.org/issue/S0091-6749(13)X0013-2, Feb. 2013, 1 page.
Junttila et al. (2008) J. Exp. Med. 205(11):2595-2608 "Tuning sensitivity to IL-4 and IL-13: differential expression of IL-4Rα, IL-13Rα1, and Yc regulates relative cytokine sensitivity".
Jyonouchi et al. (2013) Basic Mechanisms in Allergic Disease "Invariant Natural Killer T cells in children with Eosinophilic Esophagitis".
Kagami et al. (2003) Clin. Exp. Immunology 134:309-313 "Significant elevation of serum levels of eotaxin-3/CCL26, but not of eotaxin-2/CCL24, in patients with atopic dermatitis: serum eotaxin-3/CCL26 levels reflect the disease activity of atopic dermatitis".
Kakinuma et al. (2002) Clin. Exp. Immunol 127:270-273 "Serum macrophage-derived chemokine (MDC) levels are closely related with the disease activity of atopic dermatitis".
Kakinuma, Takashi et al. (2001) J. Allergy Clin. Immunol. 107(3):535-541 "Thymus and activation-regulated chemokine in atopic dermatitis: Serum thymus and activation-regulated chemokine level is closely related with disease activity".
Kakkar, Tarundeep et al. (2011) Pharmaceutical Research 28(10):2530-2542 "Population PK and IgE Pharmacodynamic Analysis of a Fully Human Monoclonal Antibody Against IL4 Receptor".
Katial (2009) Immunol Allergy Clin N Am 29:119-127 "Biomarkers for Nononcologic Gastrointestinal Disease".
Kelly and Liu (2014) World Allergy Organization Journal 7(S1):P8 "Poster 1013: IL-4R alpha antibody inhibits IgE production and airway remodeling in mouse model of house dust mite-induced eosinophilic asthma".
Kim et al. (2004) J Allergy Clin Immunol 114(6):1449-1455 "Rebound eosinophilia after treatment of hypereosinophilic syndrome and eosinophilic gastroenteritis with monoclonal anti-IL-5 antibody SCH55700".
Konikoff et al. (2006) Gastroenterology 131:1381-1391 "A Randomized, Double-Blind, Placebo-Controlled Trial of Fluticasone Propionate for Pediatric Eosinophilic Esophagitis".
Kopf et al. (1993) Letters to Nature 362:245-248 "Disruption of the murine IL-4 gene blocks Th2 cytokine responses".
Kostic et al. (2010) Clinical Immunology 135:S105-S106 "A Fully Human IL4Rα Antibody for Inhibition of IL-4/IL-13-driven TH2 Responses in Allergic Disease".
Kottyan et al. (2014) Nature Genetics "Genome-wide association analysis of eosinophilic esophagitis provides insight into the tissue specificity of this allergic disease".
Kulis et al. (2011) J. Allergy Clin Immunol 127:81-88 "Single-tree nut immunotherapy attenuates allergic reactions in mice with hypersensitivity to multiple tree nuts".
Leung et al. (2003) The New England Journal of Medicine 348:986-993 "Effect of Anti-IgE Therapy in Patients with Peanut Allergy".
Leung et al. (2004) The Journal of Clinical Investigation 113(5): 651-657 "New insights into atopic dermatitis".
Lezcano-Meza et al. (2003) Allergy 58(10):1011-1017 "Interleukin (IL)-4 and to a lesser extent either IL-13 or interferon-gamma regulate the production of eotaxin-2/CCL24 in nasal polyps".
Liacouras et al. (2011) J Allergy Clin Immunol 128(1) "Eosinophilic esophagitis: Updated consensus recommendations for children and adults".
Lin et al (2007) Clinical Reviews in Allergy & Immunology 33(3):167-177 "Role of Bacterial Pathogens in Atopic Dermatitis".
Liu et al. (1999) Gene Therapy 6:1258-1266 "Hydrodynamics-based transfection in animals by systemic administration of plasmid DNA".
Lucendo and Sanchez-Cazalilla (2012) Expert Rev. Clin. Immunol. 8(8):733-745 "Adult versus pediatric eosinophilic esophagitis: important differences and similarities for the clinician to understand".
Ludmila and Xia (2014) World Allergy Organization Journal 7(1):P8 "Poster 1013: IL-4R alpha antibody inhibits IgE production and airway remodeling in mouse model of house dust mite-induced eosinophilic asthma".
Lwin et al. (2011) Modern Pathology 24:556-563 "Eosinophilic gastritis: histopathological characterization and quantification of the normal gastric eosinophil content".
MacCallum et al. (1996) J. Mol. Biol. 262:732-745 "Antibody-antigen Interactions: Contact Analysis and Binding Site Topography".

(56) References Cited

OTHER PUBLICATIONS

Maliszewski et al. (1994) Proc. Soc. Exp. Biol. Med. 206(3):233-237 "In vivo biological effects of recombinant soluble interleukin-4 receptor".
Mannon et al. (2012) GUT 61(12):1765-1773 "Interleukin 13 and its role in gut defence and inflammation".
Mariuzza et al. (1987) Ann. Rev. Biophys. Biophys. Che. 16:139-159 "The Structural Basis of Antigen-Antibody Recognition".
Martel, Britta C., et al., "Translational animal Models of Atopic Dermatitis for Preclinical Studies," Yale Journal of Biology and Medicine 90 (2017), pp. 389-402.
Masterson et al. (2011) Curr Opin Gastroenterol. 27(6):515-522 "Update on clinical and immunological features of eosinophilic gastrointestinal diseases".
Mathias, et al., "IgE-mediated systemic anaphylaxis and impaired tolerance to food antigens in mice with enhanced IL-4 receptor signaling," Journal of Allergy and Clinical Immunology, 2011, vol. 127, No. 3, 795-805, e1-e6.
Mishra and Rothenberg (2003) Gastroenterology 125:1419-1427 "Intratracheal IL-13 Induces Eosinophilic Esophagitis by an IL-5, Eotaxin-1, and STAT6-Dependent Mechanism".
Mishra et al. (2001) J Clin. Invest. 107:83-90 "An etiological role for aeroallergens and eosinophils in experimental esophagitis".
Mishra et al. (2002) The Journal of Immunology 168:2464-2469 "IL-5 Promotes Eosinophil Trafficking to the Esophagus".
Moldoveanu et al. (2009) Journal of Inflammation Research 2:1-11 "Inflammatory mechanisms in the lung".
Molfino et al. (2012) Clinical & Experimental Allergy 42(5):712-737 "Molecular and clinical rationale for therapeutic targeting of interleukin-5 and its receptor".
Morioka et al. (2009) British Journal of Dermatology 160(6):1172-1179 "IL-4/IL-13 antagonist DNA vaccination successfully suppresses Th2 type chronic dermatitis".
Mueller, Thomas D. et al., "Structure, binding, and antagonists in the IL-4/IL-13 receptor system", Biochimica et Biophysica Acta (2002) 237-250.
Müller et al. (1993) Journal of Immunology 150:5576-5584 "Th2 cells mediate IL-4-dependent local tissue inflammation".
Nadeau et al. (2011) J. Allergy Clin. Immunol 127(6) Letters to the Editor "Rapid oral desensitization in combination with omalizumab therapy in patients with cow's milk allergy".
Nadeau, et al., "Oral Immunotherapy and Anti-IgE Antibody-Adjunctive Treatment for Food Allergy," Immunology and Allergy clinics of North America, 2012, vol. 32, No. 1, 111-133.
Nguyen et al. (2011) Immunological Reviews 242(1):258-271 "Immune modulation for treatment of allergic disease".
Nguyen, Tran Hoai et al., "FutureForms of Immunotherapy and Immunomodulators in Allergic Disease", Immunol Allergy Clin N Am 31 (2011); 343-365.
Niederberger (2009) Immunology Letters 122:131-133 "Allergen-specific immunotherapy".
Niranjan et al. (2013) Immunology and Cell Biology pp. 1-8 "Pathogenesis of allergen-induced eosinophilic esophagitis is independent of interleukin (IL)-13".
Noel et al. (2004) The New England Journal of Medicine 351:940-941 "Eosinophilic Esophagitis".
Novartis (2013) QAX576 "A double blinded, randomized, placebo-controlled trial of intravenous QAX576 in the treatment of eosinophilic esophagitis".
Oetjen, Landon K., et al., "Sensory Neurons Co-opt Classical Immune Signaling Pathways to Mediate Chronic Itch," Sep. 21, 2017, Cell 171, 217-228.
Oh et al. (2010) Eur Respir Rev 19(115):46-54 "Investigational therapeutics targeting the IL-4/IL-13/STAT-6 pathway for the treatment of asthma".
Ohno et al. (1985) Proc. Natl. Acad. Sci. USA 82:2945-2949 "Antigen-binding specificities of antibodies are primarily determined by seven residues of $V_H$".
Ong (2012) Expert Opinion on Emerging Drugs 17(2):129-133 "Editorial update on emerging treatments of atopic dermatitis".

Otani et al. (2013) Journal of Allergy and Clinical Immunology 131(6):1576-1582 "Anti-IL-5 therapy reduces mast cell and IL-9 cell Nos. In pediatric patients with eosinophilic esophagitis".
Otulana et al. (2011) Am. J. Respir. Crit. Care Med. 183:A6179 "A Phase 2b Study of Inhaled Pitrakinra, an IL-4R/IL-13 Antagonist, Successfully Identified Responder Subpopulations of Patients with Uncontrolled Asthma".
Oyoshi et al. (2009) Advances in Immunology 102:135-226 "Cellular and Molecular Mechanisms in Atopic Dermatitis".
Paton, D. M., "Dupilumab: human monoclonal antibody against IL-4Ralpha for moderate to severe atopic dermatitis," Drugs Today, vol. 53, No. 9, Sep. 1, 2017, pp. 477-487, XP055465888.
PCT ISRWO for International Patent Application No. PCT/US2018/045195, dated Oct. 4, 2018, 19 pages.
Pesek, Robert D. et al., "Emerging drugs for eosinophilic esophagitis", Expert Opinion on Emerging Drugs, vol. 23, No. 2, Apr. 3, 2018, 12 pages.
Peserico et al. (2008) British Journal of Dermatology 158:801-807 "Reduction of relapses of atopic dermatitis with methylprednisolone aceponate cream twice weekly in addition to maintenance treatment with emollient: a multicentre, randomized, double-blind, controlled study".
Petry et al. (2012) Anais Brasileiro De Dermatologia 87(5):732-733 "Bacterial skin colonization and infections in patients with atopic dermatitis".
Prieto and Richter (2013) Curr Gastroenterol Rep 15:324 "Eosinophilic Esophagitis in Adults: an Update on Medical Management".
Prussin et al. (2009) J Allergy Clin Immunol. 124(6):1326-1332 "Eosinophilic gastrointestinal disease and peanut allergy are alternatively associated with IL-5+ and IL-5− TH2 responses".
Rafi et al. (2010) Allergy and Asthma Proceedings 31(1):76-83 "Effects of omalizumab in patients with food allergy".
Rayapudi et al. (2010) Journal of Leukocyte Biology 88 "Indoor insect allergens are potent inducers of experimental eosinophilic esophagitis in mice".
Receptos, Inc. 2013 Annual Report.
Ring et al. (2012) J. Eur. Acad. Dermatol. Venereol. 26(8):1045-1060 "Guidelines for treatment of atopic eczema (atopic dermatitis) Part 1".
Roitt et al. (2001) Mosby—Harcourt Publishers Limited, Immunology—Sixth Edition "Antigen Presentation" pp. 110-111.
Roll et al. (2006) J. Investig Allergol Clin Immunol 16(2):79-85 "Safety of specific immunotherapy using a four-hour ultra-rush induction scheme in bee and wasp allergy".
Romaniuk, L.I., "Allergen-specific immunotherapy: mechanisms, methods and efficacy", Clinical Immunology, Allergology and Infectology, 2012, special issue, pp. 44-47. (with English translation of the cited portion).
Rothenberg (2004) J Allergy Clin Immunol 113(1):11-28 "Eosinophilic gastrointestinal disorders (EGID)".
Rothenberg (2009) Gastroenterology 137:1238-1249 "Biology and Treatment of Eosinophilic Esophagitis".
Rothenberg, Marc E. et al., "Intravenous anti-IL-13 mAb QAX576 for the Treatment of eosinophilic esophagitis", Journal of Allergy and Clinical Immunology, vol. 135, No. 2, Feb. 1, 2015, pp. 500-507.
Rudikoff et al. (1982) Proc. Natl. Acad. Sci. 79:1979-1983 "Single amino acid substitution altering antigen-binding specificity".
Russian Official Action from Russian Federation for RU Application 2016104400, dated Oct. 6, 2017, with translation, 4 pages.
Saeki, Hidehisa, "Guidelines for Management of Atopic Dermatitis", (Advances in Medicine, Special Issue, 2009, vol. 228(1):75-79 in part), cited in the Japanese Patent Application No. 2015-531149.
Sampson et al. (2011) J. Allergy Clin Immunol. 127(5) Letters to the Editor, "A phase II, randomized, double-blind, parallel-group, placebo-controlled oral food challenge trial of Xolair (omalizumab) in peanut allergy".
Sanofi and Regeneron Report Positive Proof-of-Concept Data for Dupilumab, an IL-4R alpha Antibody, in Atopic Dermatitis, 71st Annual Meeting of the American Academy of Dermatology (2013) http://files.shareholder.com/downloads/REGN/2689212012x0x640531/794a7e54-6904-416b-ba38-a4ccc1726852/REGN_News_2013_3_2_General_Releases.pdf.

(56) References Cited

OTHER PUBLICATIONS

Sanofi with Regeneron Pharmaceuticals "An Evaluation of Dupilumab in Patients with Nasal Polyposis and Chronic Symptoms of Sinusitis" Trial in Progress, Jun. 2014. ClinicalTrials.gov Identifier: NCT01920893. Retrieved from the Internet URL: http://clinicaltrials.govishow/NCT01920893 Accessed on Sep. 29, 2014.

Sanofi, "Positive Phase 2a Results of Dupilumab in Asthma in the New England Journal of Medicine," May 21, 2013, Regeneron Pharmaceuticals, Inc.

Sanofi/Regeneron Press Release, "Sanofi and Regeneron Report Positive Results with Sarilumab in First Phase 3 Rheumatoid Arthritis Registration Trial", Paris, France and Tarrytown, NY, Nov. 22, 2013, 3 pages.

Sato et al. (1993) J. Immunol. 150(7):2717-2723 "Recombinant soluble murine IL-4 receptor can inhibit or enhance IgE responses in vivo".

Scavuzzo et al. (2005) Biomedicine & Pharmacotherapy 59(6):323-9 "Inflammatory mediators and eosinophilia in atopic and non-atopic patients with nasal polyposis".

Schmidt-Weber (2012) Chem Immunol Allergy 96:120-125 "Anti-IL-4 as a New Strategy in Allergy".

Schmitt et al. (2007) J. of Allergy and Clinical Immunology 120(6):1389-1398 "What are the best outcome measurements for atopic eczema? A systematic review".

Schneider et al. (2013) J. Allergy Clin Immunol 132(6):1368-1374 "A pilot study of omalizumab to facilitate rapid oral desensitization in high-risk peanut-allergic patients".

Sekiya et al. (2002) Allergy 57:173-177 "Increased levels of a TH2-type CC chemokine thymus and activation-regulated chemokine (TARC) in serum and induced sputum of asthmatics".

Silverberg J.I., et al., "Dupilumab treatment induces rapid clinical improvement of itch in patients with moderate-to-severe atopic dermatitis" Paper presented at: American Academy of Dermatology—76th Annual Meeting; Feb. 16-20, 2018; San Diego, CA, USA.

Silverberg J.I., et al., P481, "Dupilumab treatment rapidly improves itch in patients with moderate-to-severe atopic dermatitis" An Allergy Asthma Immunol. 2017;119(suppl 5):S95.

Simpson, E.L., et al., "Two Phase 3 Trials of Dupilumab versus Placebo in Atopic Dermatitis," The New England Journal of Medicine, Oct. 1, 2016, DOI: 10.1056/NEJMoa1610020.

Simpson, Eric L. et al., "Dupilumab therapy provides clinically meaningful improvement in patient-reported outcomes (PROs): A phase IIb, randomized, placebo-controlled, clinical trial in adult patients with moderate to severe atopic dermatitis (AD)", Journal of the American Academy of Dermatology, Mosby, Inc., US, vol. 75, No. 3, Jun. 4, 2016.

Simpson, Eric L. et al., "Patient burden of moderate to severe atopic dermatitis (AD): Insights from a phase 2b clinical trial of dupilumab in adults," Journal of the American Academy of Dermatology, Mosby, Inc., US, vol. 74, No. 3, Jan. 14, 2016.

Slager et al. (2012) Journal of Allergy, Asthma and Immunology 130(2):516-522.e4 "IL-4 Receptor Polymorphisms Predict Reduction in Asthma Exacerbations During Response to an Anti IL-4 Receptor Antagonist".

Spirin (1986) Vysshaya shkola, Moscow, pp. 17-23 "Molecular Biology Ribosome structure and protein biosynthesis", original Russian article and English language translation of same provided by foreign associate handling local prosecution of Russian application No. 2011120194.

Stein et al. (2006) J Allergy Clin Immunol 118(6):1312-1319 "Anti-IL-5 (mepolizumab) therapy for eosinophilic esophagitis".

Steinke and Borish (2001) Respiratory Research 2(2):1-5 "Th2 cytokines and asthma Interleukin-4: its role in the pathogenesis of asthma, and targeting it for asthma treatment with interleukin-4 receptor antagonists".

Stone et al. (2008) Clinical & Experimental Allergy 38(12):1858-1865 "Immunomodulatory therapy of eosinophil-associated gastrointestinal diseases".

Strauman (2009) Immunol Allergy Clin N Am 29:11-18 "Clinical Evaluation of the Adult who has Eosinophilic Esophagitis".

Straumann (2005) J Allergy Clin Immunol 115(2):418-419 "Eosinophilic esophagitis: Escalating epidemiology?".

Straumann et al. (2001) J Allergy Clin Immunol 108(6):954-961 "Idiopathic eosinophilic esophagitis is associated with a $T_H2$-type allergic inflammatory response".

Straumann et al. (2009) Gut "Anti-interleukin-5 antibody treatment (mepolizumab) in active eosinophilic oesophagitis: a randomized, placebo-controlled, double-blind trial".

Tazawa et al. (2004) Arch Dermatol Res 295:459-464 "Relative importance of IL-4 and IL-13 in lesional skin of atopic dermatitis".

Tepper et al. (1990) Cell 52:457-467 "IL-4 Induces Allergic-like Inflammatory Disease and Alters T Cell Development in Transgenic Mice".

Terui, et al., "Learning from Fungus Allergy in Atopic Dermatitis Patients," Japan J. Med. Mycol, 2000, vol. 41, No. 3, 157-160.

Thaci, Diamant et al.: "Efficacy and Safety of Dupilumab in Adults with Moderate-to-Severe Atopic Dermatitis Inadequately Controlled by Topical Treatments: A Randomised, placebo-controlled, dose-ranging phase 2b trial," The Lancet, The Lancet Publishing Group, GB, vol. 387, No. 10013, Oct. 8, 2015.

Tomkinson et al. (2001) J. Immunol 166:5792-5800 "A Murine IL-4 Receptor Antagonist that Inhibits IL-4- and IL-13-induced Responses Prevents Antigen-Induced Airway Eosinophilia and Airway Hyper-responsiveness".

Tsianakas, Athanasios et al., "Dupilumab: A Milestone in the Treatment of Atopic Dermatitis," The Lancet, The Lancet Publishing Group, GB vol. 387, No. 10013, Oct. 8, 2015.

Ul-Haq, Zaheer et al., "Interleukin-4 receptor signaling and its binding mechanism: A therapeutic insight from inhibitors tool box", Cytokine & Growth Factor Review 32 (2016) 3-15.

Vajdos et al. (2002) Journal of Molecular Biology 320(2):415-428 "Comprehensive functional maps of the antigen-binding site of an anti-ErbB2 antibody obtained with shotgun scanning mutagenesis".

Vakharia, Paras P. et al., "Monoclonal Antibodies for Atopic Dermatitis: Progress and Potential", BioDrugs (2017) 31:409-422.

Veerappan et al. (2009) Clinical Gastroenterology and Hepatology 7:420-426 "Prevalence of Eosinophilic Esophagitis in an Adult Population Undergoing Upper Endoscopy: A Prospective Study".

Vestergaard et al. (2000) The Journal of Investigative Dermatology 115(4):640-646 "A $Th_2$ Chemokine, TARC, Produced by Keratinocytes May Recruit $CLA^+CCR4^+$ Lymphocytes into Lesional Atopic Dermatitis Skin".

Virchow et al. (1994) Lung 172:313-334 "Cellular and immunological markers of allergic and intrinsic bronchial asthma".

Walker et al. (1993) Clinical and Experimental Allergy 23:145-153 "Atopic dermatitis: correlation of peripheral blood T cell activation, eosinophilia and serum factors with clinical severity".

Wang and Liu (2008) Current Opinion in Immunology 20:697-702 "The IL-17 cytokine family and their role in allergic inflammation".

Wang, et al., "Peanut-induced intestinal allergy is mediated through a mast cell-IgE-FceRI-IL-13 Pathway," Journal of Allergy and Clinical Immunology, 2010, vol. 126, No. 2, 306-316, e1-e12.

Wark et al. (2006) Advanced Drug Delivery Reviews 58:657-670 "Latest technologies for the enhancement of antibody affinity".

Watson et al. (2011) Allergy, Asthma & Clinical Immunology 7:S4 "Atopic dermatitis".

Weihrauch et al. (2005) Cancer Research 65:5516-5519 "Elevated Serum Levels of CC Thymus and Activation-Related Chemokine (TARC) in Primary Hodgkin's Disease: Potential for a Prognostic Factor".

Weinbrand-Goichberg et al. (2013) Immunol Res "Eosinophilic esophagitis: an immune-mediated esophageal disease".

Wenzel et al. (2007) Lancet 370:1422-1431 "Effect of an interleukin-4 variant on late phase asthmatic response to allergen challenge in asthmatic patients: results of two phase 2a studies".

Wenzel et al. (2010) European Respiratory Society, Annual Congress 2010, "ERS—Programme" pp. 3980.

Wenzel et al. (2013) New England Journal of Medicine 368(26):2455-2466 "Dupilumab in Persistent Asthma with Elevated Eosinophil Levels".

Wershil (2009) Immunol Allergy Clin N Am 29:189-195 "Exploring the Role of Mast Cells in Eosinophilic Esophagitis".

(56) References Cited

OTHER PUBLICATIONS

Whalley et al. (2004) British Journal of Dermatology 150:274-283 "A new instrument for assessing quality of life in atopic dermatitis: international development of the Quality of Life Index for Atopic Dermatitis (QoLIAD)".
Wilhelm and Stockinger (2011) Frontiers in Immunology 2(68) "Innate lymphoid cells and type 2 (Th2) mediated immune responses-pathogenic or beneficial?".
Wills-Karp and Finkelman (2008) Science Signaling 1(51) "Untangling the Complex Web of IL-4 and IL-13 Mediated Signaling Pathways".
Winkler et al. (2000) J. Immunol. 165(8):4505-4514 "Changing the Antigen Binding Specificity by Single Point Mutations of an Anti-p24 (HIV-1) Antibody".
Winter and Harris (1993) Immunology Today 14(6):243-246 "Humanized Antibodies".
Wong, et al., "Guidelines for the management of atopic dermatitis (eczema) for pharmacists," CPJ/RPC, Sep./Oct. 2017, vol. 150, No. 5.
Wu et al. (1999) Journal of Molecular Biology 294:151-162 "Humanization of a murine monoclonal antibody by simultaneous optimization of framework and CDR residues".
Yamanaka et al. (2011) Curr Probl Dermatol 41:80-92 "The Role of Cytokines/Chemokines in the Pathogenesis of Atopic Dermatitis".
Yan and Shaffer (2006) World J Gastroenterol 12(15):2328-2334 "Eosinophilic esophagitis: A newly established cause of dysphagia".
Zuo et al. (2010) Journal of Immunology 185:660-669 "IL-13 Induces Esophageal Remodeling and Gene Expression by an Eosinophil-Independent, IL-13R{alpha}2-Inhibited Pathway".
Zurawski et al. (1995) J. Biol. Chem. Am. Society of Biolochemical Biologists 270(23):13869-13878 "The primary binding subunit of the human Interleukin-4 receptor is also a component of the Interleukin-13 receptor".
Clinical Trials Study No. NCT01312961—"Efficacy, Safety, and Tolerability of Dupilumab in Patients with Persistent Moderate to Severe Eosinophilic Asthma", In: ClinicalTrials.gov, A service of the U.S. National Institutes of Health, First Received: Mar. 11, 2011, 10 pages, Available from: https://clinicaltrials.gov/ct2/show/NCT01312961.
Kopp, M.V. et al., "Combination of omalizumab and specific immunotherapy is superior to immunotherapy in patients with seasonal allergic rhinoconjunctivitis and co-morbid seasonal allergic asthma", Clinical and Experimental Allergy, vol. 39, No. 2, pp. 271-279, published on Jan. 22, 2009.
Darsow, Ulf et al., "Pruritus and Atopic Dermatitis", Clinic Rev Allerg Immunol (2011) 41:237-244.
Buddenkotte, J. et al., "Pathophysiology and therapy of pruritus in allergic and atopic diseases", Allergy 65 (2010), 805-821.
Regeneron: "Highlights of Prescribing Information See 17 for Patient Counseling Information and FDA-approved patient labeling. Revised: Mar. 2017 Full Prescribing Information: Contents 1 Indications and Usage 2 Dosage and Administration 2.1 Dosage 2.2 Important Administration Instructions 2.3 Preparation for Use", (Apr. 7, 2017), XP055534130, Retrieved from the Internet: URL: https://web.archive.org/web/20170407151633if_/https://www.regeneron.com/sites/default/files/Dupixent_FPI.pdf, 4 pages.
Huang, Evie et al: "Severe Atopic Dermatitis in Children", Current Allergy and Asthma Reports, Current Science, US, vol. 18, No. 6, May 10, 2018, pp. 1-8.
Akinlade, B. et al: "Conjunctivitis in dupilumab clinical trials", British Journal of Dermatology, Mar. 9, 2019), pp. 1-15.
Regeneron: "Dupixent: Highlights of Prescribing Information", (Mar. 1, 20191), pp. 1-8, XP55610296, Retrieved from the Internet: URL: https://dlegnxy4jxlq3f.cloudfront.net/Regeneron/Dupixent_FPI.pdf, 8 pgs.
Paller et al: "Early and sustained, clinically meaningful responses with dupilumab treatment in a phase 3 trial in adolescents with moderate-to-severe atopic dermatitis", Pediatric Dermatology, vol. 36, No. Suppl. 1, (Apr. 29, 2019), p. S4.
Database Embase [Online], Elsevier Science Publishers, Amsterdam,NL; (May 1, 2019), Cork M. J: "605 Efficacy and safety of dupilumab in adolescent patients with moderate-to-severe atopic dermatitis", XP002793331, Database accession No. EMB-002001809007 abstract, 3 pages.
Database Embase [Online], Elsevier Science Publishers, Amsterdam,NL; (May 1, 2019), Paller, A.S.: "621 Dupilumab in adolescents with moderate-to-severe atopic dermatitis and a history of inadequate response, or intolerance to cyclosporine: subgroup analysis from a pivotal 16-week trial", XP002793332, Database accession No. EMB-002001808313, Abstract, 2 pages.
Chan, L.S. et al., "Expression of Interieukin-4 in the epidermis of transgenic mice results in pruritic inflammatory skin disease: an experimental animal model to study atopic dermatitis", J. Invest. Dermatol., 2001, 117: 977-983.
Phan, N.Q. et al., "Assessment of pruritus intensity: prospective study on validity and reliability of the visual analogue scale, numeric rating scale, and verbal rating scale in 471 patients with chronic pruritis", Acta. Derm. Venereol., 2012, 92: 502-507.
Marone et al., "The Intriguing Role of Interleukin 13 in the Pathophysiology of Asthma", Frontiers in Pharmacology, 2019, pp. 1-3.
Wegmann et al., "Targeting Cytokines in Asthma therapy: could IL-37 be a Solution?", Expert Review of Respiratory Medicine, 2017, vol. 11, No. 9, pp. 675-677.
Nicodeme et al., "Esophageal Distensibility as a Measure of Disease Severity in Patients with Eosinophilic Esophagitis", Clinical Gastroenterology and Hepatology, 2013, vol. 11, No. 9, pp. 1101-1107.
Blankestijn, Mark et al., "Could Duratumumab be used to treat severe allergy?", Journal of Allergy and Clinical Immunology, vol. 139, No. 5, Jan. 19, 2017, p. 1677-1678.e3.
Nagaraju et al., "Bortezomib treatment diminishes hazelnut-induced intestinal anaphylaxis in mice: Immunomodulation", European Journal of Immunology, vol. 46, No. 7, May 11, 2016, pp. 1727-1736.
Winter, Oliver et al., "Pathogenic Long-Lived Plasma Cells and Their Survival Niches in Autoimmunity, Malignancy, and Allergy", The Journal of Immunology, vol. 189, No. 11, Nov. 19, 2012, pp. 5105-5111.
Regeneron 2011 Annual Report (Apr. 2011), 12 pages.
ClinicalTrials.gov archive, History of Changes for Study: NCT01548404, "Study of Dupilumab in Adult Patients with Extrinsic Moderate-to-Severe Atopic Dermatitis", (Apr. 19, 2012), 7 pages.
ClinicalTrials.gov archive, History of Changes for Study: NCT01259323, "Sequential Ascending Dose Study to Assess the Safety and Tolerability of REGN668 (SAR231893) in Patients With Atopic Dermatitis", (May 31, 2012), 6 pages.
De Genst, Erwin et al., "Antibody repertoire development in camelids", Developmental and Comparative Immunology, 30 (2006); 187-198.
Ward, E. Sally et al., "Binding activities of a repertoire of single immunoglobulin variable domains secreted from *Escherichia coli*", Nature, 1989, 341:544-546.
Barthelemy, Pierre et al., "Comprehensive analysis of the factors contributing to the stability and solubility of autonomous human VH domains", Journal of Biological Chemistry, 2008, 283:3639-3654.
Choi, Yoonjoo et al., "Predicting antibody complementarity determining region structures without classification", Molecular Biosystems, 2011, 7:3327-334.
Griffiths, Andrew et al., "Human anti-self antibodies with high specificity from phage display libraries", The EMBO Journal, 1993, 12:725-734.
Klimka et al., "Human anti-CD30 recombinant antibodies by guided phage antibody selection using cell panning", British Journal of Cancer, 2000, 83:252-260.
Beiboer, Sigrid et al., "Guided selection of a pan carcinoma specific antibody reveals similar binding characteristics yet structural divergence between the original marine antibody and its human equivalent", Journal of Molecular Biology, 2000; 296:833-849.
Ayars, Andrew G. et al., "Pharmacologic Therapies in Pulmonology and Allergy", 2016 Med Clin N Am 100(4):851-868.
Russian Office Action and Search Report in Application 2019109062, dated Dec. 24, 2020, with English translation, 32 pages.

(56) References Cited

OTHER PUBLICATIONS

Mulder, DJ et al., "Understanding eosinophilic esophagitis: the cellular and molecular mechanisms of an emerging disease", Mucosal Immunology, Mar. 2011, vol. 4, No. 2, pp. 139-147.
Yang, Eun-Seok et al., "Anti-IL-4 Receptor mAB Attenuates Allergic Airway Hyperresponsiveness (AHR) and Inflammation in Allergic Mice", J. Allergy Clin. Immunol., Poster 168, Abstracts S69, vol. 109, No. 1 (2002), 1 page.
Siegfried et al., "Use of dupilimab in pediatric atopic dermatitis: Access, dosing, and implications for managing severe atopic dermatitis", Pediatric Dermatology, vol. 36, No. 1, Jan. 2019, pp. 172-176.
Chen, Ching, et al., "Enhancement and destruction of antibody function by somatic mutation: unequal occurrence is controlled by V gene combinatorial associations", The EMBO Journal vol. 15, No. 12, pp. 2784-2794, 1995.
Kussie, Paul, et al., "A Single Engineered Amino Acid Substitution Changes Antibody Fine Specificity", Journal of Immunology:152, pp. 146-152, 1994.
Mashkovsky, M.D., Moscow, 2001 Medicines, 14th edition, v1:8-9. (Cited in RU Application 2019109062 received on Dec. 24, 2020).
Waccholz et al., "Detection of Allergen-Specific IgE Antibody Responses", 2005, Journal of Immunotoxicology, 1:3-4, 189-199.
Janeway, Jr. et al., Immunobiology, 3rd Edition, 1997, Garland Publishing Inc., pp. 11:1-11:22.
Takashi Yoshike, "Treatment For Atopic Dermatitis", Juntendo Medical Journal, 1999, vol. 45, No. 3, pp. 352-360, 33 pages with English translation.
Manabu Fujimoto, "Oral cyclosporin therapy for atopic dermatitis", Igaku no Ayumi, Journal of Clinical and Experimental Medicine, 2009, vol. 228, No. 1, pp. 98-102, 18 pages with English translation.
Nomura, Ichiro et al., "Staphylococcus Aureus and Atopic Dermatitis", (2000), IRYO vol. 54, No. 2, pp. 62-66, 18 pages with English translation.
Reed, Craig, et al., "Patient-reported outcomes in esophageal diseases", Clinical Gastroenterology and Hepatology, Elsevier, Amsterdam, NL, vol. 16. No. 3, pp. 305-310.
Hamilton, Jennifer et al., "Dupilumab Normalizes the Eosinophilic Esophagitis Disease Transcriptome in Adult Patients With Eosinophilic Esophagitis", May 1, 2020, Abstract, retrieved from internet on Aug. 5, 2021 at: https://www.sciencedirect.com/science/article/pii/S0016508520327669?via%3Dihub, 1 page.
Igelman, Sean et al., "Off-label use of dupilumab for pediatric patients with atopic dermatitis: A multicenter retrospective review", Journal of the American Academy of Dermatology, Mosby, Inc., US, vol. 82, No. 2, Oct. 10, 2019, pp. 407-411.
Gong, J.Q. et al., "Skin Colonization by Staphylococcus aureus in patients with eczema and atopic dermatitis and Yelevant combined topical therapy: a double-blind multicentre randomized controlled trial", British Journal of Dermatology, No. 155, pp. 680-687 (2006), Mar. 28, 2006.
Kharkevich, D.A., Pharmacology (Farmakologiya: A Scholarly Manual), 10th Ed., Moscow: GEOTAR-Media, 2010, pp. 73-74 and pp. 846-847, with English translation of cited pages, 12 pages total.
Krasnyuk et al., "Pharmaceutical Technology: Technology of Dosage Forms: A Textbook for College and University Students", 2nd standard edition, Moscow: Akademiya Publishing Center, 2006, p. 8-9, with English translation of cited pages, 7 pages total.
Bergmann, M.M. et al., "Evaluation of Food Allergy in Patients With Atopic Dermatitis", J Allergy Clin Immunol, 1, pp. 22-28, Jan. 1, 2013.
Kim et al., "Engineering of anti-human interleukin-4 receptor alpha antibodies with potent antagonistic activity", Scientific Reports, 2019, vol. 9, Article No. 7772, pp. 1-12.
Radin et al., "First-in-Human Study of REGN668/SAR231893 (IL-4Rα mAb): Safety, Tolerability and Biomarker Results of a Randomized, Double-Blind, Placebo-Controlled, Single Ascending Dose Study in Healthy Volunteers", J. Allergy Clin. Immunol., 2013, vol. 131(2), Suppl., page AB158, (made available on Jan. 26, 2013), 2 pgs.
Wenzel et al. (Jul. 2, 2016) "Dupilumab efficacy and safety in adults with uncontrolled persistent asthma despite use of medium-to-high-dose inhaled corticosteroids plus a long-acting beta2 agonist: a randomised double-blind placebo-controlled pivotal phase 2b dose-ranging trial," Lancet. 388:31-44.
Celakovska, J. et al., "Sensitization to aeroallergens in atopic dermatitis patients: association with concomitant allergic diseases", JEADV 2015; 29, 1500-1505.
Lucae, S. et al., "IgE responses to exogenous and endogenous allergens in atopic dermatitis patients under long-term systemic cyclosporine A treatment", Allergy 71 (2016); 115-118.

* cited by examiner

METHODS FOR TREATING ATOPIC DERMATITIS BY ADMINISTERING AN IL-4R INHIBITOR

CROSS REFERENCES TO RELATED APPLICATIONS

This application claims the benefit of U.S. Provisional Application No. 62/670,824, filed May 13, 2018, and U.S. Provisional Application No. 62/840,493, filed Apr. 30, 2019, the entire contents of which are incorporated herein by reference.

SEQUENCE LISTING

This application includes a Sequence Listing in electronic format entitled "Sequence-Listing-40848-0095USU1" which was created on May 9, 2019 and which has a size of 10.8 kilobytes (KB) (11,056 bytes). The contents of txt file "Sequence-Listing-40848-0095USU1" are incorporated by reference herein.

FIELD OF THE INVENTION

The present invention relates to methods for treating atopic dermatitis. More specifically, the invention relates to the administration of an interleukin-4 receptor (IL-4R) inhibitor in a subject in need thereof.

BACKGROUND

Atopic dermatitis (AD) is a chronic/relapsing inflammatory skin disease characterized by intense pruritus (i.e., itchiness), xerosis (skin dryness), and eczematous lesions whose features include erythema, infiltration/papulation, oozing with crusting, excoriations, and lichenification. It is often associated with other atopic disorders, such as allergic rhinitis and asthma. Severe disease can be extremely disabling due to several factors: major psychological problems, significant sleep loss, and impaired quality of life (QOL) that lead to a high socioeconomic cost. An estimated 2% to 10% of adults are affected by AD (Bieber 2008, N. Engl. J. Med. 358:1483-94).

The pathophysiology of AD is influenced by a complex interplay between inflammation, environmental factors, genetics and skin barrier dysfunction.

AD is the most common inflammatory skin disease in childhood (Illi et al 2004, J. Allergy Olin, Immunol. 113: 925-31). The disease usually presents during early infancy and childhood, but it can persist into or start in adulthood (Kay et al 1994, J. Am, Acad. Dermatol. 30: 35-9). The disease affects 15 to 30% of children and 2 to 10% of adults in industrialized countries (Bieber 2008, N. Engl. J. Med. 358: 1483-94). Phase 1 of the International Study of Asthma and Allergies in Childhood showed a 1-year period prevalence rate as high as 20% in Australia, England, and Scandinavia (Williams et al 1999, J. Allergy Clin. Immunol. 103: 125-38). Often AD constitutes the first step of atopic march (progression from one atopic disease to another). Approximately up to 60% of AD patients have concomitant asthma or allergic rhinitis or food allergy (Hong et al 2012, Envt. Health Toxicol. 27: e2012006).

The clinical pattern of AD varies with age. Infants typically present with erythematous papules and vesicles on the cheeks, forehead, or scalp, which are exudative and intensely pruritic. The childhood phase typically occurs from 2 years of age to puberty. Children are less likely to have the exudative lesions of infancy, and instead exhibit more lichenified papules and plaques representing the more chronic disease involving the hands, feet, wrists, ankles, and antecubital and popliteal regions. The adult phase of AD begins at puberty and frequently continues into adulthood. Predominant areas of involvement include the flexural folds, the face and neck, the upper arms and back, and the dorsa of the hands, feet, fingers, and toes. The eruption is characterized by dry, scaling erythematous papules and plaques, and the formation of large lichenified plaques from lesional chronicity.

The disease has been shown to have a marked impact on the quality of life (QOL) of patients, greater than that seen in other common skin disorders like psoriasis and acne (Lewis-Jones et al 1995, Brit. J. Dermatol. 132: 942-9). Often severe, pruritus is a universal finding in AD and often results in sleep disruption, irritability, and generalized stress for both the affected patients as well as family members (Kim et al 2012, J. Kar. Med. Sci. 27: 1327-32). In addition to causing discomfort, sleep loss, and psychosocial challenges, AD can impose major financial burdens on families for direct medical care, household accommodations, and missed work (Su et al 1997. Arch. Dis. Child. 76: 159-62; Verboom et al 2002, Brit. J. Dermatol. 147: 716-24; Williams 2005, New Engl. J. Med. 352: 2314-24).

Current treatment options for adolescent patients such as topical steroid creams can cause skin to bruise and break. Non-pharmacological management of AD, which includes environmental control measures (e.g., avoidance of antigen and skin irritants) and skin care measures (e.g., maintaining the hydration of the skin through the use of emollients) play a supportive role, especially in children with moderate-to-severe disease. Pharmacological management of AD in children is mainly limited to topical therapy with topical corticosteroids (TCS) and topical calcineurin inhibitors (TCIs). Topical corticosteroids reduce inflammation and pruritus, and are useful in controlling acute flares. However, long-term use of TCS in children is not recommended because of the risk of irreversible skin atrophy, dyspigmentation, acneiform eruptions, and risks associated with systemic absorption (e.g., growth retardation, hypothalamic pituitary axis effects, etc.). Topical calcineurin inhibitors, such as tacrolimus and pimecrolimus, are also used in AD many times as an alternative to or in combination with TCS. However, the use of TCI is frequently associated with skin irritation. Furthermore, a possible increased risk of malignancy (lymphoma and skin cancers) has been noted for TCIs (refer to products' US prescribing information).

To date, the only systemic agents approved for the treatment of AD in children are systemic corticosteroids. Other systemic agents are used off label (cyclosporine, methotrexate, azathioprine, and mycophenolate mofetil) and lack robust evidence for the basis of use. Oral steroids and non-steroidal immunosuppressants can compromise a patient's health later in life. All of these systemic agents have significant side effects, including stunted growth, diabetes, hypertension, osteoporosis (corticosteroids), myelosuppression and hepatotoxicity (methotrexate), nephrotoxicity and hypertension (cyclosporine), and gastrointestinal disturbances and leucopenia (azathioprine). Moreover, a high proportion of patients in which disease is initially controlled by systemic agents suffer from relapse soon after therapy is discontinued (Granlund et al 1995, Br. J. Dermatol. 132: 106-112; Schmitt et al 2009, Br. J. Dermatol. 162: 661-8).

Accordingly, currently there is a high unmet medical need for a safe and effective therapy for AD in children.

BRIEF SUMMARY OF THE INVENTION

According to certain aspects of the present invention, methods are provided for treating, preventing and/or reducing the severity of a symptom of atopic dermatitis (AD), including moderate-to-severe AD or severe AD in a patient ≥12 and <18 years of age, wherein the patient has disease that cannot be adequately controlled by topical medications or for whom topical treatment is inadvisable (e.g., due to intolerance, adverse side effects or safety risks). In one embodiment, the patient has moderate-to-severe AD and a history of inadequate response, intolerance or contraindication to a systemic therapy (e.g., Cyclosporine A, methotrexate, azathiosporine, an oral corticosteroid). In some embodiments, the present invention includes methods of treating a patient ≥12 and <18 years of age with severe AD that is uncontrolled despite treatment with a systemic therapeutic agent. In some embodiments, the present invention includes methods of treating a patient ≥12 and <18 years of age with severe AD for whom treatment with a systemic therapeutic agent (e.g., a systemic immunosuppressant) is medically inadvisable. The methods of the present invention comprise administering to a subject or a patient in need thereof one or more doses of a pharmaceutical composition comprising a therapeutically effective amount of an interleukin-4 receptor (IL-4R) inhibitor. In certain embodiments, the IL-4R inhibitor is administered as monotherapy. In other embodiments, the IL-4R inhibitor is administered in combination with a topical therapy (such as a topical corticosteroid or a topical calcineurin inhibitor). In one embodiment, the IL-4R inhibitor is an antibody or antigen-binding fragment thereof that binds specifically to IL-4R. In one embodiment, the method comprises administering an initial dose comprising 400 mg of the IL-4R inhibitor followed by one or more doses comprising 200 mg of the IL-4R inhibitor, when the patient is <60 kg in weight. In one embodiment, the method comprises administering an initial dose comprising 600 mg of the IL-4R inhibitor followed by one or more doses comprising 300 mg of the IL-4R inhibitor, when the patient is ≥60 kg in weight.

According to certain aspects of the present invention, methods are provided for treating, preventing and/or reducing the severity of a symptom of atopic dermatitis (AD), including moderate-to-severe AD or severe AD in a patient ≥6 and <12 years of age, wherein the patient has disease that cannot be adequately controlled by topical medications or for whom topical treatment is inadvisable (e.g., due to intolerance, adverse side effects or safety risks). In one embodiment, the patient has moderate-to-severe AD and a history of inadequate response, intolerance or contraindication to a systemic therapy (e.g., Cyclosporine A, methotrexate, azathiosporine, etc.). In some embodiments, the present invention includes methods of treating a patient ≥6 and <12 years of age with severe AD that is uncontrolled despite treatment with a systemic therapeutic agent. In some embodiments, the present invention includes methods of treating a patient ≥6 and <12 years of age with severe AD for whom treatment with a systemic therapeutic agent (e.g., a systemic immunosuppressant) is medically inadvisable. The methods of the present invention comprise administering to a subject or a patient in need thereof one or more doses of a pharmaceutical composition comprising a therapeutically effective amount of an interleukin-4 receptor (IL-4R) inhibitor. In certain embodiments, the IL-4R inhibitor is administered as monotherapy. In other embodiments, the IL-4R inhibitor is administered in combination with a topical therapy (such as a topical corticosteroid or a topical calcineurin inhibitor). In one embodiment, the IL-4R inhibitor is an antibody or antigen-binding fragment thereof that binds specifically to IL-4R.

In certain embodiments, the present invention includes methods to treat moderate-to-severe AD or to improve at least one AD-associated parameter in a patient 6 to 18 years of age, the methods comprising administering a pharmaceutical composition comprising a therapeutically effective amount of an antibody or antigen-binding fragment thereof that binds IL-4R, and determining an improvement in an AD-associated parameter. In one embodiment, the patient has moderate-to-severe AD and a history of inadequate response, intolerance or contraindication to a systemic therapy (e.g., Cyclosporine A, methotrexate, azathiosporine, etc.). In certain embodiments, the administration of the IL-4R inhibitor results in an improvement in one or more AD-associated parameters selected from the group consisting of Investigators Global Assessment (IGA); Body Surface Area Involvement of Atopic Dermatitis (BSA); Eczema Area and Severity Index (EASI); Scoring atopic dermatitis (SCORAD); 5-D Pruritus Scale; and Pruritus Numeric Rating Scale (NRS), as described elsewhere herein. In certain embodiments, administration of the IL-4R inhibitor results in an improvement in at least one patient-related outcome selected from the group consisting of Global Individual Signs Score (GISS), Patient Oriented Eczema Measure (POEM), Patient-assessed Hospital Anxiety and Depression Scale (HADS) and Patient-reported Dermatology Life Quality Index (DLQI), as described elsewhere herein.

According to certain aspects, the present invention provides methods for treating a patient with moderate-to-severe AD, for reducing pruritus, or for improving at least one AD-associated parameter in a patient with moderate-to-severe AD wherein the patient has disease that cannot be adequately controlled by topical medications or for whom topical treatment is inadvisable (e.g., due to intolerance, adverse side effects or safety risks). In one embodiment, the patient has moderate-to-severe AD and a history of inadequate response, intolerance or contraindication to a systemic therapy (e.g., Cyclosporine A, methotrexate, azathiosporine, an oral corticosteroid). In one embodiment, the patient has an attribute or is selected on the basis of an attribute selected from the group consisting of: (i) the patient has a baseline IGA score=4; (ii) the patient has a baseline IGA score ≥3; (iii) the patient is ≥12 and <18 years of age; (iv) the patient is <60 kg in weight; (v) the patient is ≥60 kg in weight; (vi) the patient is a candidate for systemic therapy; (vii) the patient has disease that is uncontrolled by topical AD therapy; (viii) the patient has a documented history of inadequate response to topical AD therapy or for whom topical therapy is inadvisable due to adverse side effects or safety risks; (ix) the patient has moderate-to-severe AD and a history of inadequate response, intolerance or contraindication to a systemic therapy; (x) the patient has been previously treated with a medication or procedure selected from the group consisting of a topical corticosteroid, a topical calcineurin inhibitor, an anti-histamine, an emollient, a dermatological therapeutic, a systemic glucocorticoid, a non-steroidal systemic immunosuppressant, cyclosporine A, azathioprine, methotrexate, mycophenolate, UV light therapy, and phototherapy; and (xi) the patient has a concomitant disease or disorder selected from the group consisting of food allergy, asthma, seasonal allergy, allergic conjunctivitis, allergic rhinitis, chronic rhinosinusitis, nasal polyps, house dust allergy, hives, and eosinophilic esophagitis. The methods, according to this aspect, comprise administering one or more doses of a pharmaceutical composition comprising a therapeutically effective amount of an IL-4R inhibitor to the patient in need thereof. In certain embodiments, the administration results in one or more of the following effects: (a) more than 60% reduction from baseline in EASI score; (b) more than 35% reduction from baseline in pruritus NRS by week 4 after administration of the first dose; (c) a ≥4-point reduction from baseline in pruritus NRS as early as week 3 after administration of first dose; (d) patient achieves IGA of 0 or 1 ("clear" or "almost clear") with a reduction of ≥2 points from baseline on a 0 to 4 IGA scale; (e) an improvement in the quality of life of the patient. In certain embodiments, the IL-4R inhibitor is administered as monotherapy. In other embodiments, the IL-4R inhibitor is administered in combination with a topical therapy (such as a topical corticosteroid or a topical calcineurin inhibitor). In one embodiment, the method comprises administering an initial dose comprising 400 mg of the IL-4R inhibitor followed by one or more doses comprising 200 mg of the IL-4R inhibitor, when the patient is <60 kg in weight. In one embodiment, the method comprises administering an initial dose comprising 600 mg of the IL-4R inhibitor followed by one or more doses comprising 300 mg of the IL-4R inhibitor, when the patient is ≥60 kg in weight.

In certain embodiments, the present invention includes methods to reduce the dependence on topical corticosteroids (TCS) in a patient with moderate-to-severe AD, wherein the patient is 6 to 18 years of age and wherein the patient has disease that cannot be adequately controlled by topical medications or for whom topical treatment is inadvisable (e.g., due to intolerance, adverse side effects or safety risks), or the patient has moderate-to-severe AD and a history of inadequate response, intolerance or contraindication to a systemic therapy (e.g., Cyclosporine A, methotrexate, azathiosporine, etc.), the methods comprising administering one or more doses of an IL-4R inhibitor to the subject in need thereof. In certain further embodiments, a medium-potency or high-potency TCS is concomitantly administered with the IL-4R inhibitor. In one further embodiment, the amount of TCS is gradually reduced by at least 20%, at least 30%, at least 40% or at least 50% upon administration of the first dose of the IL-4R inhibitor. In one embodiment, the method comprises administering an initial dose comprising 400 mg of the IL-4R inhibitor followed by one or more doses comprising 200 mg of the IL-4R inhibitor, when the patient is <60 kg in weight. In one embodiment, the method comprises administering an initial dose comprising 600 mg of the IL-4R inhibitor followed by one or more doses comprising 300 mg of the IL-4R inhibitor, when the patient is ≥60 kg in weight.

According to certain aspects, the present invention includes methods to reduce flares or AD exacerbations, the methods comprising selecting a patient with moderate-to-severe or severe AD wherein the patient is 6 to 18 years of age and wherein the patient has disease that cannot be adequately controlled by topical medications or for whom topical treatment is inadvisable (e.g., due to intolerance, adverse side effects or safety risks), or the patient has moderate-to-severe AD and a history of inadequate response, intolerance or contraindication to a systemic therapy (e.g., Cyclosporine A, methotrexate, azathiosporine, etc.); and administering one or more doses of an IL-4R inhibitor to the patient in need thereof. In certain embodiments, the patient has refractory AD or has relapsed after therapy with a systemic therapeutic agent (e.g., a systemic immunosuppressant).

According to certain aspects, the present invention includes methods to treat AD or to reduce pruritus or to improve an AD-associated parameter, the methods comprising selecting a patient with moderate-to-severe or severe AD wherein the patient is 6 to 18 years of age, and has been previously treated more than 5 weeks ago, more than 8 weeks ago, more than 13 weeks ago, or more than 20 weeks ago with an IL-4R inhibitor (e.g., an anti-IL-4R antibody such as dupilumab) and re-treating the patient in need thereof with one or more doses of an IL-4R inhibitor wherein the re-treatment leads to more than 70% reduction from baseline in EASI score, more than 50% reduction from baseline in pruritus NRS, a ≥4-point reduction from baseline in pruritus NRS, and/or a reduction of ≥2 points from baseline on a 0 to 4 IGA scale. In certain embodiments, each dose of the IL-4R inhibitor comprises about 50-600 mg and is administered 1, 2, 3 or 4 weeks after the immediately preceding dose.

According to certain embodiments, the methods of the present invention comprise administering one or more doses of an IL-4R inhibitor to a subject in need thereof. In certain embodiments, the methods of the present invention comprise administering about 10 mg to about 600 mg of an IL-4R inhibitor as an initial dose followed by one or more secondary doses, each secondary dose comprising 25 to 400 mg of an IL-4R inhibitor. In certain embodiments, the initial dose and the one or more secondary doses each comprise about 10 mg to about 600 mg of the IL-4R inhibitor. In certain embodiments, the IL-4R inhibitor is administered at an initial dose of 600 mg followed by one or more secondary doses wherein each secondary dose comprises 300 mg. According to this aspect of the invention, the IL-4R inhibitor may be administered to the subject at a dosing frequency of, e.g., once a week, once in 2 weeks, once in 3 weeks or once in 4 weeks. In one embodiment, each secondary dose is administered 1 week after the immediately preceding dose. In one embodiment, each secondary dose is administered 2 weeks after the immediately preceding dose. In one embodiment, each secondary dose is administered 4 weeks after the immediately preceding dose. In certain embodiments, the methods of the present invention comprise administering an IL-4R inhibitor to a subject in need thereof wherein the IL-4R inhibitor comprises about 1-10 mg/kg of the subject's body weight. In certain embodiments, the subject in need thereof is administered one or more doses of the IL-4R inhibitor wherein each dose comprises 1, 2, 4, 5 or 10 mg/kg of the subject's body weight and wherein each dose is administered 1-4 weeks after the immediately preceding dose.

In certain embodiments, the invention includes methods for treating moderate-to-severe atopic dermatitis (AD) or improving an AD-associated parameter, the methods comprising: (a) selecting a patient with moderate-to-severe AD wherein the patient has disease that cannot be adequately controlled with topical AD medications or for whom topical treatment is medically inadvisable, and wherein the patient is ≥12 and <18 years of age, and/or the patient has moderate-to-severe AD and a history of inadequate response, intolerance or contraindication to a systemic therapy (e.g., Cyclosporine A, methotrexate, azathiosporine, etc.); and (b) administering an initial dose followed by one or more secondary doses of a therapeutically effective amount of an interleukin-4 receptor (IL-4R) inhibitor to the patient in need thereof; wherein the initial dose comprises 400 mg and each secondary dose comprises 200 mg of the IL-4R inhibitor if the patient is <60 kg in weight.

In certain embodiments, the invention includes methods for treating moderate-to-severe atopic dermatitis (AD) or improving an AD-associated parameter, the methods comprising: (a) selecting a patient with moderate-to-severe AD wherein the patient has disease that cannot be adequately controlled with topical AD medications or for whom topical treatment is medically inadvisable, and wherein the patient is ≥12 and <18 years of age and/or the patient has moderate-to-severe AD and a history of inadequate response, intolerance or contraindication to a systemic therapy; and (b) administering an initial dose followed by one or more secondary doses of a therapeutically effective amount of an interleukin-4 receptor (IL-4R) inhibitor to the patient in need thereof; wherein the initial dose comprises 600 mg and each secondary dose comprises 300 mg of the IL-4R inhibitor if the patient is ≥60 kg in weight.

Exemplary IL-4R inhibitors that can be used in the context of the methods of the present invention include, e.g., small molecule chemical inhibitors of IL-4R or its ligands (IL-4 and/or IL-13), or biological agents that target IL-4R or its ligands. According to certain embodiments, the IL-4R inhibitor is an antigen-binding protein (e.g., antibody or antigen-binding fragment thereof) that binds the IL-4Ra chain and blocks signaling by IL-4, IL-13, or both IL-4 and IL-13. In one embodiment, the antibody or antigen-binding fragment thereof that specifically binds IL-4R comprises complementarity determining regions (CDRs) in a heavy chain variable region (HCVR)/light chain variable region (LCVR) sequence pair of SEQ ID NOs: 1/2. In certain embodiments, the antibody or antigen-binding fragment thereof comprises a heavy chain CDR (HCDR1) having amino acid sequence of SEQ ID NO: 3, a HCDR2 having amino acid sequence of SEQ ID NO: 4, a HCDR3 having amino acid sequence of SEQ ID NO: 5, a light chain CDR (LCDR1) having amino acid sequence of SEQ ID NO: 6, a LCDR2 having amino acid sequence of SEQ ID NO: 7, and a LCDR3 having amino acid sequence of SEQ ID NO: 8. One such type of antigen-binding protein that can be used in the context of the methods of the present invention is an anti-IL-4Ra antibody such as dupilumab.

In some embodiments, the IL-4R inhibitor is administered subcutaneously, intravenously, or intraperitoneally to the subject. In one embodiment, the IL-4R inhibitor is contained in a container selected from the group consisting of a glass vial, a syringe, a prefilled syringe, an autoinjector and a microinfuser. In one embodiment, the IL-4R inhibitor is contained in a prefilled syringe. In one embodiment, the prefilled syringe is a single-dose prefilled syringe. In one embodiment, the IL-4R inhibitor is contained in an autoinjector. In one embodiment, the autoinjector comprises a prefilled syringe. In one embodiment, the IL-4R inhibitor is contained in a volume of 1.15 mL. In one embodiment, the IL-4R inhibitor is contained in a volume of 2.25 mL.

In certain embodiments, the present invention provides use of an IL-4R inhibitor of the invention in the manufacture of a medicament to treat moderate-to-severe or severe AD or to reduce pruritus in a patient 6 to 18 years of age, wherein the patient has disease that cannot be controlled by topical therapy or for whom topical treatment is medically inadvisable (e.g., due to intolerance, other important side effects or safety risks). In certain embodiments, the patient is resistant or intolerant to systemic therapy or for whom systemic therapy is inadvisable due to safety and health risks coupled with suboptimal efficacy. In certain embodiments, the present invention provides use of an IL-4R inhibitor of the invention in the manufacture of a medicament to reduce dependence on topical corticosteroids in a patient with moderate-to-severe AD. In certain embodiments, the present invention provides use of an IL-4R inhibitor in a method to treat moderate-to-severe AD or to reduce pruritus in a patient with moderate-to-severe AD, wherein the IL-4R inhibitor is administered to a subject in need thereof and wherein the patient has disease that cannot be controlled by topical therapy or for whom topical treatment is medically inadvisable (e.g., due to intolerance, other important side effects or safety risks) and/or the patient has moderate-to-severe AD and a history of inadequate response, intolerance or contraindication to a systemic therapy (e.g., Cyclosporine A, methotrexate, azathiosporine, etc.). In certain embodiments, the present invention provides use of an IL-4R inhibitor in a method to reduce dependence on topical corticosteroids in a subject with moderate-to-severe AD, wherein the IL-4R inhibitor is administered to the subject in need thereof. In one embodiment, the patient is ≥12 to <18 years of age and is <60 kg in weight. In one embodiment, the patient is ≥12 to <18 years of age and is ≥60 kg in weight. In one embodiment, one or more doses of the IL-4R inhibitor are administered to the patient wherein each dose comprises 50-600 mg of the IL-4R inhibitor. In one embodiment, the method comprises administering an initial dose of 400 mg of the IL-4R inhibitor followed by one or more doses comprising 200 mg of the IL-4R inhibitor to a patient ≥12 to <18 years of age and <60 kg in weight. In one embodiment, the IL-4R inhibitor is an antibody or antigen-binding fragment thereof that binds to IL-4R. In one embodiment, the anti-IL-4R antibody comprises a HCVR/LCVR of SEQ ID NOs: 1/2.

Other embodiments of the present invention will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.). As used herein, the terms "treat", "treating", or the like, mean to alleviate symptoms, eliminate the causation of symptoms either on a temporary or permanent basis, or to prevent or slow the appearance of symptoms of the named disorder or condition.

Although any methods and materials similar or equivalent to those described herein can be used in the practice of the present invention, the preferred methods and materials are now described. All publications mentioned herein are incorporated herein by reference to describe in their entirety.

Methods for Treating Moderate-to-Severe Atopic Dermatitis in Adolescents and Children The present invention includes methods which comprise administering to a subject in need thereof a therapeutic composition comprising an IL-4R inhibitor. As used herein, the expression "a subject in need thereof" means a human or non-human animal that exhibits one or more symptoms or indicia of atopic dermatitis, and/or who has been diagnosed with atopic dermatitis.

"Atopic dermatitis" (AD), as used herein, means an inflammatory skin disease characterized by intense pruritus (e.g., severe itch) and by scaly and dry eczematous lesions. The term "atopic dermatitis" includes, but is not limited to, AD caused by or associated with epidermal barrier dysfunction, allergy (e.g., allergy to certain foods, pollen, mold, dust mite, animals, etc.), radiation exposure, and/or asthma. The present invention encompasses methods to treat patients with moderate-to-severe or severe AD. As used herein, "moderate-to-severe AD", is characterized by intensely pruritic, widespread skin lesions that are often complicated by persistent bacterial, viral or fungal infections. Moderate-to-severe AD also includes chronic AD in patients. In many cases, the chronic lesions include thickened plaques of skin, lichenification and fibrous papules. Patients affected by moderate-to-severe AD also, in general, have more than 20% of the body's skin affected, or 10% of skin area in addition to involvement of the eyes, hands and body folds. Moderate-to-severe AD is also considered to be present in patients who require frequent treatment with topical corticosteroids. A patient may also be said to have moderate-to-severe AD when the patient is resistant or refractory to treatment by either a topical corticosteroid or a calcineurin inhibitor.

In certain preferred embodiments, the term "a subject in need thereof" refers to patients with moderate-to-severe AD, wherein the patient is ≥12 and <18 years of age (adolescents). In other preferred embodiments, the term "a subject in need thereof" refers to patients with moderate-to-severe AD, wherein the patient is ≥6 and <12 years of age (children). As used herein, "moderate-to-severe AD" refers to chronic relapsing AD that is refractory to treatment with medium-potency and high-potency TCS and/or immunosuppressant therapy. Moderate-to-severe AD is also characterized by chronic intensely pruritic lesions affecting more than 20% of the body surface area. In certain embodiments, the term refers to chronic AD according to the Eichenfleld criteria (Eichenfield et al 2014, J. Am. Acad. Dermatol. 70: 338-351) for which treatment with potent topical corticosteroids (TCS) is indicated. In certain embodiments, the term includes patients with chronic AD that are frequently treated with topical corticosteroids, and/or have received prior treatment with a systemic therapeutic agent and/or may be resistant to treatment with systemic corticosteroids and/or non-steroidal immunosuppressants. A patient with moderate-to-severe AD may also show frequent exacerbations or flares of the disease. In certain embodiments, the term "moderate-to-severe AD" refers to patients with Investigators Global Assessment (IGA) score of ≥3. In certain embodiments, the term "subject in need thereof" includes patients 6 to 18 years of age that show no improvement in one or more AD-associated parameters upon treatment with a topical therapy including a topical corticosteroid or a topical calcineurin inhibitor. Examples of AD-associated parameters are described elsewhere herein. For example, treatment with a topical therapy may result in no decrease in pruritus or Eczema Area and Severity Index (EASI) score or Body Surface Area (BSA) score. In some embodiments, the term refers to patients with moderate-to-severe AD that have been treated with a topical therapy and/or systemic therapeutic agent but have since relapsed and/or show increased AD exacerbations or flares. In certain embodiments, the term refers to patients 6 to 18 years of age with moderate-to-severe or severe AD for whom topical therapy is inadvisable due to safety and health risks to the patient coupled with suboptimal efficacy. In some embodiments, the present invention includes methods to treat moderate-to-severe AD or severe AD in patients who have been treated earlier with a systemic therapeutic agent for ≥1 month and do not show a decrease in one or more AD-associated parameters. For example, the present methods may be used to treat a patient with chronic relapsing AD who has been treated with a systemic therapeutic agent and has a Body surface Area (BSA) score of ≥10% or an Investigators Global Assessment (IGA) score a ≥3.

As used herein, "flare", also referred to as "exacerbation" refers to an increase in signs and/or symptoms leading to escalation of therapy, which can be an increase in the dose of an immunosuppressant therapy (e.g., cyclosporine A), a switch to a higher-potency class of TCS, or the start of another oral immunosuppressive drug. In certain embodiments, the present invention includes methods to reduce the number of flares or exacerbations in a patient with severe AD, the methods comprising administering a therapeutically effective amount of an IL-4R inhibitor to the patient in need thereof.

In certain embodiments, the term "subject in need thereof" includes patients with moderate-to-severe or severe AD who are 6 to 18 years of age and who have received prior treatment with systemic therapy. As used herein, the term "systemic therapy" refers to systemically administered therapeutic agents (e.g., orally administered corticosteroids). The term includes systemic immunosuppressant or immunomodulatory agents. In the context of the present invention, the term "systemic immunosuppressant" includes, but is not limited to, cyclosporine A, methotrexate, mycophenolate mofetil, azathioprine, systemic or oral corticosteroids, and interferon-gamma. In certain embodiments, the term also includes immunobiologics such as tumor necrosis factor alpha (TNFα) inhibitors (e.g., an anti-TNFα antibody such as infliximab), CD11a inhibitors (e.g., an anti-CD11a antibody such as efalizumab), IgE inhibitors (e.g., omalizumab), CD20 inhibitors (e.g., rituximab). Systemic therapy including systemic immunosuppressants may be used for short-term treatment of flares or as a temporary measure to control disease, but their use is limited by significant side-effects, e.g., growth retardation in children, Cushing's syndrome, hypertension, glucose intolerance, myopathy, osteonecrosis, glaucoma and cataracts. Use of systemic immunosuppressants also caries the risk of rebound phenomenon, wherein symptoms of the disease may worsen significantly following cessation of treatment. In certain embodiments, the terms "systemic therapy", "systemic therapeutic agent" and "systemic immunosuppressant" have been used interchangeably throughout this disclosure.

In certain embodiments, the term "subject in need thereof" includes patients (adolescents or children) with moderate-to-severe or severe AD who have been administered one or more TCS for more than 6 months, more than 1 year, more than 2 years, more than about 5 years, more than about 7 years, or more than about 10 years, optionally in addition to periodic treatment with an immunosuppressant. In certain embodiments, the term "subject in need thereof" includes patients with moderate-to-severe or severe AD that have been previously treated with a therapeutic selected from the group consisting of cyclosporine A, an IgE inhibitor, a TNFalpha inhibitor, a CD11a inhibitor, a CD20 inhibitor, an IL-4R inhibitor (e.g., an anti-IL-4R antibody such as dupilumab), an antibiotic, a systemic immunosuppressant, a topical corticosteroid, an oral corticosteroid, calcineurin inhibitor and phototherapy. The patients may desire to minimize or avoid the adverse side effects of the TCS and/or immunosuppressant. The present invention includes methods to treat moderate-to-severe or severe AD in a patient, the methods comprising administering an IL-4R inhibitor concomitantly with a TCS wherein the dosage is adjusted to minimize or prevent adverse side effects of the TCS. In certain embodiments, the present invention includes methods to reduce dependence on TCS in a patient with moderate-to-severe or severe AD; the methods comprising administering a therapeutically effective amount of an IL-4R inhibitor concomitantly with a potent TCS wherein the amount of TCS used by the patient is reduced by about 50% as compared to a patient not administered the IL-4R inhibitor. In certain embodiments, the present invention includes methods to reduce dependence on TCS in a patient with moderate-to-severe or severe AD, the methods comprising administering a therapeutically effective amount of an IL-4R inhibitor concomitantly with a potent TCS wherein the amount of TCS used by the patient is reduced by at least 20%, at least 30%, at least 40% or at least 50% as compared to the amount used by the patient before treatment with the IL-4R inhibitor. In certain embodiments, the administration of an IL-4R inhibitor and a TCS results in additive or synergistic activity in treating AD as compared to monotherapy.

The term "TCS", as used herein includes group I, group II, group II and group IV topical corticosteroids. According to the Anatomical Therapeutic Classification System of World Health Organization, the corticosteroids are classified as weak (group I), moderately potent (Group II) and potent (Group III) and very potent (Group IV), based on their activity as compared to hydrocortisone. Group IV TCS (very potent) are up to 600 times as potent as hydrocortisone and include clobetasol propionate and halcinonide. Group III TCS (potent) are 50 to 100 times as potent as hydrocortisone and include, but are not limited to, betamethasone valerate, betamethasone dipropionate, diflucortolone valerate, hydrocortisone-17-butyrate, mometasone furoate, and methylprednisolone aceponate. Group II TCS (moderately potent) are 2 to 25 times as potent as hydrocortisone and include, but are not limited to, clobetasone butyrate, and triamcinolone acetonide. Group I TCS (mild) includes hydrocortisone.

Patients with moderate-to-severe or severe AD are often prescribed medium-potency or high-potency TCS for treatment of AD. Such treatment may be, for example, for more than 2 months, for more than 3 months, more than 4 months, more than 5 months, or more than 6 months. It is known in prior art that treatment with TCS leads to adverse side-effects. In certain aspects, the present invention includes methods to reduce use of TCS or dependence on TCS and/or to reduce the adverse side-effects of TCS in a patient with severe AD, the methods comprising administering one or more doses of an IL-4R inhibitor to the patient in need thereof. In certain embodiments, the IL-4R inhibitor is administered in combination with a medium-potency or high-potency TCS, wherein the amount of TCS administered is gradually reduced such that the patients severe AD is treated and/or one or more AD-associated parameters is significantly improved as well as the side effects and toxicity due to TCS are minimized or prevented. In certain embodiments, the present invention includes methods to reduce or eliminate the risk of rebound upon TCS or immunosuppressant reduction or discontinuation, the methods comprising selecting a patient with severe AD that is uncontrolled with a background therapy and administering one or more doses of IL-4R inhibitor to the patient in need thereof. In certain further embodiments, the patient is initially administered one or more doses of IL-4R inhibitor in combination with a concomitantly administered background therapy; followed by gradually reducing the background therapy. In certain embodiments, the background therapy comprises a therapeutic agent selected from the group consisting of TCS, calcineurin inhibitors, a systemic immunosuppressant and emollients. In one embodiment, the patient with severe AD is earlier treated with a systemic immunosuppressant wherein the systemic immunosuppressant is cyclosporine A. In certain embodiments, the amount of the background therapy is reduced by at least 20%, at least 30%, at 40% or at least 50% as compared to a patient that is not administered an IL-4R inhibitor.

The present invention includes methods for treating moderate-to-severe AD by improving one or more atopic dermatitis (AD)-associated parameters in a subject in need thereof, wherein the methods comprise selecting a patient with moderate-to-severe AD, wherein the patient is 6 to 18 years of age and wherein the patient has disease that cannot be adequately controlled with topical therapy or for whom topical treatment is inadvisable; and administering one or more doses of a pharmaceutical composition comprising a therapeutically effective amount of an IL-4R inhibitor to the subject. In one embodiment, the pharmaceutical composition comprising an IL-4R inhibitor is administered in combination with a potent TCS.

Examples of "AD-associated parameters" include: (a) Investigators Global Assessment (IGA); (b) Body Surface Area Involvement of Atopic Dermatitis (BSA); (c) Eczema Area and Severity Index (EASI); (d) SCORAD; (e) 5-D Pruritus Scale; and (f) Pruritus Numeric Rating Scale (NRS). An "improvement in an AD-associated parameter" means a decrease from baseline of one or more of IGA, BSA, EASI, SCORAD, 5-D Pruritus Scale, or NRS. As used herein, the term "baseline," with regard to an AD-associated parameter, means the numerical value of the AD-associated parameter for a subject prior to or at the time of administration of a pharmaceutical composition of the present invention.

To determine whether an AD-associated parameter has "improved," the parameter is quantified at baseline and at one or more time points after administration of the pharmaceutical composition of the present invention. For example, an AD-associated parameter may be measured at day 1, day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with a pharmaceutical composition of the present invention. The difference between the value of the parameter at a particular time point following initiation of treatment and the value of the parameter at baseline is used to establish whether there has been an "improvement" (e.g., a decrease) in the AD associated parameter. AD-associated parameters are described in US Patent Publication No. US20140072583, incorporated herein in its entirety. In the context of the present invention, "a subject in need thereof" may include, e.g., subjects who, prior to treatment, exhibit (or have exhibited) one or more AD-associated parameters such as, e.g., elevated IGA, BSA, EASI, SCORAD, 5D-Pruritus, and/or NRS score. For example, the methods of the present invention comprise administering an IL-4R inhibitor to patients with IGA≥3 or ≥4; or BSA more than 10%.

According to one aspect, the present invention provides methods of treating moderate-to-severe or severe AD or reducing pruritus or improving an AD-associated parameter, the methods comprising: (1) selecting a patient with moderate-to-severe or severe AD wherein the patient has an attribute selected from the group consisting of: (a) patient has a documented history of inadequate response or intolerance to topical therapy including a topical corticosteroid or a topical calcineurin inhibitor; (b) patient has a baseline peak pruritus NRS ≥4; (c) patient has a baseline IGA score a ≥3; (d) patient has a baseline IGA score=4; and (e) patient has a concurrent disease or disorder selected from the group consisting of asthma, allergic rhinitis, food allergy, allergic conjunctivitis, hives, allergy to environmental allergens; and (2) administering one or more doses of a therapeutically effective amount of an IL-4R inhibitor to the patient in need thereof. In certain embodiments, the administration of the IL-4R inhibitor leads to an effect selected from the group consisting of (i) a decrease from baseline of more than 60% in EASI; (ii) a decrease from baseline of about 75% in EASI by Week 2 after administration of the first dose of the IL-4R inhibitor; (iii) a decrease from baseline of more than 45% in pruritus NRS by week 16 after administration of the first dose of the IL-4R inhibitor (iv) ≥4-point improvement in peak pruritus NRS by week 2 after administration of the first dose of the IL-4R inhibitor; (v) a 2-point improvement in IGA score by week 16 after administration of the first dose of the IL-4R inhibitor; (vi) a decrease from baseline in IGA to achieve an IGA score of 0 or 1 by week 16 after administration of the first dose of the IL-4R inhibitor; (vii) a reduction in the number of flares or exacerbations; and (viii) reduction in the incidence of skin infections; and (ix) improvement of quality of life as determined by, for example, Dermatology Life Quality Index (DLQI) or any other patient-reported outcome disclosed herein. In certain embodiments, the IL-4R inhibitor is an anti-IL-4R antibody or antigen-binding fragment thereof (such as dupilumab). In certain embodiments, the IL-4R inhibitor is administered in combination with a second therapeutic agent. In certain embodiments, the second therapeutic agent is selected from the group consisting of topical corticosteroids and topical calcineurin inhibitors. In certain embodiments, each dose of the IL-4R inhibitor comprises 50-600 mg and each dose is administered one week or 2 weeks after the immediately preceding dose. In one embodiment, each dose of the anti-IL-4R antibody comprises 300 mg and wherein each dose is administered once a week or once in 2 weeks. In certain specific embodiments, the one or more doses comprise a first dose comprising 600 mg followed by one or more secondary doses wherein each secondary dose comprises 300 mg and wherein each secondary dose is administered 1 week or 2 weeks after the immediately preceding dose. In certain specific embodiments, the one or more doses comprise a first dose comprising 400 mg followed by one or more secondary doses wherein each secondary dose comprises 200 mg and wherein each secondary dose is administered 1 week or 2 weeks after the immediately preceding dose. In certain specific embodiments, the one or more doses comprise a first dose comprising 600 mg followed by one or more secondary doses wherein each secondary dose comprises 300 mg and wherein each secondary dose is administered 4 weeks after the immediately preceding dose.

According to one aspect, the present invention includes methods for treating AD or for reducing pruritus or for improving an AD-associated parameter in a patient with moderate-to severe or severe AD wherein the patient has been previously treated with an IL-4R inhibitor (e.g., an anti-IL-4R antibody such as dupilumab). In certain embodiments, the patient has been previously treated more than 4 weeks ago, more than 8 weeks ago, more than 12 weeks ago or more than 20 weeks ago with dupilumab. In certain embodiments, the present invention includes methods to treat moderate-to-severe or severe AD in patients whose prior treatment with an IL-4R inhibitor has been interrupted more than 4 weeks ago, more than 8 weeks ago or more than 12 weeks ago. The methods, according to this aspect, comprise re-treating the patient in need thereof with an IL-4R inhibitor wherein the retreatment comprises administering one or more doses of the IL-4R inhibitor such that the patient's disease is treated or at least one AD-associated parameter is improved. In certain embodiments, the retreatment of the patient leads to more than 70% reduction from baseline in EASI score and/or more than 50% reduction from baseline in pruritus NRS score upon administration of the IL-4R inhibitor.

In certain embodiments, the methods of the present invention may be used to treat patients that show elevated levels of one or more AD-associated biomarkers (e.g., IgE). AD-associated biomarkers are described in US Patent Publication No. US20140072583, incorporated herein in its entirety. For example, the methods of the present invention comprise administering an IL-4R inhibitor to patients with elevated levels of IgE or TARC or periostin. In the context of the present invention, "a patient in need thereof" may include, e.g., subjects who, prior to treatment, exhibit (or have exhibited) an elevated level of one or more AD-associated biomarker such as, e.g., IgE and/or TARC. In certain embodiments, "a subject in need thereof" may include a subset of population which is more susceptible to AD or may show an elevated level of an AD-associated biomarker.

According to certain aspects, the present invention includes methods for treating moderate-to-severe or severe atopic dermatitis (AD) or improving an AD-associated parameter, the method comprising: (a) selecting a patient with moderate-to-severe or severe AD wherein the patient has an attribute selected from the group consisting of: (i) the patient has a baseline IGA score=4; (ii) the patient has a baseline IGA score a 3; (iii) the patient is between 6 and 18 years of age; (iv) the patient has disease that is uncontrolled by topical AD therapy; (v) the patient has a documented history of inadequate response to topical AD therapy or for whom topical therapy is inadvisable due to adverse side effects or safety risks; (vi) the patient has been previously treated with a medication or procedure selected from the group consisting of a topical corticosteroid, a topical calcineurin inhibitor, an anti-histamine, an emollient, a dermatological therapeutic, a systemic glucocorticoid, a non-steroidal systemic immunosuppressant, cyclosporine A, azathioprine, UV (ultraviolet) light therapy, and phototherapy; and (vii) the patient has a concomitant disease or disorder selected from the group consisting of food allergy, asthma, seasonal allergy, allergic rhinitis, house dust allergy, and allergic conjunctivitis; and (b) administering one or more doses of a therapeutically effective amount of an IL-4R inhibitor to the patient in need thereof. In one embodiment, the patient has moderate-to-severe AD and a history of inadequate response, intolerance or contraindication to a systemic therapy (e.g., Cyclosporine A, methotrexate, azathiosporine, etc.). In certain embodiments, the administration of the IL-4R inhibitor leads to a therapeutic effect selected from the group consisting of: (i) more than 30% reduction from baseline in EASI score by week 2 after administration of the first dose of the IL-4R inhibitor; (ii) more than 50% reduction from baseline in pruritus NRS; and (iii) a reduction from baseline in IGA score to achieve an IGA score of 0 or 1 by week 12 after administration of the first dose of the IL-4R inhibitor. In certain embodiments, the IL-4R inhibitor is administered in combination with a second therapeutic agent selected from the group consisting of a topical corticosteroid, a topical calcineurin inhibitor, an anti-histamine, an emollient, an anti-bacterial therapeutic, and a therapeutic agent for obstructive airway disease, a lung disorder and/or allergic reaction.

Interleukin-4 Receptor Inhibitors

The methods of the present invention comprise administering to a subject in need thereof a therapeutic composition comprising an interleukin-4 receptor (IL-4R) inhibitor. As used herein, an "IL-4R inhibitor" (also referred to herein as an "IL-4R inhibitor," an "IL-4Rα antagonist," an "IL-4R blocker," an "IL-4Rα blocker," etc.) is any agent which binds to or interacts with IL-4Rα or an IL-4R ligand, and inhibits or attenuates the normal biological signaling function a type 1 and/or a type 2 IL-4 receptor. Human IL-4Rα has the amino acid sequence of SEQ ID NO: 11. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R inhibitors that can be used in the methods of the present invention may function by blocking IL-4-mediated signaling, IL-13-mediated signaling, or both IL-4- and IL-13-mediated signaling. The IL-4R inhibitors of the present invention may thus prevent the interaction of IL-4 and/or IL-13 with a type 1 or type 2 receptor.

Non-limiting examples of categories of IL-4R inhibitors include IL-4 muteins (e.g., pitrakinra), small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Ra. As used herein, IL-4R inhibitors also include antigen-binding proteins that specifically bind IL-4 and/or IL-13.

Other non-limiting examples of suitable IL-4R inhibitors that can be used in the context of the present disclosure include, e.g., pitrakinra (AER-001; BAY-16-9996), aeroderm (AER-003), and the antibodies referred to and known in the art as dupilumab, AMG-317, CBP-201, MED19314, and MED12045.

Anti-IL-4Rα Antibodies and Antigen-Binding Fragments Thereof

According to certain exemplary embodiments of the present invention, the IL-4R inhibitor is an anti-IL-4Rα antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$—$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii)

$V_L$-$C_H$1; (ix) $V_L$-$C_H$2; (x) $V_L$-$C_H$3; (xi) $V_L$-$C_H$1-$C_H$2; (ii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present invention specifically bind IL-4Ra. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4Rα, as used in the context of the present invention, includes antibodies that bind IL-4Rα or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 1 nM, less than about 0.5 nM, less than about 0.25 nM, less than about 0.1 nM or less than about 0.05 nM, as measured in a surface plasmon resonance assay. An isolated antibody that specifically binds human IL-4Rα may, however, have cross-reactivity to other antigens, such as IL-4Rα molecules from other (non-human) species.

According to certain exemplary embodiments of the present invention, the IL-4R inhibitor is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693. In certain exemplary embodiments, the anti-IL-4Rα antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In some embodiments, the anti-IL-4R antibody or antigen-binding fragment thereof comprises an HCVR comprising SEQ ID NO: 1 and an LCVR comprising SEQ ID NO: 2. According to certain exemplary embodiments, the methods of the present invention comprise the use of the anti-IL-4R antibody comprising HCDR1-HCDR2-HCDR3-LCDR1-LCDR2-LCDR3 amino acid sequences of SEQ ID NOs: 3-4-5-6-7-8, or a bioequivalent thereof. In certain embodiments, the methods of the present invention comprise the use of an anti-IL-4R antibody, wherein the antibody comprises a heavy chain comprising the amino acid sequence of SEQ ID NO: 9. In some embodiments, the anti-IL-4R antibody comprises a light chain comprising the amino acid sequence of SEQ ID NO: 10. An exemplary antibody comprising a heavy chain comprising the amino acid sequence of SEQ ID NO: 9 and a light chain comprising the amino acid sequence of SEQ ID NO: 10 is the fully human anti-IL-4R antibody referred to and known in the art as "dupilumab". According to certain exemplary embodiments, the methods of the present invention comprise the use of dupilumab, or a bioequivalent thereof. The term "bioequivalent", as used herein, refers to anti-IL-4R antibodies or IL-4R-binding proteins or fragments thereof that are pharmaceutical equivalents or pharmaceutical alternatives whose rate and/or extent of absorption do not show a significant difference with that of dupilumab when administered at the same molar dose under similar experimental conditions, either single dose or multiple dose. In the context of the invention, the term refers to antigen-binding proteins that bind to IL-4R which do not have clinically meaningful differences with dupilumab in their safety, purity and/or potency.

Other anti-IL-4Rα antibodies that can be used in the context of the methods of the present invention include, e.g., the antibody referred to and known in the art as AMG317 (Corren et al., 2010, *Am J Respir Crit Care Med.*, 181(8): 788-796), MEDI 9314, CBP-201, or any of the anti-IL-4Rα antibodies as set forth in U.S. Pat. Nos. 7,186,809, 7,605,237, 7,638,606, 8,092,804, 8,679,487, 8,877,189, or WO2017/211319.

The anti-IL-4Rα antibodies used in the context of the methods of the present invention may have pH-dependent binding characteristics. For example, an anti-IL-4Rα antibody for use in the methods of the present invention may exhibit reduced binding to IL-4Rα at acidic pH as compared to neutral pH. Alternatively, an anti-IL-4Rα antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Pharmaceutical Compositions and Administration

The present invention includes methods which comprise administering an IL-4R inhibitor to a patient, wherein the IL-4R inhibitor is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient according to the methods of the present invention may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351). Specific exemplary doses of anti-IL4R antibodies and administration regimens involving the same that can be used in the context of the present invention are disclosed elsewhere herein.

Various delivery systems are known and can be used to administer the pharmaceutical composition comprising an IL-4R inhibitor, e.g., syringe, prefilled syringe, autoinjector, microinfuser, glass vial, encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In one embodiment, the syringe is a prefilled syringe. Such a prefilled syringe may be single-dose. In one embodiment, the pharmaceutical composition of the present invention can be delivered subcutaneously or intravenously with an autoinjector, wherein the autoinjector may comprise a prefilled syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable syringe, pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present invention are disclosed in, e.g., U.S. Pat. No. 8,945,559.

Administration Regimens

The present invention includes methods comprising administering to a subject an IL-4R inhibitor at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of an anti-IL-4R antibody, once a week dosing at an amount of about 25 mg, 50 mg, 150 mg, 200 mg, or 300 mg, is employed. In certain embodiments involving the administration of an anti-IL-4R antibody, once in 2 weeks dosing at an amount of about 25 mg, 50 mg, 150 mg, 200 mg, or 300 mg, is employed. In certain embodiments, a loading dose is administered prior to the weekly or biweekly dosing, wherein the loading dose comprises twice (2×) the amount of antibody administered in subsequent doses.

According to certain embodiments of the present invention, multiple doses of an IL-4R inhibitor may be administered to a subject over a defined time course. The methods according to this aspect of the invention comprise sequentially administering to a subject multiple doses of an IL-4R inhibitor. As used herein, "sequentially administering" means that each dose of IL-4R inhibitor is administered to the subject at a different point in time, e.g., on different days separated by a predetermined interval (e.g., hours, days, weeks or months). The present invention includes methods which comprise sequentially administering to the patient a single initial dose of an IL-4R inhibitor, followed by one or more secondary doses of the IL-4R inhibitor, and optionally followed by one or more tertiary doses of the IL-4R inhibitor.

The terms "initial dose," "secondary doses," and "tertiary doses," refer to the temporal sequence of administration of the IL-4R inhibitor. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of IL-4R inhibitor, but generally may differ from one another in terms of frequency of administration. In certain embodiments, however, the amount of IL-4R inhibitor contained in the initial, secondary and/or tertiary doses varies from one another (e.g., adjusted up or down as appropriate) during the course of treatment. In certain embodiments, the initial dose comprises a first amount of the antibody or antigen-binding fragment thereof and the one or more secondary doses each comprise a second amount of the antibody or antigen-binding fragment thereof. In some embodiments, the first amount of antibody or fragment thereof is 1.5×, 2×, 2.5×, 3×, 3.5×, 4×, or 5× the second amount of the antibody or antigen-binding fragment thereof. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an IL-4R inhibitor may be administered to a patient in need thereof at a loading dose of about 400 mg or about 600 mg followed by one or more maintenance doses of about 25 mg to about 400 mg. In one embodiment, the initial dose and the one or more secondary doses each include 10 mg to 600 mg of the IL-4R inhibitor, e.g., 100 mg to 400 mg of the IL-4R inhibitor, e.g., 10 mg, 25 mg, 50 mg, 100 mg, 150 mg, 200 mg, 250 mg, 300 mg, 400 mg or 500 mg of the IL-4R inhibitor.

In one exemplary embodiment of the present invention, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4R inhibitor which is administered to a patient prior to the administration of the very next dose in the sequence with no intervening doses.

The methods according to this aspect of the invention may comprise administering to a patient any number of secondary and/or tertiary doses of an IL-4R inhibitor. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 6 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the regimen.

The methods of the present invention, according to certain embodiments, comprise administering to the subject a topical corticosteroid (TCS) in combination with an IL-4R inhibitor (e.g., an anti-IL-4R antibody). As used herein, the expression "in combination with" means that the TCS is administered before, after, or concurrent with the IL-4R inhibitor. The term "in combination with" also includes sequential or concomitant administration of IL-4R inhibitor and TCS.

For example, when administered "before" the IL-4R inhibitor, the TCS may be administered more than 72 hours, about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the IL-4R inhibitor. When administered "after" the IL-4R inhibitor, the TCS may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, about 72 hours, or more than 72 hours after the administration of the IL-4R inhibitor. Administration "concurrent" with the IL-4R inhibitor means that the TCS is administered to the subject in a separate dosage form within less than 5 minutes (before, after, or at the same time) of administration of the IL-4R inhibitor, or administered to the subject as a single combined dosage formulation comprising both the TCS and the IL-4R inhibitor.

Dosage

The amount of IL-4R inhibitor (e.g., anti-IL-4R antibody) administered to a subject according to the methods of the present invention is, generally, a therapeutically effective amount. As used herein, the phrase "therapeutically effective amount" means an amount of IL-4R inhibitor that results in one or more of: (a) an improvement in one or more AD-associated parameters (as mentioned elsewhere herein); and/or (b) a detectable improvement in one or more symptoms or indicia of atopic dermatitis. In the context of the invention, a "therapeutically effective amount" includes an amount of IL-4R inhibitor that results in one or more of: (a) at least 60% decrease from baseline in EASI; (b) reduction in pruritus by at least 30%; (c) a decrease from the baseline of 2 points in IGA; (d) a decrease from the baseline of 24 points in NRS; (e) a decrease in skin colonization of *Staphylococcus aureus*; (f) a reduction in the level of an AD-associated biomarker such as IgE or TARC; (g) reduction in the use of TCS by at least 20%; and/or (h) a reduction in the number of flares or AD exacerbations.

In the case of an anti-IL-4R antibody, an immunologically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In certain embodiments, 10 mg, 25 mg, 50 mg, 75 mg, 150 mg, or 300 mg of an anti-IL-4R antibody is administered to a subject.

The amount of IL-4R inhibitor contained within the individual doses may be expressed in terms of milligrams of antibody per kilogram of subject body weight (i.e., mg/kg). For example, the IL-4R inhibitor may be administered to a subject at a dose of about 0.0001 to about 100 mg/kg of subject body weight.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Pharmacokinetics, Safety and Efficacy of Dupilumab in a Pediatric Population with Moderate-to-Severe or Severe AD: Results from a Phase 2a Clinical Trial This Example describes a phase 2a, multicenter, open-label, ascending-dose, sequential-cohort study (NCT02407756) which included adolescents (12-17 years) with moderate-to-severe AD and children (6-11 years) with severe AD, uncontrolled by topical medications. Patients received 2 mg/kg or 4 mg/kg single-dose subcutaneous dupilumab with 8 weeks follow-up, followed by 4 weekly 2 mg/kg or 4 mg/kg doses.

Study Objectives

The primary objective of the study was to characterize the safety and PK of dupilumab in pediatric patients with moderate-to-severe AD (for adolescents ≥12 to <18 years of age) or severe AD (for children ≥6 to <12 years of age). The secondary objective of the study was to explore the immunogenicity and efficacy of dupilumab in pediatric patients with moderate-to-severe AD (for adolescents ≥12 to <18 years of age) or severe AD (for children ≥6 to <12 years of age).

Study Design

This was conducted as a phase 2a, multicenter, open-label, ascending dose, sequential cohort study investigating the safety, tolerability, pharmacokinetics (PK), immunogenicity, and efficacy of single-dose and repeat-doses of subcutaneously administered (SC) dupilumab in pediatric patients with moderate-to-severe AD (for adolescents ≥12 to <18 years of age) or severe AD (for children ≥2 to <12 years of age) that was not adequately controlled by topical treatments.

Two sequential ascending SC dose cohorts were planned: dose cohort 1 (2 mg/kg) and dose cohort 2 (4 mg/kg) up to a maximum dose of 300 mg. Within each dose cohort, approximately 36 to 40 patients were planned to be enrolled in 2 age subsets: subset A (adolescents ≥12 to <18 years of age) and subset B (children ≥6 to <12 years of age). Enrollment and study dosing started with cohort 1A (2 mg/kg, adolescent age subset) and proceeded in sequence to cohort 1B (2 mg/kg, children ≥6 to <12 years of age subset), cohort 2A (4 mg/kg, adolescent age subset), and cohort 2B (4 mg/kg, children ≥6 to <12 years of age subset); a safety review of data from the previous cohort(s) was performed before proceeding to the next cohort.

The study consisted of a screening period (day −35 to day −1), a baseline visit, Part A (including a single-dose treatment followed by an 8-week semi-dense PK sampling period), and Part B (including a 4-week repeat-dose treatment period [4 weekly doses] followed by an 8-week follow-up period).

Patients received concomitant medications (except for prohibited medications) as needed, while continuing study treatment Frequency of use and type of treatment were documented. If medically necessary, rescue treatments were provided to study patients. The rescue treatments included more intensive topical treatment (medications and/or procedures) before escalating rescue to systemic medications, if medically appropriate. Patients who received rescue with systemic corticosteroids or systemic non-steroid immunosuppressive drugs (e.g., cyclosporine, methotrexate, mycophenolate-mofetil, azathioprine, etc.) during Part A (the single-dose treatment and 8-week semi-dense PK sampling period) needed to have such rescue treatment discontinued at least 2 weeks prior to start of Part B (i.e., prior to the start of administration of repeat-doses of study treatment); patients who received any of these rescue treatments during the repeat-dose treatment period were discontinued from study drug.

Dose Escalation: Dosing started with cohort 1A. Proceeding to the next cohort (1B) occurred once all of the initial 8 patients enrolled in cohort 1A had been observed for at least 2 weeks, had completed the week 2 (day 15) safety assessments, and the data had been reviewed. Dosing escalated to cohort 2A once all of the initial 20 patients enrolled in cohorts 1A and/or 1B had been observed for at least 2 weeks, had completed the week 2 (day 15) safety assessments, and the data had been reviewed. Proceeding to the next cohort (2B) occurred once all of the initial 8 patients enrolled in cohort 2A had been observed for at least 2 weeks, had completed the week 2 (day 15) safety assessments, and the data had been reviewed.

Study Population

The study population included pediatric patients with moderate-to-severe AD (for adolescents aged ≥12 to <18 years at the time of baseline) or severe AD (for children aged ≥6 to <12 years at the time of baseline) that was not adequately controlled with topical medications.

Inclusion Criteria: A patient had to meet the following criteria to be eligible for inclusion in the study: (1) Male or female ≥6 to <18 years of age at the time of baseline; (2) Diagnosis of AD according to the American Academy of Dermatology criteria (Eichenfield et al 2014, J. Am. Acad. Dermatol. 70: 338-51) established at least 1 year before screening; (3) Patients with documented recent history (within 6 months before the screening visit) of inadequate response to a sufficient course of outpatient treatment with topical AD medication(s), or for whom topical AD therapies were otherwise inadvisable (e.g., because of side effects or safety risks). NOTE: For the purpose of this disclosure, inadequate response represented failure to achieve and maintain remission or a low disease activity state (comparable to Investigator's Global Assessment [IGA] 0=clear to 2=mild) despite treatment for at least 28 days with a regimen of TCS of medium to high potency (t TCI as appropriate). Side effects or safety risks that may outweigh the potential treatment benefits included intolerance to treatment, hypersensitivity reactions, significant skin atrophy, and side effects related to systemic absorption. Acceptable documentation included contemporaneous chart notes that recorded TCS with or without TCI prescription and treatment outcome, or investigator documentation based on communication with patient's treating physician. If documentation was inadequate, potential patients may have been re-screened after patients had been shown to fail mid-to-higher potency TCS (±TCI) for the prescribed length of treatment stated above.(4) IGA at baseline: a. IGA=3 or 4 in adolescents ≥12 to <18 year of age; b. IGA=4 in children ≥6 to <12 years of age; (5) At least 10% body surface area (BSA) affected by AD lesions at baseline. Note: This inclusion criterion was modified from the original criterion to clarify that the BSA affected by AD should be based on the assessment performed at baseline. (6) Willing and able to comply with clinic visits and study-related procedures; (7) With a parent/caregiver or legal guardian, able to understand the study requirements (8) Parent or legal guardian must have provided signed informed consent. Patients 27 years of age (or above an age determined by the IRB/IEC and in accordance with the local regulations and requirements) must have also provided informed assent to enroll in the study, and must have signed and dated either a separate IAF or the ICF; and (9) Parent or legal guardian/patient, as appropriate, must have been able to understand and complete study-related questionnaires.

Exclusion Criteria: A patient who met any of the following criteria was excluded from the study: (1) Treatment with an investigational drug within 8 weeks or within 5 half-lives (if known), whichever was longer, before the baseline visit: (2) The following treatments within 2 weeks before the baseline visit a. Systemic corticosteroids b. Immunosuppressive/immunomodulating drugs (e.g., cyclosporine, mycophenolate mofetil, interferon-gamma, Janus kinase inhibitors, azathioprine or methotrexate) c. Phototherapy for AD: (3) Treatment with biologics as follows: a. Any cell-depleting agents including, but not limited to, rituximab within 6 months before the baseline visit or until lymphocyte returned to normal, whichever was longer b. Other biologics within 5 half-lives (if known) or 4 months before the baseline visit, whichever was longer; (4) Planned or anticipated use of any prohibited medications and procedures during study treatment; (5) Treatment with a live (attenuated) vaccine within 3 months before the baseline visit; (6) Active chronic or acute infection requiring treatment with systemic antibiotics, antivirals, antiprotozoals, or antifungals within 4 weeks before the baseline visit, or superficial skin infections within 1 week before the baseline visit; (7) Known or suspected immunodeficiency, including history of invasive opportunistic infections (e.g., tuberculosis, histoplasmosis, listeriosis, coccidioidomycosis, pneumocystosis, aspergillosis) despite infection resolution, or otherwise recurrent infections of abnormal frequency or prolonged duration suggesting an immune compromised status; (8) Known history of human immunodeficiency virus infection; (9) Active infection with hepatitis B or C at screening, or a prior history of active infection with hepatitis B or C, as reported at time of screening; (10) Persistent (confirmed by repeated tests 22 weeks apart) elevated transaminases (alanine aminotransferase [ALT] and/or aspartate aminotransferase [AST]) more than 3 times the upper limit of normal (ULN) during the screening period; (11) At baseline, presence of any conditions listed as criteria for study treatment discontinuation; (12) Presence of skin comorbidities that may have interfered with study assessments; (13) History of malignancy within 5 years before the baseline visit, except completely treated in situ carcinoma of the cervix and completely treated and resolved non-metastatic squamous or basal cell carcinoma of the skin; (14) History of clinical endoparasitosis (i.e., helminth infection) within 12 months before the baseline visit, or high risk of helminth infection, such as residence within or recent travel (within 12 months before the baseline visit) to areas endemic for endoparasitoses, where the circumstances were consistent with parasite exposure (e.g., extended stay, rural or slum areas, lack of running water, consumption of uncooked, undercooked, or otherwise potentially contaminated food, close contact with carriers and vectors, etc.), unless subsequent medical assessments (e.g., stool exam, blood tests, etc.) ruled out the possibility of parasite infection/infestation; (15) History of alcohol or drug abuse within 2 years before the screening visit; (16) Severe concomitant illness(es) that would have adversely affected the patient's participation in the study. Examples included, but were not limited to, patients with short life expectancy, patients with uncontrolled diabetes (hemoglobin A1c 29%), patients with cardiovascular conditions (e.g., stage III or IV cardiac failure according to the New York Heart Association classification), severe renal conditions (e.g., patients on dialysis), hepatobiliary conditions (e.g., Child-Pugh class B or C), neurological conditions (e.g., demyelinating diseases), active major autoimmune diseases (e.g., lupus, inflammatory bowel disease, rheumatoid arthritis, etc.), and other severe endocrinological, gastrointestinal, metabolic, pulmonary, or lymphatic diseases; (17) Any other medical or psychological condition including relevant laboratory abnormalities at screening that suggested a new and/or insufficiently understood disease, may have presented an unreasonable risk to the study patient as a result of his/her participation in this clinical trial, may have made patient's participation unreliable, or may have interfered with study assessments; (18) Planned major surgical procedure during the patient's participation in this study; (19) Patient was a member of the investigational team or his/her immediate family; and (20) Female patients who were pregnant, breastfeeding, or planning to become pregnant or breastfeed during the study, or female patients of childbearing potential, who were unwilling to use adequate methods of contraception throughout the duration of the study and for 120 days after the last dose of study drug.

Study Treatments

Sterile dupilumab drug product 150 mg/mL was provided in an aqueous buffered vehicle, pH 5.0. It was supplied in a 5 mL vial containing 2.5 mL (150 mg/mL) with a withdrawable volume of 2.0 mL or 300 mg of dupilumab. Study drug was administered SC by the investigator or other qualified study personnel at the following dose and dosing schedules:

For dose cohort 1: 2 mg/kg at day 1 as a single dose in Part A, then weekly at day 1 to week 3 in Part B as repeat doses For dose cohort 2: 4 mg/kg at day 1 as a single dose in Part A, then weekly at day 1 to week 3 in Part B as repeat doses Subcutaneous injection sites of the study drug were to be alternated among the different quadrants of the abdomen (avoiding navel and waist areas), upper thighs, and upper arms so that the same site was not injected for 2 consecutive weeks. To allow for adequate assessment of possible injection site reactions, study drug was to be administered only into areas of normal-looking skin.

Primary and Secondary Endpoints

The primary objective was characterizing the PK profiles of dupilumab in pediatric AD patients aged ≥6 to <18 years. The secondary endpoints were:

Incidence of TEAEs

Percent change from baseline in Eczema Area and Severity Index (EASI)

Percent change from baseline in SCORing Atopic Dermatitis (SCORAD) score

Percent change from baseline in Pruritus Numerical Rating Scale (NRS)

Percentage of patients with an IGA score of 0 or 1

Change from baseline in % BSA affected by AD

Study Variables and Procedures

Safety and tolerability was assessed by vital signs, physical examinations, clinical laboratory tests, and clinical evaluations. Patients were asked to monitor all adverse events (AEs) experienced from the time of informed consent/assent until their last study visit. Serum samples were collected for assay of dupilumab levels, and PK parameters were calculated using the dupilumab concentration data. Serum samples were collected for assay of ADA, and exploratory analyses. Efficacy was assessed during the study at specified clinic visits using the Pruritus NRS, SCORAD, and EASI that measure the extent and severity of AD, and the IGA that rates the overall severity of AD.

Results
(A) Baseline Disease Characteristics

This study enrolled adolescent patients aged ≥12 to <18 years with moderate-to-severe AD (baseline IGA score of 3 or 4) and children aged ≥6 to <12 years with severe AD (baseline GA score of 4; see inclusion criteria for each age group). Therefore, disease characteristics at baseline differed between the two age groups.

Adolescent Patients Aged ≥12 to <18 Years: The proportion of adolescent patients diagnosed with AD within specified age ranges was generally similar between the dose cohorts, with the majority of patients in each dose cohort diagnosed before the age of 5 (Table 1). The mean duration of AD was also similar between the dos cohorts. As expected, patients in the older age subsets within each dos cohort had longer duration of AD than younger patients. Mean baseline values for all AD assessments were consistent with moderate-to-severe AD. Differences in mean EASI score at baseline, mean pruritus NRS score, mean BSA and SCORAD score were minor and consistent with that expected in non-randomized groups (Table 1). Overall, the baseline disease characteristics were comparable between the 2 dose cohorts. IDC-2

TABLE 1

Summary of Baseline Disease Characteristics for Adolescent Patients Aged ≥12 to <18 Years

|  | 2 mg/kg SC (N = 20) | 4 mg/kg SC (N = 20) | Total (N = 40) |
|---|---|---|---|
| Chronic AD Diagnosis Age: |  |  |  |
| Before 5 years of age | 16 (80%) | 18 (90%) | 34 (85%) |
| Between 5 and 9 years of age | 3 (15%) | 2 (10%) | 5 (12.5%) |
| Between 10 and 17 years of age | 1 (5%) | 0 | 1 (2.5%) |
| Duration of AD (years) Mean (SD) | 11.8 (4.21) | 12.5 (2.28) | 12.2 (3.36) |
| EASI score Mean (SD) | 34.8 (17.00) | 28.6 (14.70) | 31.7 (16.00) |
| Number n (%) of patients with IGA score 3 | 8 (40%) | 11 (55%) | 19 (47.5%) |
| Number n (%) of patients with IGA score 4 | 12 (60%) | 9 (45%) | 21 (52.5%) |
| Pruritus NRS Mean (SD) | 6.1 (2.47) | 6.9 (2.21) | 6.5 (2.34) |
| Number n (%) of patients with Pruritus NRS ≥ 3 | 18 (90%) | 19 (95%) | 37 (92.5%) |
| Number n (%) of patients with Pruritus NRS ≥ 4 | 15 (75%) | 18 (90%) | 33 (82.5%) |
| BSA Mean (SD) | 52.2 (24.78) | 45.9 (25.34) | 49 (24.94) |
| SCORAD Mean (SD) | 68.0 (13.19) | 63.0 (14.43) | 65.5 (13.88) |

BSA, body surface area;
EASI, Eczema Area Severity Index;
IGA, Investigator's Global Assessment;
NRS, numerical rating scale;
SAF, safety analysis set;
SC, subcutaneous;
SCORAD, Scoring Atopic Dermatitis;
SD, standard deviation Patients aged ≥6 to <12 years: The proportion of patients aged ≥6 to <12 years diagnosed with AD within specified age ranges was generally similar between the dose cohorts, with the majority of patients in each dose cohort diagnosed before the age of 5 (Table 2). The mean duration of AD was also similar between the dose cohorts. As expected, patients in the older age subsets within each dose cohort had a longer duration of AD than younger patients. Mean baseline values for all AD assessments were consistent with severe/moderate AD. Differences in mean EASI score at baseline, mean pruritus NRS score, mean BSA and SCORAD score were minor and consistent with that expected in non-randomized groups (Table 2). Overall, the baseline disease characteristics were comparable between the 2 dose cohorts.

TABLE 2

Summary of Baseline Disease Characteristics - Children >=6 to <12 Years of Age

|  | 2 mg/kg SC (N = 18) | 4 mg/kg SC (N = 19) | Total (N = 37) |
|---|---|---|---|
| Chronic AD Diagnosis Age |  |  |  |
| Before 5 years of age | 16 (88.9%) | 19 (100%) | 35 (94.6%) |
| Between 5 and 9 years of age | 2 (11.1%) | 0 | 2 (5.4%) |
| Duration of AD (years) Mean (SD) | 6.8 (2.46) | 7.4 (2.24) | 7.1 (2.33) |
| EASI Mean (SD) | 32.9 (15.53) | 38.8 (18.64) | 35.9 (17.22) |
| Number n (%) of patients with IGA score 3 | 1 (5.6%) | 0 | 1 (2.7%) |

TABLE 2-continued

Summary of Baseline Disease Characteristics - Children >=6 to <12 Years of Age

|  | 2 mg/kg SC (N = 18) | 4 mg/kg SC (N = 19) | Total (N = 37) |
|---|---|---|---|
| Number n (%) of patients with IGA score 4 | 17 (94.4%) | 19 (100%) | 36 (97.3%) |
| Pruritus NRS Mean (SD) | 6.4 (2.23) | 6.7 (2.35) | 6.6 (2.27) |
| Number n (%) of patients with Pruritus NRS ≥ 3 | 18 (100%) | 18 (94.7%) | 36 (97.3%) |
| Number n (%) of patients with Pruritus NRS ≥ 4 | 18 (100%) | 17 (89.5%) | 35 (94.6%) |
| BSA Mean (SD) | 59.0 (22.49) | 62.3 (30.34) | 60.7 (26.49) |
| SCORAD Mean (SD) | 66.4 (13.06) | 72.7 (12.96) | 69.7 (13.22) |

BSA, body surface area;
EASI, Eczema Area Severity Index;
IGA, Investigator's Global Assessment;
NRS, numerical rating scale;
SAF, safety analysis set;
SC, subcutaneous;
SCORAD, Scoring Atopic Dermatitis;
SD, standard deviation (B) Medical history Medical history was assessed using a general questionnaire, and specific atopic disease medical history was collected using a targeted questionnaire that elicited extensive atopic history.

Adolescent Patients Aged ≥12 to <18 Years: All adolescent patients (100%) had at least 1 medical history finding using the general questionnaire. The most common non-AD MedDRA PTs reported in ≥30% of patients overall were Food Allergy (45.0%), Asthma (45.0%), House Dust Allergy (35.0%), Seasonal Allergy (35.0%), Allergic Rhinitis (35.0%), and Allergy to Animal (30.0%). A history of allergic conjunctivitis was present in 11 (27.5%) patients.

Based on the specific atopic disease questionnaire, the proportion of patients with a family history of atopic/allergic conditions was similar between the two dose cohorts. The most common atopic/allergic condition in patient family history was AD (37.5% overall). The most common atopic/allergic condition in patient family history in the 2 mg/kg dose cohort was AD (50.0%) whereas in the 4 mg/kg dose cohort it was Other Allergies (30.0%). The most common current atopic/allergic condition other than AD was Other Allergies (60.0% overall; 55.0% in the 2 mg/kg dose cohort and 65.0% in the 4 mg/kg dose cohort). Overall, 30.0% of all patients indicated a current history of Allergic Conjunctivitis and 37.5% had a current history of Asthma, both of which were reported in higher proportions of patients in the 4 mg/kg dose cohort. Five percent of all patients had a currently resolved atopic/allergic condition. The most common currently resolved atopic/allergic condition was Asthma, which was reported at a similar frequency in both dose cohorts.

Patients ≥6 to <12 Years of Age: All patients aged ≥6 to <12 years (100%) had at least 1 medical history finding using the general questionnaire. The most common non-AD MedDRA PTs reported in ≥30% of patients overall were Food Allergy (67.6%), Allergic Rhinitis (51.4%), House Dust Allergy (48.6%), Asthma (43.2%), and Seasonal Allergy (35.1%). A history of allergic conjunctivitis was present in 9 (24.3%) patients. In general, medical history was similar between the dose cohorts. Differences between dose cohorts included a higher incidence of Food Allergy (73.7%, 61.1%), Milk Allergy (15.8%, 5.6%), and Allergic Conjunctivitis (31.6%, 16.7%) in the 4 mg/kg dose cohort than in the 2 mg/kg dose cohort, respectively. The incidence of Allergy to Animal (38.9%, 5.3%), Mycotic Allergy (16.7%, 5.3%), and Allergic Rhinitis (61.1%, 42.1%) were higher in the 2 mg/kg dose cohort than in the 4 mg/kg dose cohort, respectively.

Based on the specific atopic disease questionnaire, the proportion of patients with a family history of atopic/allergic conditions was higher in the 4 mg/kg dose cohort than in the 2 mg/kg dose cohort. The most common atopic/allergic condition in patient family history was AD (32.4% overall). The most common atopic/allergic condition in patient family history in the 2 mg/kg dose cohort was Allergic Rhinitis (33.3%) whereas in the 4 mg/kg dose cohort it was AD (36.8%). The most common current atopic/allergic conditions other than AD were Other Allergies and Food Allergy (64.9% overall each). The incidence of current Food Allergy was higher in the 4 mg/kg dose cohort (73.7%) than in the 2 mg/kg dose cohort (55.6%). Overall, 21.6% of all patients indicated a current history of Allergic Conjunctivitis and 43.2% had a current history of Asthma, both of which were reported in higher proportions of patients in the 4 mg/kg dose cohort.

(C) Previous Medications/Procedures

Prior medications/procedures were defined as medications taken or procedures performed prior to the first administration of study drug.

Adolescent Patients Aged ≥12 to <18 Years: All adolescent patients received at least 1 prior medication. The most commonly used (≥50% of all patients) prior medications by therapeutic class were Corticosteroids Dermatological Preparations (97.5%), Antihistamines for Systemic Use (67.5%), and Other Dermatological Preparations (67.5%). Prior medication use was generally similar between the 2 dose cohorts. Dermatological preparations of corticosteroids included potent (Group III; 87.5% patients overall), weak (Group I; 35.0% patients overall), moderately potent (Group II; 27.5% patients overall), and very potent (Group IV; 12.5%). A total of 7 (17.5%) adolescent patients had a history of systemic glucocorticoid use. Thirteen patients reported prior use of a non-steroidal systemic immunosuppressant, which included cyclosporine and azathioprine. Nine (22.5%) adolescent patients reported at least 1 prior procedure. The most commonly reported prior procedures in >1 patient were ultraviolet (UV) light therapy (7.5% patients overall) and phototherapy (5.0% patients overall).

Patients ≥6 to <12 Years of Age: All patients aged ≥6 to <12 years received at least 1 prior medication. The most commonly used (≥50% of all patients) prior medications by therapeutic class were Corticosteroids Dermatological Preparations (97.3%), Antihistamines for Systemic Use (91.9%), Emollients and Protectives (70.3%), and Other Dermatological Preparations (70.3%). Prior medication use was generally similar between the 2 dose cohorts. Dermatological preparations of corticosteroids included potent (Group III; 83.8% patients overall), moderately potent (Group II; 43.2% patients overall), weak (Group I; 29.7% patients overall), and very potent (Group IV; 10.8%). Prior systemic glucocorticoid use was reported by 11 (29.7%) patients. Ten patients reported prior use of a non-steroidal systemic immunosuppressant, including cyclosporine and azathioprine. Seven (18.9%) patients reported at least 1 prior procedure. Prior procedures reported by >1 patient overall included UV light therapy (10.8% patients overall) and phototherapy (5.4% patients overall).

(D) Concomitant Medications and Procedures

Adolescent Patients Aged ≥12 to <18 Years: Most adolescent patients (97.5%) received at least 1 concomitant medication during the entire Study. The most commonly (≥25% patients overall) used concomitant medications by therapeutic class throughout the entire study were Corticosteroids Dermatological Preparations (75.0%), Antihistamines for Systemic Use (67.5%), Emollients and Protectives (45.0%), Other Dermatological Preparations (42.5%), and Drugs for Obstructive Airway Diseases (27.5%). Overall, 77.5% of patients used concomitant treatments for AD during the study, including 85.0% of patients in the 2 mg/kg dose cohort and 70.0% of patients in the 4 mg/kg dose cohort. The use of any TCS was higher in the 2 mg/kg dose cohort than in the 4 mg/kg dose cohort. The most commonly used TCS in both dose cohorts was potent (Group III) TCS. The use of TCI was also higher in the 2 mg/kg dose cohort than in the 4 mg/kg dose cohort. Tacrolimus was the most commonly used TCI in both dose cohorts. The number of adolescent patients who used any concomitant AD medication was higher during the Part A period (31 [77.5%]) than during the Part B period (11 [27.5%]). TCS and TCI use in adolescents was higher for both dose cohorts during the Part A period compared to the Part B period. Systemic corticosteroid use was low and comparable between Part A and Part B.

Patients ≥6 to <12 Years of Age: Most patients aged ≥6 to <12 years (97.3%) received at least 1 concomitant medication during the entire study. The most commonly (≥25% patients overall) used concomitant medications by therapeutic class throughout the entire study were Antihistamines for Systemic Use (89.2%), Corticosteroids Dermatological Preparations (89.2%), Emollients and Protectives (75.7%), Other Dermatological Preparations (48.6%), Drugs for Obstructive Airway Diseases (40.5%) which may represent an overlap with asthma as a comorbidity, and Antibacterials for Systemic Use (27.0%). Overall, 91.9% of patients aged ≥6 to <12 years used concomitant treatments for AD during the study, including 88.9% of patients in the 2 mg/kg dose cohort and 94.7% of patients in the 4 mg/kg dose cohort. The use of any TCS was similar between the dose cohorts, and the most commonly used TCS in both dose cohorts was potent (Group III) TCS. The use of TCI was higher in the 2 mg/kg dose cohort than in the 4 mg/kg dose cohort. Tacrolimus was the most commonly used TCI in both dose cohorts. The number of patients ≥6 to <12 years of age who required the use of any concomitant AD medication was higher during the Part A period (33 [89.2%]) than during the Part B period (10 [27%]). The use of TCS and TCI was also higher during the Part A period than during the Part B period for both dose cohorts. No systemic immunosuppressant use was required during either Part A or Part B in the ≥6 to <12 years age group.

(E) Efficacy 40 adolescents/38 children (mean Eczema Area and Severity Index [EASI]±SD=31.7±16.00/35.9±17.22) were enrolled; 22.5% adolescents/16.2% children did not respond to a1 previous systemic treatment. The pharmacokinetic profile of dupilumab was similar to adults (target-mediated drug disposition). No new safety signals were detected compared with adults.

In the adolescent patients group, dupilumab administered as a single dose of either 2 mg/kg or 4 mg/kg induced significant and rapid reduction of disease activity in patients at week 2 (34% and 51% reduction in EASI score from baseline for 2 mg/kg and 4 mg/kg doses respectively). Repeated weekly doses of dupilumab led to a further improvement in disease severity in patients in both dose cohorts. At Week 12, in adolescent 2 mg/4 mg cohorts, baseline EASI significantly improved by 66.4%/69.7%, and peak pruritus Numerical Rating Scale (NRS) by 30.8%/37.6%; 10%/35% achieved an Investigator Global Assessment (IGA) 0-1.

Dupilumab administered as a single dose of either 2 mg/kg or 4 mg/kg induced significant and rapid reduction of disease activity in patients at week 2 (37% and 33% reduction in EASI score from baseline for 2 mg/kg and 4 mg/kg doses, respectively). Repeated weekly doses of dupilumab led to a further improvement in disease severity in patients in both dose cohorts. At Week 12 in children 2 mg/4 mg cohorts, baseline EASI significantly improved by 76.2%/63.4% and peak pruritus NRS by 41.6%/39.6%; 16.7%/21.1% achieved IGA 0-1.

Overall, both dose regimens studied showed significant clinical benefit in both pediatric age groups. Single doses of 2 mg/kg and 4 mg/kg dupilumab led to a rapid reduction in signs and symptoms of AD in both age groups. Repeated weekly doses provided an improved and more sustained response than a single dose in both age groups. This clinical response was seen in patients with high disease activity at baseline and who had failed all approved available therapies for their disease.

Conclusions

Dupilumab administered as single and repeated weekly doses of 2 mg/kg and 4 mg/kg for 4 weeks was generally safe and well tolerated in both pediatric age groups included in this study. In pediatric patients with AD, the dupilumab pharmacokinetic profile was consistent with adults; dupilumab provided clinical benefit (including itch improvement) faster than rates observed in adult clinical trials with a similar safety profile.

Example 2: Clinical Study to Investigate Safety and Efficacy of Dupilumab Monotherapy in Patients ≥12 Years to <18 Years of Age with Moderate-to-Severe Atopic Dermatitis (AD)

Study Objectives

The primary objective of the study was to demonstrate the efficacy of dupilumab as a monotherapy in patients ≥12 years to <18 years of age with moderate-to-severe atopic dermatitis (AD). The secondary objective of the study was to assess the safety of dupilumab as a monotherapy in patients ≥12 years to <18 years of age with moderate-to-severe AD.

Study Design

This was a randomized, double-blind, placebo-controlled, parallel-group study to investigate the efficacy and safety of dupilumab monotherapy in pediatric patients with moderate-to-severe AD. The study population included patients ≥12 years to <18 years of age with moderate-to-severe AD whose disease was not adequately controlled with topical medications or for whom topical treatment was medically inadvisable (e.g., intolerance, other important side effects or safety risks). Patients were randomized to one of the following treatment groups:

Dupilumab every 2 weeks (Q2W) treatment group: 200 mg Q2W (patients <60 kg) or 300 mg Q2W (patients ≥60 kg)

Dupilumab every 4 weeks (Q4W) treatment group: 300 mg Q4W, irrespective of weight Placebo group The study consisted of the following 3 periods: screening of up to 5 weeks, treatment period of 16 weeks, and follow-up of 12 weeks.

After the parents or legal guardians/patients provided informed consent and informed assent (as appropriate), the patients were assessed for study eligibility at the screening visit. During the screening period, systemic and topical treatments for AD were washed out, as applicable, according to the eligibility requirements. Patients were rescreened once if they failed the screening evaluation for reasons related to incidental transitory conditions, unless the reason for the screen failure was related to failing the disease severity inclusion criteria. Patients were required to apply moisturizers twice daily for at least 7 days before randomization and continue throughout the study.

Patients who met eligibility criteria at baseline underwent day 1/baseline assessments and were randomized in a 1:1:1 ratio stratified by baseline weight group (<60 kg and ≥60 kg) and baseline disease severity (moderate [Investigator's Global Assessment (IGA=3)] vs. severe [IGA=4] AD) as follows: Dupilumab Q2W treatment group: Patients with baseline weight <60 kg received Q2W subcutaneous (SC) injections of 200 mg dupilumab following a loading dose of 400 mg on day 1. Patients with baseline weight ≥60 kg received Q2W SC injections of 300 mg dupilumab following a loading dose of 600 mg on day 1. Dupilumab Q4W treatment group: Patients received Q4W SC injections of 300 mg dupilumab following a loading dose of 600 mg on day 1. Placebo treatment group: Patients received placebo matching dupilumab Q2W (including doubling the amount of placebo on day 1 to match the loading dose). In order to maintain blinding for the study, patients in the <60 kg weight stratum received, in a 1:1 ratio, either placebo matching 200 mg dupilumab (including doubling the amount of placebo on day 1 to match the loading dose) or placebo matching 300 mg dupilumab (including doubling the amount of placebo on day 1 to match the loading dose). In the ≥60 kg weight stratum, the patients randomized to the placebo group received placebo matching 300 mg dupilumab (including doubling the amount of placebo on day 1 to match the loading dose).

In order to maintain blinding, all patients received an injection Q2W from day 1 to week 14. Patients received placebo injection at the weeks dupilumab was not given.

The duration of the study for each patient was approximately 28 weeks, excluding the screening period. During the treatment period, patients had weekly in-clinic visits through week 4, then every 4 weeks in-clinic visits through week 16, with weekly telephone visits in between in-clinic visits. Patients and/or parents/caregivers (as deemed appropriate based on age of patient) were trained on injecting study drug during in-clinic visit 2 (day 1) to visit 6 (week 4). During weeks in which no in-clinic visit was scheduled, patients either self-injected study drug or the parent/caregiver administered study drug to the patient. In case patients did not want to self-inject and the parent/caregiver did not want to administer study drug to patient, patients had the clinic staff administer all the study drug injections in the clinic. Safety, laboratory, and clinical assessments were performed at specified clinic visits. The end of treatment period visit occurred at week 16, two weeks after the last dose of study drug. The co-primary endpoints were assessed at this visit.

Study Population

The study population included pediatric patients (aged ≥12 to <18 years at the time of baseline) who had moderate-to-severe AD that was not adequately controlled with topical AD medications or for whom topical treatment was medically inadvisable (e.g., intolerance, other important side effects or safety risks).

Inclusion Criteria: A patient had to meet the following criteria to be eligible for inclusion in the study:

1) Male or female ≥12 to <18 years of age at time of screening visit
2) Diagnosis of AD according to the American Academy of Dermatology consensus criteria (Eichenfield et al 2014, J. Am. Acad. Dermatol. 70: 338-51) at screening visit
3) Chronic AD diagnosed at least 1 year prior to the screening visit
4) IGA≥3 at screening and baseline visits
5) EASI≥16 at the screening and baseline visits.
6) Baseline Pruritus Numerical Rating Scale (NRS) average score for maximum itch intensity ≥4
   NOTE: Baseline Pruritus NRS average score for maximum itch intensity is determined based on the average of daily NRS scores for maximum itch intensity (the daily score ranges from 0 to 10) during the 7 days immediately preceding randomization. A minimum of 4 daily scores out of the 7 days is required to calculate the baseline average score. For patients who do not have at least 4 daily scores reported during the 7 days immediately preceding the planned randomization date, randomization should be postponed until this requirement is met, but without exceeding the 35-day maximum duration for screening.
7) ≥10% body surface area (BSA) of AD involvement at the screening and baseline visits
8) With documented recent history (within 6 months before the screening visit) of inadequate response to topical AD medication(s) or for whom topical treatments is medically inadvisable (e.g., intolerance, because of important side effects or safety risks).
   NOTE:
   Inadequate response is defined as failure to achieve and maintain remission or a low disease activity state (comparable to IGA 0=clear to 2=mild) despite treatment with a daily regimen of TCS of medium to higher potency (±TCI as appropriate), applied for at least 28 days or for the maximum duration recommended by the product prescribing information (e.g., 14 days for super-potent TCS), whichever is shorter.
   Patients with documented systemic treatment (systemic immunosuppressant drugs like cyclosporine, methotrexate, corticosteroids etc.) for AD in the past 6 months are also considered as inadequate responders to topical treatments and are potentially eligible for treatment with dupilumab after appropriate washout.

Important side effects or safety risks are those that outweigh the potential treatment benefits and include intolerance to treatment, hypersensitivity reactions, significant skin atrophy, and systemic effects, as assessed by the investigator or by the patient's treating physician.

Acceptable documentation includes contemporaneous chart notes that record topical medication prescription and treatment outcome, or investigator documentation based on communication with the patient's treating physician. If documentation is inadequate, potential patients may be offered a course of treatment with a daily regimen of TCS of medium or higher potency (±TCI as appropriate), applied for at least 28 days during the screening period, or for the maximum duration recommended by the product prescribing information, whichever is shorter. Patients who demonstrate inadequate response during this period, as defined above, will be eligible for inclusion in the study following appropriate washout.

9) Has applied a stable dose of topical emollient (moisturizer) twice daily for at least the 7 consecutive days immediately before the baseline visit 10) Wiling and able to comply with all clinic visits and study-related procedures 11) Able to understand and complete study-related questionnaires 12) Parent or legal guardian must provide signed informed consent. Patients must also provide separate informed assent to enroll in the study, and sign and date either a separate informed assent form (IAF) or the informed consent form (ICF) signed by the parent/legal guardian (as appropriate based on local regulations and requirements).

Exclusion Criteria: A patient who met any of the following criteria was excluded from the study: 1. Participation in a prior dupilumab clinical study 2. Treatment with a systemic investigational drug before the baseline visit 3. Treatment with a topical investigational agent within 4 weeks or within 5 half-lives (if known), whichever is longer, before the baseline visit 4. Treatment with TCS or TCI within 2 weeks before the baseline visit (patients may be rescreened) 5. Having used any of the following treatments within 4 weeks before the baseline visit, or any condition that, in the opinion of the investigator, is likely to require such treatment(s) during the first 4 weeks of study treatment: a. Immunosuppressive/immunomodulating drugs (e.g., systemic corticosteroids, cyclosporine, mycophenolate-mofetil, interferon gamma, Janus kinase inhibitors, azathioprine, methotrexate, etc.) b. Phototherapy for AD 6. Treatment with biologics, as follows: a. Any cell-depleting agents including but not limited to rituximab: within 6 months before the baseline visit, or until lymphocyte and CD 19+ lymphocyte count returns to normal, whichever is longer b. Other biologics: within 5 half-lives (if known) or 16 weeks before the baseline visit, whichever is longer 7. Treatment with a live (attenuated) vaccine within 4 weeks before the baseline visit NOTE: For patients who have vaccination with live, attenuated vaccines planned during the course of the study (based on national vaccination schedule/local guidelines), it will be determined, after consultation with a pediatrician, whether the administration of vaccine can be postponed until after the end of study, or preponed to before the start of the study, without compromising the health of the patient: Patients for whom administration of live (attenuated) vaccine can be safely postponed would be eligible to enroll into the study. Patients who have their vaccination preponed can enroll in the study only after a gap of 4 weeks following administration of the vaccine. 8. Planned or anticipated use of any prohibited medications and procedures during study treatment 9. Treatment with crisaborole within 2 weeks prior to the baseline visit. 10. Body weight <30 kg at baseline 11. Initiation of treatment of AD with prescription moisturizers or moisturizers containing additives such as ceramide, hyaluronic acid, urea, or filaggrin degradation products during the screening period (patients may continue using stable doses of such moisturizers if initiated before the screening visit) 12. Regular use (more than 2 visits per week) of a tanning booth/parlor within 4 weeks of the baseline visit 13. Active chronic or acute infection requiring treatment with systemic antibiotics, antivirals, antiprotozoals, or antifungals within 2 weeks before the baseline visit NOTE: patients may be rescreened after infection resolves 14. Known or suspected immunodeficiency, including history of invasive opportunistic infections (e.g., tuberculosis, histoplasmosis, listeriosis, coccidioidomycosis, pneumocystosis, aspergillosis) despite infection resolution, or otherwise recurrent infections of abnormal frequency or prolonged duration suggesting an immune-compromised status, as judged by the investigator 15. Known history of human immunodeficiency virus (HIV) infection or HIV seropositivity at the screening visit 16. With an established diagnosis of hepatitis B viral infection at the time of screening or is positive for hepatitis B surface antigen (HBsAg) or hepatitis B core antibody (HBcAb) at the time of screening NOTE: Patients who have gained immunity for hepatitis B virus infection after vaccination (patients who are HBsAg negative, hepatitis B surface antibody [HBsAb] positive, and HBcAb negative) are eligible for the study. These patients will be allowed to enroll into the study, but will be followed using routine clinical and liver function tests. 17. With an established diagnosis of hepatitis C viral infection at the time of screening or is positive for hepatitis C antibody at the screening visit 18. On current treatment for hepatic disease including but not limited to acute or chronic hepatitis, cirrhosis, or hepatic failure, or has evidence of liver disease as indicated by persistent (confirmed by repeated tests 22 weeks apart) elevated transaminases (alanine aminotransferase [ALT] and/or aspartate aminotransferase [AST]) more than 3 times the upper limit of normal (ULN) during the screening period 19. Presence of any 1 or more of the following abnormalities in laboratory test results at screening: •Platelets ≥100×10³/µL•Neutrophils<1.5×10³/µL•Creatine phosphokinase (CPK)>5×ULN•Serum creatinine>1.5×ULN NOTE: If an abnormal value is detected at screening, a repeat test should be performed to confirm the abnormality. Only if the repeat test confirms the abnormality, the patient would be categorized as a screen failure. 20. Presence of skin comorbidities that may interfere with study assessments 21. History of malignancy before the baseline visit 22. Diagnosed active endoparasitic infections; suspected or high risk of endoparasitic infection, unless clinical and (if necessary) laboratory assessment have ruled out active infection before randomization 23. History of alcohol or drug abuse within 2 years before the screening visit, or evidence of such abuse as documented by a positive result in a laboratory test for alcohol and/or drug panel conducted at the screening visit Note: If a patient has a positive drug test for a prescription drug being used for medical reasons, the patient would still be eligible for enrollment. In such cases, the site would need to confirm the medical reason for use with the treating physician. 24. Severe concomitant illness(es) that, in the investigator's judgment, would adversely affect the patients participation in the study. Examples include, but are not limited to patients with short life expectancy, patients with uncontrolled diabetes (hemoglobin A1c≥29%), patients with cardiovascular conditions (e.g., Class III or IV cardiac failure according to the New York Heart Association classification), severe renal conditions (e.g., patients on dialysis), hepato-biliary conditions (e.g., Child-Pugh class B or C), neurological conditions (e.g., demyelinating diseases), active major autoimmune diseases (e.g., lupus, inflammatory bowel disease, rheumatoid arthritis, etc.), other severe endocrinological, gastrointestinal, metabolic, pulmonary, or lymphatic diseases. The specific justification for patients excluded under this criterion will be noted in study documents (chart notes, case report forms [CRF], etc.). 25. Any other medical or psychological condition including relevant laboratory abnormalities at screening that, in the opinion of the investigator, suggest a new and/or insufficiently understood disease, may present an unreasonable risk to the study patient as a result of his/her participation in this clinical trial, may make patients participation unreliable, or may interfere with study assessments. The specific justification for patients excluded under this criterion will be noted in study documents (chart notes, CRF, etc.). 26. Patients who are committed to an institution by virtue of an order issued either by the judicial or the administrative authorities will be excluded from this study. 27. Planned major surgical procedure during the patient's participation in this study 28. Patient or his/her immediate family is a member of the dupilumab investigational team 29. Patient is female who is pregnant, breastfeeding, or planning to become pregnant or breastfeed during the study 30. Patient is female of childbearing potential* and sexually active, who is unwilling to use adequate methods of contraception** throughout the duration of the study and for 120 days after the last dose of study drug.

Study Treatments

Study Drug: Dupilumab was given every other week or every 4 weeks:

Dupilumab Q2W treatment:
 SC injections of dupilumab, 400 mg loading dose on day 1, then 200 mg Q2W from week 2 to week 14, or
 SC injections of dupilumab, 600 mg loading dose on day 1, then 300 mg Q2W from week 2 to week 14
Dupilumab Q4W treatment: SC injections of dupilumab, 600 mg loading dose on day 1, then 300 mg Q4W from week 4 to week 12; in order to maintain the blind, there was an SC injection of placebo in between dupilumab doses during the week 2 to week 14 dosing period so the injection frequency matched the other 2 groups.
Placebo: Matching Placebo
SC injections of placebo matching dupilumab Q2W (including doubling the amount of placebo on day 1 to match the loading dose). In order to maintain blinding for the study, patients in the <60 kg weight stratum who were randomized to the placebo group received, in a 1:1 ratio, either placebo matching 200 mg dupilumab (including doubling the amount of placebo on day 1 to match the loading dose) or placebo matching 300 mg dupilumab (including doubling the amount of placebo on day 1 to match the loading dose).

Background Treatment: All patients were required to apply moisturizers (emollients) at least twice daily for at least the 7 consecutive days immediately before randomization. After randomization, patients were required to continue to apply moisturizers throughout the study (all 28 weeks where applicable). However, to allow adequate assessment of skin dryness, moisturizers were not allowed to be applied on the area(s) of non-lesional skin designated for such assessments for at least 8 hours before each clinic visit. All types of moisturizers were permitted, but patients could not initiate treatment with prescription moisturizers or moisturizers containing additives during the screening period or during the study. Patients could continue using stable doses of such moisturizers if initiated before the screening visit.

Rescue Treatment: If medically necessary (i.e., to control intolerable AD symptoms), rescue treatment for AD was provided to study patients. If possible, investigators were encouraged to consider rescue initially with topical treatment (e.g., medium/high potency TCS) and to escalate to systemic medications only for patients who did not respond adequately after at least 7 days of topical treatment. Topical calcineurin inhibitors could be used for rescue, alone or in combination with TCS, but the use of TCIs was to be reserved for problem areas only (e.g., face, neck, intertriginous and genital areas, etc.). Investigators could also consider rescue with crisaborole. Rescue treatment for these topical therapies was to be used as per prescribing information and local guidelines. Patients could continue study treatment if rescue consisted of topical medications. Patients who received systemic corticosteroids or systemic non-steroidal immunosuppressive drugs (e.g., cyclosporine, methotrexate, mycophenolate-mofetil, azathioprine, etc.) as rescue medication during the study were discontinued permanently from the study drug.

Study Endpoints

The primary endpoint was proportion of patients with IGA 0 to 1 (on a 5-point scale) at week 16. The co-primary endpoints were proportion of patients with Eczema Area and Severity (EASI)-75 (≥75% improvement from baseline) at week 16, and proportion of patients with IGA 0 to 1 (on a 5-point scale) at week 16.

Key secondary endpoints included: •Percent change in EASI score from baseline to week 16•Percent change from baseline to week 16 in weekly average of daily peak Pruritus NRS•Proportion of patients with improvement (reduction) of weekly average of daily peak Pruritus NRS ≥3 from baseline to week 16•Proportion of patients with improvement (reduction) of weekly average of daily peak Pruritus NRS≥4 from baseline to week 16

Other secondary endpoints included: •Proportion of patients with EASI-50 at week 16•Proportion of patients with EASI-90 at week 16•Time to onset of effect on pruritus during the 16-week treatment period (≥3 point reduction of weekly average of peak Pruritus NRS from baseline)•Time to onset of effect on pruritus during the 16-week treatment period (≥4 point reduction of weekly average of peak Pruritus NRS from baseline)•Change from baseline to week 16 in percent body surface area (BSA) affected by AD•Percent change from baseline to week 16 in SCORing Atopic Dermatitis (SCORAD) Change from baseline to week 16 in Children's Dermatology Life Quality Index (CDLQI)•Change from baseline to week 16 in Patient Oriented Eczema Measure (POEM)•Change from baseline to week 16 in weekly average of daily peak Pruritus NRS•Percent change from baseline to week 4 in weekly average of daily peak Pruritus NRS•Change from baseline to week 16 in Hospital Anxiety and Depression Scale (HADS) •Proportion of patients with improvement (reduction) of weekly average of daily peak Pruritus NRS ≥4 from baseline to week 4 Incidence of skin-infection treatment-emergent adverse events (TEAEs) (excluding herpetic infections) through week 16•Incidence of serious TEAEs through week 16

Procedures and Assessments

Efficacy was assessed during the study at specified clinic visits using investigator-reported assessments (including IGA that rates the overall severity of AD, EASI that measures the extent and severity of AD, SCORAD, BSA affected by AD, and GISS). In addition, patient-reported assessments (including Pruritus NRS, Pruritus PCS, patient global assessment of disease, patient global assessment of treatment, CDLQI, POEM, HADS, 5-question version of Asthma Control Questionnaire [ACQ-5], Total Nasal Symptom Score [TNSS], patient assessment of injection pain using Visual Analogue Scale [VAS], and patient assessment of missed school days [for patients who are enrolled in school]) was used to assess their related endpoints. Safety was assessed by vital signs, physical examinations, clinical laboratory tests, 12-lead electrocardiograms (ECGs), and clinical evaluations. Patients were asked to monitor all adverse events (AEs) experienced from the time of informed consent/assent until their last study visit.

Patient Assessment of Pruritus Using Numerical Rating Scale: The Pruritus NRS is a simple assessment tool that patients use to report the intensity of their pruritus (itch) during a 24-hour recall period. Patients are asked the following question: For maximum itch intensity: "On a scale of 0 to 10, with 0 being 'no itch' and 10 being the 'worst itch imaginable', how would you rate your itch at the worst moment during the previous 24 hours?" Patients were instructed on using the patient diary to record their Pruritus NRS score at the screening and baseline visits. Patients complete the rating scale daily throughout the entire study (screening period, treatment period, and follow-up period).

Patient Assessment of Pruritus Using Pruritus Categorical Scale: The pruritus categorical scale is a 4-point scale used to assess symptoms that has been used in previous clinical studies of AD, and there is less of a tendency for patients to provide an "average" response than there might be with a 5-point scale (Kaufmann et al 2006, Allergy 61: 375-81). The scale is rated as follows: 0=absence of pruritus; 1=mild pruritus (occasional slight itching/scratching); 2=moderate pruritus (constant or intermittent itching/scratching that does not disturb sleep); and 3=severe pruritus (bothersome itching/scratching that disturbs sleep). Patients were instructed on using the patient diary to record their pruritus categorical scale score at the screening and baseline visits. Patients completed the rating scale daily throughout the entire study (screening period, treatment period, and follow-up period).

Patient Global Assessment of Disease: Patients rated their disease based on the 5-level scale as follows: Overall, how would you rate your eczema symptoms right now?•No symptoms•Mild symptoms•Moderate symptoms•Severe symptoms•Very severe symptoms Patients underwent this assessment at screening, at baseline and days 15, 29, 57, 85, 113, 141, 169 and 197 (end of study) or early termination.

Patient Global Assessment of Treatment: Patients responded to the following question based on the 5-level scale as follows: Compared to before you started the study, how would you rate your eczema symptoms now?•Much better•A little better•No difference•A little worse•Much worse Patients underwent this assessment on days 15, 29, 57, 85, 113, 141, 169, and 197 or early termination.

Children's Dermatology Life Quality Index: The CDLQI is a validated questionnaire designed to measure the impact of skin disease on the QOL in children (Lewis-Jones et al 1995, Brit. J. Dermatol. 132: 942-9). The aim of the questionnaire was to measure how much a patient's skin problem has affected the patient over a recall period of the past week. To complete the questionnaire, patients need to provide responses to 10 questions (the questions focus on domains such as symptoms, feelings associated with disease, the impact of the disease on leisure, school or holidays, personal relationships, sleep, and side effects of treatment for the skin disease). The instrument has a recall period of 7 days. Nine of the 10 questions are scored as follows: •Very much=3•Quite a lot=2•Only a little=1•Not at all=0•Question unanswered=0 Question 7 has an additional possible response (prevented school), which is assigned a score of 3. The CDLQI for a patient is the sum of the score of each question with a maximum of 30 and a minimum of 0. The higher the score, the greater the impact is on the QOL. The CDLQI can also be expressed as a percentage of the maximum possible score of 30. Patients underwent this assessment at screening, baseline, and on days 15, 29, 57, 85, 113, 141, 69, and 197 or early termination.

Patient Oriented Eczema Measure: The POEM is a 7-item, validated questionnaire used in clinical practice and clinical trials to assess disease symptoms in children and adults (Charman et al 2004, Arch. Dermatol. 140: 1513-9). The format is a response to 7 items (dryness, itching, flaking, cracking, sleep loss, bleeding, and weeping) based on frequency of these disease symptoms during the past week (i.e., 0=no days, 1=1 to 2 days, 2=3 to 4 days, 3=5 to 6 days, and 4=all days) with a scoring system of 0 to 28; the total score reflects disease-related morbidity. The questionnaire was administered at screening, baseline and on days 15, 29, 57, 85, 113, 141, 169, 197 or early termination.

Patient-Assessed Hospital Anxiety and Depression Scale: The HADS is an instrument for screening anxiety and depression in non-psychiatric populations; repeated administration also provides information about changes to a patient's emotional state (Zigmond and Snaith 1983, Acta Psychiatr. Scand 67: 361-70; Herrmann 1997, J. Psychosom. Res. 42: 17-41). The HADS consists of 14 items, 7 each for anxiety and depression symptoms; possible scores range from 0 to 21 for each subscale. The following cut-off scores are recommended for both subscales: 7 to 8 for possible presence, 10 to 11 for probable presence, and 14 to 15 for severe anxiety or depression. The questionnaire was administered only to the subset of patients who fluently spoke a language in which the questionnaire was presented (based on availability of validated translations in participating countries), at screening, baseline and on days 15, 29, 57, 85, 113, 141, 169, 197 or early termination.

Juniper Asthma Control Questionnaire-5: The 5-question version of the Juniper Asthma Control Questionnaire (ACQ) is a validated questionnaire to evaluate asthma control. The questionnaire was administered only to the subset of patients with ongoing asthma and who fluently spoke a language in which the questionnaire was presented (based on availability of validated translations in participating countries), at screening, baseline and on days 113 and 197 or early termination.

Total Nasal Symptom Score: The Total Nasal Symptom Score (TNSS) is used to assess the effect of study drug on symptoms of allergic rhinitis. The summed score includes the following 5 symptoms: rhinorrhea, nasal congestion, nasal itching, sneezing, and difficulty in sleeping, each rated on a 0 to 3 scale of severity. This instrument has been extensively used in previous trials conducted in patients with allergic rhinitis (Berger et al 2015, Am. J. Rhinol. Allergy 29: 273-82; Benninger et al 2010, Ann. Allergy Asthma Immunol. 104: 13-29). The questionnaire was administered only to the subset of patients with a medical history of allergic rhinitis who fluently spoke a language in which the questionnaire was presented (based on availability of translations in participating countries). Patients were instructed on using the patient diary to record their TNSS throughout the screening period (at least 7 days before baseline/day 1) and only for 7 days preceding visit 6, visit 18, and visit 21.

Injection Site Pain Visual Analogue Scale: Patients were asked to provide an assessment of pain experienced during injection of study drug using a Visual Analogue Scale (VAS). This assessment was performed after injection of the study drug at certain in-clinic visits on days 15, 29, 57, and 85.

Investigator's Global Assessment: The IGA is an assessment instrument used in clinical studies to rate the severity of AD globally, based on a 5-point scale ranging from 0 (clear) to 4 (severe). The IGA score was assessed at screening, baseline and on days 8, 15, 22, 29, 57, 85, 113, 141, 169, 197 (end of study) or early termination.

Eczema Area and Severity Index: The EASI is a validated measure used in clinical practice and clinical trials to assess the severity and extent of AD (Hanifin et al 2001, Exp. Dermatol. 10: 11-18). The EASI is a composite index with scores ranging from 0 to 72. Four AD disease characteristics (erythema, thickness [induration, papulation, edema], scratching [excoriation], and lichenification) will each be assessed for severity by the investigator or designee on a scale of "0" (absent) through "3" (severe). In addition, the area of AD involvement is assessed as a percentage by body area of head, trunk, upper limbs, and lower limbs, and converted to a score of 0 to 6. In each body region, the area is expressed as 0, 1 (1% to 9%), 2 (10% to 29%), 3 (30% to 49%), 4 (50% to 69%), 5 (70% to 89%), or 6 (90% to 100%). The EASI was collected at screening, baseline and on days 8, 15, 22, 29, 57, 85, 113, 141, 169, 197 (end of study) or early termination.

Global Individual Signs Score: Individual components of the AD lesions (erythema, infiltration/papulation, excoriations, and lichenification) are rated globally (i.e., each assessed for the whole body, not by anatomical region) on a 4-point scale (from 0=none to 3=severe) using the EASI severity grading criteria. The Global Individual Signs Score (GISS) was assessed at screening, baseline and on days 8, 15, 22, 29, 57, 85, 113, 141, 169, 197 (end of study) or early termination.

SCORing Atopic Dermatitis: The SCORing Atopic Dermatitis (SCORAD) is a validated tool used in clinical research and clinical practice that was developed to standardize the evaluation of the extent and severity of AD (European Task Force on Atopic Dermatitis 1993, Dermatol. 186: 23-31). There are 3 components to the assessment: A=extent or affected BSA, B=severity, and C=subjective symptoms. The extent of AD is assessed as a percentage of each defined body area and reported as the sum of all areas, with a maximum score of 100% (assigned as "A" in the overall SCORAD calculation). The severity of 6 specific symptoms of AD (redness, swelling, oozing/crusting, excoriation, skin thickening/lichenification, and dryness) is assessed using the following scale: none (0), mild (1), moderate (2), or severe (3) (for a maximum of 18 total points, assigned as "B" in the overall SCORAD calculation). Subjective assessment of itch and sleeplessness is recorded for each symptom by the patient or relative on a Visual Analogue Scale, where 0 is no itch (or sleeplessness) and 10 is the worst imaginable itch (or sleeplessness), with a maximum possible score of 20. This parameter is assigned as "C" in the overall SCORAD calculation. The SCORAD is calculated as: A/S+7B/2+C where the maximum is 103. Patients underwent this assessment at screening, baseline and on days 8, 15, 22, 29, 57, 85, 113, 141, 169, 197 (end of study) or early termination.

Body Surface Area Involvement of Atopic Dermatitis: Body surface area affected by AD is assessed for each section of the body using the rule of nines (the possible highest score for each region is: head and neck [9%], anterior trunk [18%], back [18%], upper limbs [18%], lower limbs [36%], and genitals [1%]) and is reported as a percentage of all major body sections combined. Patients underwent this assessment at screening, baseline and on days 8, 15, 22, 29, 57, 85, 113, 141, 169, 197 (end of study) or early termination.

Assessment of Missed School Days: Patients who are enrolled in school are asked to report the number of missed school days since the last study assessment. Patients underwent this assessment at baseline and on days 29, 57, 85, 113, 141, 169, 197 (end of study) or early termination.

Safety Assessment

Safety was assessed throughout the study by monitoring Adverse Events and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

Results

Baseline Characteristics

Baseline demographics and disease characteristics are summarized in Table 3.

TABLE 3

| Baseline Demographics and Disease Characteristics | | | | |
|---|---|---|---|---|
| | Placebo | Dupilumab 300 mg q4w | Dupilumab 200/300 mg q2w | Adolescent Overall |
| N (FAS) | 85 | 84 | 82 | 251 |
| Age (years), Mean (SD) | 14.5 (1.8) | 14.4 (1.6) | 14.5 (1.7) | 14.5 (1.70) |

TABLE 3-continued

Baseline Demographics and Disease Characteristics

| | Placebo | Dupilumab 300 mg q4w | Dupilumab 200/300 mg q2w | Adolescent Overall |
|---|---|---|---|---|
| Age group (years), n (%) | | | | |
| >=12-<15 | 41 (48.2%) | 45 (53.6%) | 43 (52.4%) | 129 (51.4%) |
| >=15-<18 | 44 (51.8%) | 39 (46.4%) | 39 (47.6%) | 122 (48.6%) |
| Gender (Male), n (%) | 53 (62.4%) | 52 (61.9%) | 43 (52.4%) | 148 (59.0%) |
| Race, n (%) | | | | |
| White | 48 (56.5%) | 55 (65.5%) | 54 (65.9%) | 157 (62.5%) |
| Black or African American | 15 (17.6%) | 8 (9.5%) | 7 (8.5%) | 30 (12.0%) |
| Asian | 13 (15.3%) | 13 (15.5%) | 12 (14.6%) | 38 (15.1%) |
| Weight (kg), Mean (SD) | 64.4 (21.5) | 65.8 (20.1) | 65.6 (24.5) | 65.2 (22.0) |
| Weight group n (%) | | | | |
| <60 kg | 43 (50.6%) | 42 (50.0%) | 43 (52.4%) | 128 (51.0%) |
| >=60 kg | 42 (49.4%) | 42 (50.0%) | 39 (47.6%) | 123 (49.0%) |
| BMI (kg/m^2), Mean (SD) | 23.9 (6.0) | 24.1 (5.9) | 24.9 (7.9) | 24.3 (6.6) |
| Duration of AD (yr), Mean (SD) | 12.3 (3.4) | 11.9 (3.2) | 12.5 (3.0) | 12.2 (3.2) |
| EASI (0-72), Mean (SD) | 35.5 (14.0) | 35.8 (14.8) | 35.3 (13.8) | 35.5 (14.2) |
| IGA (0-4), n (%) | | | | |
| 3 | 39 (45.9%) | 38 (45.2%) | 39 (47.6%) | 116 (46.2%) |
| 4 | 46 (54.1%) | 46 (54.8%) | 43 (52.4%) | 135 (53.8%) |
| Peak Pruritus NRS [0-10], Mean(SD) | 7.7 (1.6) | 7.5 (1.8) | 7.5 (1.5) | 7.6 (1.7) |
| BSA involvement (%), Mean (SD) | 56.4 (24.1) | 56.9 (23.5) | 56.0 (21.4) | 56.5 (23.0) |
| SCORAD (0-103), Mean (SD) | 70.4 (13.2) | 69.8 (14.1) | 70.6 (13.9) | 70.3 (13.7) |

Baseline demographics were comparable across the three treatment groups. Baseline disease severity was slightly higher in adolescents as compared to adults in earlier clinical studies.

TABLE 4

Disease Burden at Screening

| | Placebo (n = 85) | Dupilumab 300 mg q4w (n = 84) | Dupilumab 200/300 mg q2w (n = 82) | Total (N = 251) |
|---|---|---|---|---|
| BSA affected by AD, %, mean (SD) | 50.9 (23.1) | 52.7 (21.9) | 50.6 (21.5) | 51.4 (22.1) |
| Patients with IGA 4, n (%) | 38 (44.7%) | 41 (48.8%) | 34 (41.5%) | 113 (45.0%) |
| EASI score, mean (SD) | 31.4 (11.9) | 32.5 (13.5) | 31.8 (12.9) | 31.9 (12.8) |
| Peak Pruritus NRS score, mean (SD) | 7.3 (1.9) | 7.0 (2.0) | 7.4 (1.4) | 7.2 (1.8) |
| SCORAD total score, mean (SD)[a] | 66.4 (12.2) | 65.2 (13.6) | 66.1 (13.4) | 65.9 (13.0) |
| SCORAD VAS sleep loss score, mean (SD)[b] | 4.9 (2.9) | 5.1 (3.2) | 4.7 (3.1) | 4.9 (3.1) |
| POEM, mean (SD) | 20.3 (5.7) | 20.7 (5.3) | 21.2 (5.3) | 20.7 (5.4) |
| POEM severity categories, n (%) | | | | |
| Moderate disease, score 8-16 | 12 (14.1) | 19 (22.6) | 15 (18.3) | 46 (18.3) |
| Severe disease, score 17-24 | 53 (62.4) | 39 (46.4) | 39 (47.6) | 131 (52.2) |
| Very severe disease, score 25-28 | 18 (21.2) | 26 (31.0) | 27 (32.9) | 71 (28.3) |
| PGADS, n (%) | | | | |
| Moderate symptoms | 29 (34.1) | 27 (32.1) | 25 (30.5) | 81 (32.3) |
| Severe symptoms | 35 (41.2) | 37 (44.0) | 34 (41.5) | 106 (42.2) |
| Very severe symptoms | 11 (12.9) | 12 (14.3) | 15 (18.3) | 38 (15.1) |
| CDLQI total score, mean (SD)[c] | 13.0 (6.6) | 14.4 (7.3) | 12.4 (6.1) | 13.3 (6.7) |
| CDLQI response of 'quite a lot' or 'very much' on subscales, n (%)[c] | | | | |
| How itchy, sore, painful, stinging | 77 (90.6) | 73 (86.9) | 71 (86.6) | 221 (88.0) |
| How embarrassed, self-conscious | 42 (49.5) | 44 (52.4) | 41 (50.0) | 127 (50.6) |
| Affected friendships | 7 (8.3) | 11 (13.1) | 6 (7.4) | 24 (9.6) |
| Influenced clothes you wear | 35 (41.2) | 38 (45.2) | 29 (35.4) | 102 (40.6) |
| Affected leisure activity | 36 (42.4) | 41 (48.8) | 25 (30.5) | 102 (40.6) |
| Difficulty with sports | 30 (35.3) | 35 (41.7) | 28 (34.2) | 93 (37.1) |
| Problem at school or holiday | 31 (36.4) | 39 (46.4) | 31 (37.9) | 101 (40.2) |

TABLE 4-continued

Disease Burden at Screening

|  | Placebo (n = 85) | Dupilumab 300 mg q4w (n = 84) | Dupilumab 200/300 mg q2w (n = 82) | Total (N = 251) |
|---|---|---|---|---|
| Problem with other people | 12 (14.2) | 12 (14.3) | 9 (11.0) | 33 (13.2) |
| Affected sleep | 52 (61.2) | 50 (59.5) | 48 (58.6) | 150 (59.8) |
| How much treatment is a problem | 34 (40.0) | 42 (50.0) | 26 (31.7) | 102 (40.6) |
| HADS, total score, mean (SD)$^d$ | 11.4 (6.0) | 12.7 (7.4) | 12.1 (7.2) | 12.1 (6.9) |
| Anxiety, mean (SD)$^d$ | 7.2 (3.5) | 8.0 (4.5) | 8.1 (4.4) | 7.8 (4.2) |
| HADS-A ≥8, n (%) | 42 (49.4) | 44 (52.4) | 41 (50.0) | 127 (50.6) |
| HADS-A ≥11, n (%) | 15 (17.6) | 24 (28.6) | 25 (30.5) | 64 (25.5) |
| Depression, mean (SD)$^d$ | 4.2 (3.5) | 4.7 (4.0) | 3.9 (3.5) | 4.3 (3.6) |
| HADS-D ≥8, n (%) | 15 (17.6) | 18 (21.4) | 11 (13.4) | 44 (17.5) |
| HADS-D ≥11, n (%) | 4 (4.7) | 10 (11.9) | 4 (4.9) | 18 (7.2) |

Patients in this study had a mean age of 14.5 years and had a long duration of the disease (mean of 12.2 years). A majority (92%) had at least one allergic comorbidity, and 42.4% used prior systemic medications. The mean BSA affected by AD was 22.1%; 45% had IGA 4 (severe disease), while average EASI and SCORAD scores were 31.9 and 65.9, respectively. Mean Peak Pruritus NRS and SCORAD VAS sleep loss scores were 7.2/10 and 4.9/10, respectively. Mean POEM score was 20.7/28; 18.3%, 52.2%, and 28.3% patients reported moderate, severe, and very severe symptoms, respectively, based on the POEM scoring bands. Based on the PGADS classification, 32.3%, 42.2%, and 15.1% of patients experienced 'moderate', 'severe', and 'very severe' symptoms, respectively. On average, patients reported a very large effect on quality of life (mean CDLQI, 13.3/30). Symptoms of anxiety and depression were reported by 50.6% and 17.5% of patients, as defined by HADS-A/HADS-D scores of 28, respectively (Table 4).

Efficacy

Tables 5-7 summarize improvements in various AD-associated parameters in dupilumab-treated patients.

TABLE 5

Efficacy results for primary and key secondary endpoints

|  | Placebo | Dupilumab 300 mg q4w | Dupilumab 200/300 mg q2w |
|---|---|---|---|
| N | 85 | 84 | 82 |
| IGA 0-1 (%) at week 16 | 2.4% | 17.9% | 24.4% |
| EASI-75 (%) at week 16 | 8.2% | 38.1% | 41.5% |
| Mean % change EASI score from baseline to week 16 | −23.6% | −64.8% | −65.9% |
| Mean % change Peak Pruritus NRS from baseline to week 16 | −19% | −45.5% | −47.9% |
| Peak Pruritus NRS improvement ≥ 3 at week 16 | 9.4% | 38.6% | 48.8% |
| Peak Pruritus NRS improvement ≥ 4 at week 16 | 4.8% | 26.5% | 36.6% |

TABLE 6

Efficacy results for other secondary endpoints

|  | Placebo | Dupilumab 300 mg q4w | Dupilumab 200/300 mg q2w |
|---|---|---|---|
| N | 85 | 84 | 82 |
| Proportion of patients with EASI-50 | 12.9% | 54.8% | 61% |
| Proportion of patients with EASI-90 | 2.4% | 19% | 23.2% |
| Median time to onset of effect on pruritus during the 16-week treatment period (≥3 point reduction of weekly average of peak Pruritus NRS from baseline) (weeks) |  | 6 | 5.4 |
| Median time to onset of effect on pruritus during the 16-week treatment period (≥4 point reduction of weekly average of peak Pruritus NRS from baseline) (weeks) |  | 11 | 11 |
| Change from baseline in percent BSA affected by AD | −11.7% | −33.4% | −30.1% |
| Percent change from baseline in SCORAD | −17.6% | −47.5% | −51.6% |
| Change from baseline in CDLQI | −5.1 | −8.8 | −8.5 |
| Change from baseline in POEM | −3.8 | −9.5 | −10.1 |
| Change from baseline in weekly average of daily peak Pruritus NRS | −1.5 | −3.4 | −3.7 |
| Percent change from baseline to week 4 in weekly average of daily peak Pruritus | −12.5% | −33.1% | −34.7% |
| Change from baseline to week 16 in HADS | −2.5 | −5.2 | −3.8 |
| Proportion of patients with improvement (reduction) of weekly average of daily peak Pruritus NRS >=4 from baseline to week 4 | 4.8% | 20.5% | 22% |

TABLE 6-continued

Efficacy results for other secondary endpoints

| | Placebo | Dupilumab 300 mg q4w | Dupilumab 200/300 mg q2w |
|---|---|---|---|
| Incidence of skin-infection TEAEs (excluding herpetic infections) during 16-week treatment period | 18.8% | 9.5% | 9.8% |
| Incidence of serious TEAEs during 16-week treatment period | 1.2% | No SAE | No SAE |

TABLE 7

Proportion of patients that needed rescue medication

| | Placebo | Dupilumab 300 mg q4w | Dupilumab 200/300 mg q2w | Overall |
|---|---|---|---|---|
| N (SAF) | 85 | 83 | 82 | 250 |
| N (% pts Rescued by week 16) | 49 (57.6%) | 27 (32.5%) | 17 (20.7%) | 93 (37.2%) |

Mean (standard deviation) values for weekly average of daily Peak Pruritus NRS at baseline for dupilumab q2w/dupilumab q4w/placebo groups were 7.5 (1.52)/7.5 (1.84)/7.7 (1.62), respectively, consistent with severe pruritus. Significant improvement in pruritus with dupilumab vs placebo was seen as early as Day 5 for dupilumab q2w and Day 6 for dupilumab q4w regimens. At Day 5, least squares mean percentage change from baseline (standard error) in daily Peak Pruritus NRS score for dupilumab q2w/q4w vs placebo was −12.5 (2.43)/−8.8 (2.41) vs −4.9 (2.39); P<0.05/not significant. Day 6 values were: −13.0 (2.28)/−12.9 (2.27) vs 4.5 (2.24); P<0.01 for both. The improvement in itch scores continued to Day 15: −25.3 (2.68)/−21.8 (2.69) vs −5.7 (2.64); P<0.0001 for both. A higher proportion of patients in dupilumab q2w group showed clinically meaningful response (≥3-point improvement) in daily Peak Pruritus NRS score vs placebo group as early as Day 13 (P<0.05). By Day 15, significantly higher proportions of patients in both dupilumab groups achieved clinically meaningful improvement from baseline: 25.6%/25.3% vs 9.4% for dupilumab q2w/dupilumab q4w vs placebo, respectively; P<0.01 for both.

The placebo adjusted response was generally comparable to that seen in adult patients. Primary endpoint IGA (0,1) and co-primary endpoint EASI-75 at week 16 were met for both Q2W and 04W dose regimens. All pre-specified key efficacy endpoints were met for both doses. Both dupilumab treatment groups showed percent decrease in EASI as early as week 1 compared to placebo. For IGA, the dupilumab effect was seen as early as week 4 for both dose regimens as compared to placebo. The Q2W and Q4W treatment groups showed similar efficacy on continuous endpoints. However, the Q2W dose group showed numerically superior effect on IGA (0,1), NRS>4 and EASI-50. Both the treatment groups showed comparable effect until week 8 of treatment (due to loading dose effect), however Q2W showed numerically superior effect at subsequent time-points. The Q2W arm showed higher response as compared to Q4W in patients with severe disease (baseline IGA=4); both treatment groups outperformed placebo.

In both weight sub-groups, the dupilumab treatment groups outperformed placebo. In patients <60 kg, dupilumab 200 mg Q2W was numerically superior to dupilumab 300 mg Q4W. In patients ≥60 kg, dupilumab 300 mg Q2W was comparable to dupilumab 300 mg Q4W.

69 of 84, 62 of 82, and 83 of 85 patients did not achieve IGA 0/1 at Week 16 in the q4w/q2w/placebo groups, respectively. Among these patients, significantly greater improvement from baseline (least squares [LS] mean % change) was seen in q4w/q2w vs placebo groups in Eczema Area and Severity Index (EASI) (−58.4%/−55.0% vs −20.7%, respectively; P<0.0001 for both comparisons), pruritus Numerical Rating Scale (NRS; −41.2%/−44.2% vs −17.4%; P<0.0001 for both), Patient-Oriented Eczema Measure (POEM; −8.4%/−8.5% vs −3.5%; P<0.0001 for both), and Children's Dermatology Life Quality Index scores (LS mean change, −8.46/−8.44 vs −5.61; P=0.002 for both). More dupilumab-treated patients vs placebo achieved ≥50% improvement from baseline in EASI (44.9%/48.4% vs 10.8%; P<0.0001 for both), 23-point improvement in pruritus NRS (30.4%/43.5% vs 7.2%; P=0.0001/P<0.0001), 26-point reduction in POEM (39.1%/53.2% vs 8.5%; P<0.0001 for both) scores, and improvement in body surface area affected by AD (LS mean change, −31.32/−24.53 vs −10.78; P<0.0001/P=0.0002).

A higher proportion of patients in the Q4W arm needed use of rescue medications as compared to the Q2W arm (Table 7). However, dupilumab effect is robust and superior as compared to placebo over the course of treatment regardless of the use of rescue medication. The use of rescue medication had minimal effect on increasing response rates. Overall, a higher proportion of adolescent patients needed rescue medication as compared to adult patients, underscoring the severity of disease in adolescents. For primary analysis, patients on rescue medications were considered non-responders and data censored.

The adolescent patients showed high incidence of co-morbid allergic conditions (Table 8).

TABLE 8

Co-morbid allergic conditions in the patient population

|  | Placebo | Dupilumab 300 mg q4w | Dupilumab 200/300 mg q2w | Overall |
|---|---|---|---|---|
| Number of patients with at least one co-morbid allergic condition | 78 (91.8%) | 73 (88%) | 79 (96.3%) | 230 (92%) |
| ALLERGIC RHINITIS | 57 (67.1%) | 48 (57.8%) | 59 (72.0%) | 164 (65.6%) |
| ASTHMA | 46 (54.1%) | 42 (50.6%) | 46 (56.1%) | 134 (53.6%) |
| FOOD ALLERGY | 48 (56.5%) | 52 (62.7%) | 52 (63.4%) | 152 (60.8%) |
| ALLERGIC CONJUNCTIVITIS | 16 (18.8%) | 21 (25.3%) | 20 (24.4%) | 57 (22.8%) |
| HIVES | 22 (25.9%) | 28 (33.7%) | 22 (26.8%) | 72 (28.8%) |
| CHRONIC RHINOSINUSITIS | 7 (8.2%) | 6 (7.2%) | 6 (7.3%) | 19 (7.6%) |
| NASAL POLYPS | 2 (2.4%) | 1 (1.2%) | 2 (2.4%) | 5 (2.0%) |
| EOSINOPHILIC ESOPHAGITIS | 0 | 0 | 1 (1.2%) | 1 (0.4%) |
| OTHER ALLERGIES | 62 (72.9%) | 53 (63.9%) | 58 (70.7%) | 173 (69.2%) |

Table 9 shows the prior systemic medications used by the patients.

TABLE 9

Proportion of patients treated with prior systemic medications

|  | Placebo | Dupilumab 300 mg q4w | Dupilumab 200/300 mg q2w | Overall |
|---|---|---|---|---|
| N (SAF) | 85 | 83 | 82 | 250 |
| Patients receiving prior systemic medications for AD, n (%) | 33 (38.8%) | 38 (45.8%) | 35 (42.7%) | 106 (42.4%) |
| Patients receiving prior systemic corticosteroids, n (%) | 21 (24.7%) | 27 (32.5%) | 21 (25.6%) | 69 (27.6%) |
| Patients receiving prior systemic non-steroidal immunosuppressants | 17 (20.0%) | 15 (18.1%) | 20 (24.4%) | 52 (20.8%) |
| Azathioprine | 1 (1.2%) | 1 (1.2%) | 0 | 2 (0.8%) |
| Cyclosporine | 12 (14.1%) | 6 (7.2%) | 14 (17.1%) | 32 (12.8%) |
| Methotrexate | 6 (7.1%) | 10 (12.0%) | 10 (12.2%) | 26 (10.4%) |
| Mycophenolate | 0 | 1 (1.2%) | 2 (2.4%) | 3 (1.2%) |

A high proportion of patients used prior systemic medications. Systemic medications have been prescribed off-label based on limited evidence of efficacy and have been known to be associated with significant toxicities. The prior use of systemic medications and resultant lack of efficacy is confirmed by the baseline severity of disease in the study.

TABLE 10

Change in measures of sleep

| LS mean change (SE) from baseline | Placebo (n = 85) | Dupilumab 200/300 mg q2w (n = 82) | Dupilumab 300 mg q4w (n = 84) |
|---|---|---|---|
| SCORAD VAS sleep loss score (Week 1) | −0.52 (0.25) | −1.72 (0.26) | −1.13 (0.26) |
| P value vs placebo |  | 0.0009 | 0.0902 |
| SCORAD VAS sleep loss score (Week 16) | −1.12 (0.36) | −3.62 (0.32) | −3.04 (0.32) |
| P value vs placebo |  | <0.0001 | 0.0001 |
| CDLQI affected sleep score (Week 2)$^a$ | −0.23 (0.10) | −0.66 (0.09) | −0.74 (0.09) |
| P value vs placebo |  | 0.0013 | 0.0001 |
| CDLQI affected sleep score (Week 16) | −0.52 (0.13) | −1.18 (0.10) | −1.13 (0.11) |
| P value vs placebo |  | <0.0001 | 0.0005 |
| POEM disturbed sleep score (Week 2)$^a$ | −0.34 (0.13) | −0.87 (0.13) | −0.88 (0.13) |
| P value vs placebo |  | 0.0030 | 0.0028 |
| POEM disturbed sleep score (Week 16) | −0.43 (0.18) | −1.62 (0.14) | −1.55 (0.16) |
| P value vs placebo |  | <0.0001 | <0.0001 |

Dupilumab treatment demonstrated significant improvement in sleep vs placebo as early as Week 1 that was sustained through Week 16 (Table 10).

Safety

No new or unexpected side effects were observed in the trial compared to those seen in trials of adult patients. For the 16-week treatment period, the overall rate of adverse events was comparable between the dupilumab groups and placebo (72% for dupilumab every two weeks, 64% for dupilumab every four weeks and 69% for placebo). There were no serious adverse events or events leading to treatment discontinuation in either dupilumab treatment groups. As seen in trials of adult patients, skin infections (adjudicated including herpetic infections) were also numerically higher in the placebo group (11% for dupilumab every two weeks, 13.3% for dupilumab every four weeks compared with 20% for placebo). Adverse events that were observed at a higher rate with dupilumab included injection site reactions HLT (8.5% for dupilumab every two weeks, 6% for dupilumab every four weeks compared with 3.5% for placebo) and conjunctivitis CMQ (9.8% for dupilumab every two weeks, 10.8% for dupilumab every four weeks compared with 4.7% for placebo).

Clinical Pharmacology

Exposure was slightly lower in adolescents as compared to exposure predicted from adult PK studies. Exposure as measured by serum trough concentrations between 200 mg Q2W (<60 kg) and 300 mg Q2W (>60 kg) were comparable. Exposure for 300 mg Q4W was significantly lower in both weight groups. Higher exposure was associated with numerically higher response rate on 25% EASI. No high titer anti-drug antibodies (ADA) were observed. Low persistent ADA rates were observed across all treatment arms and placebo similar to adults.

At baseline, treatment groups had similar clinical and laboratory characteristics. Mean eosinophil counts ($\times 10^9$/L) were within normal range. Transient increases from baseline were observed in both dupilumab groups, with the highest mean increases at Week 8 (q4w 0.177; q2w 0.189: placebo −0.086). These increases had no clinical consequences, returning to baseline by Week 16. Mean changes from baseline through Week 16 in other hematologic parameters, though not meaningfully different between groups, were: leukocytes ($\times 10^9$/L, q4w 7.61; q2w 8.01; placebo 7.55); hemoglobin (g/L, q4w −0.8; q2w −1.2; placebo −0.8); platelets ($\times 10^9$/L, q4w −15.4; q2w −17.6; placebo −8.1). Mean changes in electrolyte and renal function parameters were also similar between groups, including potassium (mmol/L, q4w <0.1; q2w −0.01; placebo 0.04) and creatinine (μmol/L, q4w <0.1; q2w −1.3; placebo −1.1). No meaningful differences were found for alkaline phosphatase (U/L, q4w 5.3; q2w 12.4; placebo −5.7) and bilirubin (μmol/L, q4w −0.149; q2w 0.432; placebo 0.212).

Conclusion

Adolescent patients with moderate-to-severe AD have a substantial multi-dimensional disease burden as assessed by AD signs, patient-reported symptoms and impact on quality of life.

Dupilumab showed clinically meaningful and statistically significant improvement across different domains of AD in adolescents including in signs, symptoms and quality of life. The Q2W and 04W regimens were comparable for most endpoints; Q2W regimen was numerically superior to Q4W on certain categorical endpoints (e.g., NRS>4, IGA (0,1), EASI-50). Dupilumab treatment vs. placebo demonstrated rapid improvement in itch in adolescents with moderate-to-severe AD as early as Day 5 and clinically meaningful improvement by Day 13. The proportion of patients who needed rescue medication was higher in the 04W arm. Dupilumab was generally safe and well-tolerated in adolescents with AD. The adverse event profile was similar to that seen in adults. No new adolescent-specific safety signals were seen in the study. The incidence of SAEs and AEs leading to permanent discontinuation of treatment and commonly seen ADRs was slightly lower in adolescents as compared to adults. Both regimens were equally well-tolerated. Apart from injection site reactions, no dose-dependent toxicity was seen. PK exposure was lower in Q4W as compared to Q2W regimen. No clinically meaningful impact of ADA was observed on efficacy or safety. No clinically meaningful changes in laboratory parameters occurred with dupilumab treatment in adolescents with moderate-to-severe AD.

In adolescent patients not achieving IGA 0/1 at Week 16, dupilumab resulted in statistically significant and clinically meaningful improvements in other AD signs, symptoms, and QoL compared with placebo.

To summarize, treatment with dupilumab as monotherapy significantly improved measures of overall disease severity, skin clearing, itching and quality of life.

Example 3: Dupilumab in Adolescent Patients with Moderate-to-Severe Atopic Dermatitis and a History of Inadequate Response, Intolerance or Contraindication to Cyclosporine A: Results from a 16-Week Trial This Example describes outcomes in a subset of adolescents with inadequate response, intolerance or contraindication to cyclosporine A (CsA) from a phase 3 trial of dupilumab (DPL) (NCT03054428).

Patients (≥12-17 years) were randomized to subcutaneous dupilumab every 2 weeks (q2w; baseline [BL] weight <60 kg: 200 mg; BL weight ≥6 kg: 300 mg); every 4 weeks (q4w; 300 mg) or placebo (PBO) q2w, for 16 weeks (Wks). This analysis compares Wk 16 efficacy of DPL vs PBO in pts with inadequate response, intolerance or contraindication to CsA.

41/251 pts (PBO n=14; DPL q4w n=13; DPL q2w n=14) met the inclusion criteria for the analysis. DPL led to numerically higher proportions of pts with Investigator's Global Assessment scores 0/1 (q2w/q4w vs PBO 14.3%/ 7.7% vs 0%; P=0.1761/0.3173) and pts with 275% reduction in Eczema Area and Severity (EASI) scores (28.6%/30.8% vs 7.1%; P=0.1800/0.1495). DPL showed numerical improvement in EASI scores (% change: −51.5/−58.2 vs −12.7: P=0.0769/0.0521), and Peak Pruritus Numerical Rating Scale vs PBO ([PP-NRS]; −4.03/−3.83 vs −2.67; P=0.6437/0.5086). More DPL vs PBO pts achieved ≥3- and ≥4-point improvement in PP-NRS (57.1%/33.3% vs 7.1%; P=0.0036/0.1214 and 42.9%/16.7% vs 0%; P=0.0088/ 0.1343). DPL improved SCORing AD (SCORAD) sleep loss Visual Analog Scale (VAS) scores in pts with SCORAD sleep loss VAS 22 at BL (q2w/q4w vs PBO: −5.01/−6.37 vs −3.91: P=0.3525/0.0417); Patient-Oriented Eczema Measure (POEM) question #2 assessing sleep disturbance frequency (q2w/q4w vs PBO: −1.26/−2.57 vs −0.74; P=0.4022/ 0.0032); and Children's Dermatology Life Quality Index (CDLQI) question #9 assessing sleep impact (q2w/q4w vs PBO: −1.59/−2.08 vs −1.12; P=0.2100/0.0114). DPL improved POEM scores vs PBO (q2w/q4w vs PBO: −7.17/− 11.51 vs −2.12; P=0.1579/0.0128). Numerical improvement was seen with DPL vs PBO in CDLQI (q2w/q4w vs PBO: −9.34/−12.25 vs −7.87; P=0.4559/0.0590). More DPL vs PBO pts had meaningful within-person change (≥6-point improvement) in POEM and CDLQI (50.0%/46.2% vs 14.3%; P=0.0296/P=0.1037; and 64.3%/45.5% vs 15.4%; P=0.0221/0.1246). DPL was generally well tolerated in the overall population.

Dupilumab monotherapy improves skin lesions, symptoms and quality of life in this small subset of adolescents with moderate-to-severe AD and a history of inadequate response, intolerance, or contraindication to CsA The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for treating moderate-to-severe atopic dermatitis (AD) or improving an AD-associated parameter, the method comprising:
   administering an interleukin-4 receptor (IL-4R) inhibitor to a patient aged ≥12 years to <18 years with moderate-to-severe AD, wherein the IL-4R inhibitor is an antibody or antigen-binding fragment thereof that binds IL-4Rα, wherein the antibody or antigen-binding fragment thereof comprises three heavy chain complementarity determining regions (HCDR1, HCDR2, and HCDR3) and three light chain complementarity determining regions (LCDR1, LCDR2, and LCDR3), wherein the HCDR1 comprises the amino acid sequence of SEQ ID NO:3, the HCDR2 comprises the amino acid sequence of SEO ID NO. 4, the HCDR3 comprises the amino acid sequence of SEO ID NO:5, the LCDR1 comprises the amino acid sequence of SEO ID NO:6, the LCDR2 comprises the amino acid sequence of SEO ID NO:7, and the LCDR3 comprises the amino acid sequence of SEO ID NO. 8;
   wherein for a patient <60 kg in weight the IL-4R inhibitor is administered at (i) an initial dose of about 400 mg of the IL-4R inhibitor followed by one or more secondary doses of about 200 mg of the IL-4R inhibitor, wherein each secondary dose is administered two weeks after the immediately preceding dose; or for a patient ≥60 kg in weight the IL-4R inhibitor is administered at an initial dose of about 600 mg of the IL-4R inhibitor followed by one or more secondary doses of about 300 mg of the IL-4R inhibitor, wherein each secondary dose is administered two weeks after the immediately preceding dose.

2. The method of claim 1, wherein prior to or at the start of treatment the patient has an attribute selected from the group consisting of:
   (i) the patient has a baseline Investigator's Global Assembly (IGA) score=4;
   (ii) the patient has a baseline IGA score ≥3;
   (iii) the patient has a baseline Eczema Area and Severity (EASI) score ≥16;
   (iv) the patient has a baseline Pruritus Numerical Rating Scale (NRS) average score ≥4;
   (v) the patient has a ≥10% body surface area (BSA) of AD involvement at baseline;
   (vi) the patient has been previously treated with a topical AD medication; and
   (vii) the patient has a concomitant disease or disorder selected from the group consisting of food allergy, asthma, seasonal allergy, allergic conjunctivitis, allergic rhinitis, chronic rhinosinusitis, nasal polyps, house dust allergy, hives, and eosinophilic esophagitis.

3. The method of claim 1, wherein the patient has moderate-to-severe AD that is not adequately controlled with topical AD therapy.

4. The method of claim 1, wherein the patient is a patient with moderate-to-severe AD for whom topical AD therapy is not advisable.

5. The method of claim 1, wherein the patient is <60 kg in weight, and wherein the IL-4R inhibitor is administered at an initial dose of 400 mg followed by one or more secondary doses of 200 mg, wherein each secondary dose is administered two weeks after the immediately preceding dose.

6. The method of claim 1, wherein the patient is ≥60 kg in weight, and wherein the IL-4R inhibitor is administered at an initial dose of 600 mg followed by one or more secondary doses of 300 mg, wherein each secondary dose is administered two weeks after the immediately preceding dose.

7. The method of claim 1, wherein the administration of the IL-4R inhibitor results in an improvement a selected from the group consisting of: (i) an improvement of ≥75% in Eczema Area and Severity (EASI-75) from baseline to Week 16 after administration of the first dose of the IL-4R inhibitor, (ii) an improvement of ≥90% in Eczema Area and Severity (EASI-90) from baseline to Week 16 after administration of the first dose of the IL-4R inhibitor (iii) a reduction of ≥4 points in Peak Pruritus Numeric Rating Scale (NRS) score from baseline to Week 16 after administration of the first dose of the IL-4R inhibitor; (iv) achieving an Investigators Global Assessment (IGA) score of 0 or 1 by Week 16 after administration of the first dose of the IL-4R inhibitor, and/or (v) a reduction of ≥2 points in IGA score by Week 16 after administration of the first dose of the IL-4R inhibitor.

8. The method of claim 1, wherein the IL-4R inhibitor is administered in combination with a second therapeutic agent selected from the group consisting of a topical corticosteroid, a topical calcineurin inhibitor, an anti-histamine, an emollient, an anti-bacterial therapeutic, and a therapeutic agent for obstructive airway disease.

9. The method of claim 8, wherein the IL-4R inhibitor is administered combinations with topical corticosteroid.

10. The method of claim 1, wherein the antibody or antigen-binding fragment thereof comprises a heavy chain variable region (HCVR) comprising the amino acid sequence of SEQ ID NO: 1 and a light chain variable region (LCVR) comprising the amino acid sequence of SEQ ID NO: 2.

11. The method of claim 1, wherein the antibody or antigen-binding fragment thereof comprises a heavy chain comprising the amino acid sequence of SEQ ID NO: 9 and a light chain comprising the amino acid sequence of SEQ ID NO: 10.

12. The method of claim 1, wherein the IL-4R inhibitor is dupilumab or a bioequivalent thereof.

13. The method of claim 1, wherein the IL-4R inhibitor is administered subcutaneously.

14. The method of claim 13, wherein the IL-4R inhibitor is contained in a container selected from the group consisting of a glass vial, a syringe, a pre-filled syringe, an autoinjector and a microinfuser.

15. The method of claim 1, wherein the IL-4R inhibitor is contained in a pre-filled syringe.

16. The method of claim 15, wherein the pre-filled syringe is a single-dose pre-filled syringe.

17. The method of claim 1, wherein the IL-4R inhibitor is contained in an autoinjector.

18. The method of claim 14, wherein the IL-4R inhibitor is contained in a volume of 1.15 mL.

19. The method of claim 14, wherein the IL-4R inhibitor is contained in a volume of 2.25 mL.

20. The method of claim 17, wherein the autoinjector comprises a pre-filled syringe.

* * * * *

SEQUENCE LISTING

```
<160> NUMBER OF SEQ ID NOS: 11

<210> SEQ ID NO 1
<211> LENGTH: 124
<212> TYPE: PRT
<213> ORGANISM: Artificial Sequence
<220> FEATURE:
<223> OTHER INFORMATION: HCVR

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: LCVR

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

-continued

```
<210> SEQ ID NO 3
<211> LENGTH: 8
<212> TYPE: PRT
<213> ORGANISM: Artificial Sequence
<220> FEATURE:
<223> OTHER INFORMATION: HCDR1

<400> SEQUENCE: 3

Gly Phe Thr Phe Arg Asp Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: HCDR2

<400> SEQUENCE: 4

Ile Ser Gly Ser Gly Gly Asn Thr
1               5

<210> SEQ ID NO 5
<211> LENGTH: 18
<212> TYPE: PRT
<213> ORGANISM: Artificial Sequence
<220> FEATURE:
<223> OTHER INFORMATION: HCDR3

<400> SEQUENCE: 5

Ala Lys Asp Arg Leu Ser Ile Thr Ile Arg Pro Arg Tyr Tyr Gly Leu
1               5                   10                  15

Asp Val

<210> SEQ ID NO 6
<211> LENGTH: 11
<212> TYPE: PRT
<213> ORGANISM: Artificial Sequence
<220> FEATURE:
<223> OTHER INFORMATION: LCDR1

<400> SEQUENCE: 6

Gln Ser Leu Leu Tyr Ser Ile Gly Tyr Asn Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: LCDR2

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: LCDR3

<400> SEQUENCE: 8

Met Gln Ala Leu Gln Thr Pro Tyr Thr
1               5
```

<210> SEQ ID NO 9
<211> LENGTH: 451
<212> TYPE: PRT
<213> ORGANISM: Artificial Sequence
<220> FEATURE:
<223> OTHER INFORMATION: HC

<400> SEQUENCE: 9

```
Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365
```

```
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
            420                 425                 430
Met His Glu Ala Leu His Asn His Tyr Thr Gln Lys Ser Leu Ser Leu
        435                 440                 445
Ser Leu Gly
    450

<210> SEQ ID NO 10
<211> LENGTH: 219
<212> TYPE: PRT
<213> ORGANISM: Artificial Sequence
<220> FEATURE:
<223> OTHER INFORMATION: LC

<400> SEQUENCE: 10

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu Tyr Ser
            20                  25                  30
Ile Gly Tyr Asn Tyr Leu Asp Trp Tyr Leu Gln Lys Ser Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Phe Tyr Tyr Cys Met Gln Ala
                85                  90                  95
Leu Gln Thr Pro Tyr Thr Phe Gly Gln Gly Thr Lys Leu Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 11
<211> LENGTH: 207
<212> TYPE: PRT
<213> ORGANISM: Artificial Sequence
<220> FEATURE:
<223> OTHER INFORMATION: hIL-4Ralpha

<400> SEQUENCE: 11
```

```
Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
            85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
        130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
            165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205
```